US008691918B2

(12) United States Patent
Jaber et al.

(10) Patent No.: US 8,691,918 B2
(45) Date of Patent: Apr. 8, 2014

(54) STIMULUS RESPONSIVE POLYMERS FOR THE PURIFICATION OF BIOMOLECULES

(75) Inventors: Jad Jaber, Sudbury, MA (US); Wilson Moya, Concord, MA (US); James Hamzik, Chelmsford, MA (US); Arezki Boudif, Wakefield, MA (US); Yu Zhang, Chelmsford, MA (US); Neil Soice, Amherst, NH (US); John Charkoudian, Carlisle, MA (US); Nripen Singh, Burlington, MA (US)

(73) Assignee: EMD Millipore Corporation, Billerica, MA (US)

( * ) Notice: Subject to any disclaimer, the term of this patent is extended or adjusted under 35 U.S.C. 154(b) by 234 days.

(21) Appl. No.: 13/108,576

(22) Filed: May 16, 2011

(65) Prior Publication Data

US 2011/0313066 A1 Dec. 22, 2011

Related U.S. Application Data

(60) Provisional application No. 61/395,769, filed on May 17, 2010.

(51) Int. Cl.
*C08F 16/00* (2006.01)

(52) U.S. Cl.
USPC ................................ 525/328.2; 424/78.17

(58) Field of Classification Search
USPC .............................. 525/328, 328.2; 424/78.17
See application file for complete search history.

(56) References Cited

U.S. PATENT DOCUMENTS

| 3,556,302 | A | 1/1971 | Edward |
| 3,565,973 | A | 2/1971 | Michaels et al. |
| 3,632,507 | A | 1/1972 | Witt et al. |
| 3,702,806 | A | 11/1972 | Oliva |
| 3,737,377 | A | 6/1973 | Sternberg et al. |
| 3,859,212 | A | 1/1975 | Smalley et al. |
| 3,968,037 | A | 7/1976 | Morgan et al. |
| 4,045,377 | A | 8/1977 | Pearson |
| 4,055,469 | A | 10/1977 | Snoke et al. |
| 4,200,695 | A | 4/1980 | Chong et al. |
| 4,305,829 | A | 12/1981 | Kelsey et al. |
| 4,359,537 | A | 11/1982 | Chong |
| 4,371,674 | A | 2/1983 | Hertel et al. |
| 4,380,590 | A | 4/1983 | Chong |
| 4,382,028 | A | 5/1983 | Paget |
| 4,515,893 | A | 5/1985 | Kung et al. |
| 4,536,294 | A | 8/1985 | Guillet et al. |
| 4,676,980 | A | 6/1987 | Segal et al. |
| 4,780,409 | A | 10/1988 | Monji et al. |
| 4,816,567 | A | 3/1989 | Cabilly et al. |
| 4,828,701 | A | 5/1989 | Cussler |
| 4,839,046 | A | 6/1989 | Chandler |
| 4,863,613 | A | 9/1989 | Johnson et al. |
| 4,904,385 | A | 2/1990 | Wessling et al. |
| 4,912,032 | A | 3/1990 | Hoffman et al. |
| 4,925,785 | A | 5/1990 | Wang et al. |
| 4,968,435 | A | 11/1990 | Neff et al. |
| 5,003,047 | A | 3/1991 | Yarmush et al. |
| 5,047,511 | A | 9/1991 | Mehrotra |
| 5,091,178 | A | 2/1992 | Hellstrom et al. |
| 5,091,313 | A | 2/1992 | Chang |
| 5,152,903 | A | 10/1992 | Neff et al. |
| 5,164,057 | A | 11/1992 | Mori et al. |
| 5,171,450 | A | 12/1992 | Hoots |
| 5,238,545 | A | 8/1993 | Yoshioka et al. |
| 5,258,122 | A | 11/1993 | Ha et al. |
| 5,324,787 | A | 6/1994 | Pinschmidt, Jr. et al. |
| 5,340,865 | A | 8/1994 | Neff et al. |
| 5,354,481 | A | 10/1994 | Neff et al. |
| 5,354,801 | A | 10/1994 | O'Toole |
| 5,430,110 | A | 7/1995 | Ahlers et al. |
| 5,512,480 | A | 4/1996 | Sandstrom et al. |
| 5,573,675 | A | 11/1996 | Sommese et al. |
| 5,599,719 | A | 2/1997 | Woiszwillo et al. |
| 5,622,700 | A | 4/1997 | Jardieu et al. |
| 5,672,347 | A | 9/1997 | Aggarwal et al. |
| 5,684,107 | A | 11/1997 | Schneider et al. |
| 5,693,762 | A | 12/1997 | Queen et al. |
| 5,714,338 | A | 2/1998 | Wai Fei et al. |
| 5,721,108 | A | 2/1998 | Robinson et al. |
| 5,725,856 | A | 3/1998 | Hudziak et al. |
| 5,736,137 | A | 4/1998 | Anderson et al. |
| 5,739,383 | A | 4/1998 | Yoon et al. |
| 5,770,358 | A | 6/1998 | Dower et al. |
| 5,807,489 | A | 9/1998 | Farinato et al. |
| 5,840,804 | A | 11/1998 | Carl et al. |
| 5,840,851 | A | 11/1998 | Plomer et al. |
| 5,879,564 | A | 3/1999 | Farinato |
| 5,929,214 | A | 7/1999 | Peters et al. |
| 5,994,560 | A | 11/1999 | Yoon et al. |
| 5,998,588 | A | 12/1999 | Hoffman et al. |

(Continued)

FOREIGN PATENT DOCUMENTS

| EP | 0003089 B1 | 8/1981 |
| EP | 0162034 B1 | 11/1990 |

(Continued)

OTHER PUBLICATIONS

U.S. Appl. No. 13/155,912, Unpublished U.S. Appl. No. 13/155,912, filed Jun. 8, 2011, 50 pages.
Anastase-Ravion, et al., "New antibody purification procedure using a thermally responsive poly(N-isopropylacrylamide)—dextran derivative conjugate", Journal of Chromatography B: Biomedical Sciences and Applications, vol. 761, No. 2, Sep. 25, 2001, pp. 247-254.
Aruffo, et al., "CD44 is the principal cell surface receptor for hyaluronate", Cell, vol. 61, No. 7, Jun. 29, 1990, pp. 1303-1313.
Ayano, et al., "Aqueous chromatography system using pH- and temperature-responsive stationary phase with ion-exchange groups", Journal of Chromatography A, vol. 1119, Jun. 30, 2006, pp. 58-65.
Brennan, et al., "Preparation of bispecific antibodies by chemical recombination of monoclonal immunoglobulin G1 fragments", Science, vol. 229, Jul. 5, 1985, pp. 81-83.

(Continued)

*Primary Examiner* — Edward Cain
(74) *Attorney, Agent, or Firm* — EMD Millipore Corporation

(57) ABSTRACT

The present invention provides novel and improved stimulus responsive polymers and methods of using the same for the purification of biomolecules.

41 Claims, 15 Drawing Sheets

(56) References Cited

U.S. PATENT DOCUMENTS

| | | |
|---|---|---|
| 6,024,955 A | 2/2000 | Asano et al. |
| 6,127,526 A | 10/2000 | Blank |
| 6,133,047 A | 10/2000 | Elaissari et al. |
| 6,139,746 A | 10/2000 | Kopf |
| 6,147,176 A | 11/2000 | Neff et al. |
| 6,191,242 B1 | 2/2001 | Ryles et al. |
| 6,197,522 B1 | 3/2001 | Keller et al. |
| 6,245,555 B1 | 6/2001 | Curtis |
| 6,258,275 B1 | 7/2001 | Freitag et al. |
| 6,294,622 B1 | 9/2001 | Barajas et al. |
| 6,307,013 B1 | 10/2001 | Chivers |
| 6,358,730 B1 | 3/2002 | Kane |
| 6,372,141 B1 | 4/2002 | Okano et al. |
| 6,420,487 B1 | 7/2002 | Vaidya et al. |
| 6,454,950 B1 | 9/2002 | Tjerneld et al. |
| 6,521,341 B1 | 2/2003 | Elaissari et al. |
| 6,534,633 B1 | 3/2003 | Weidanz et al. |
| 6,538,089 B1 | 3/2003 | Samra et al. |
| 6,544,424 B1 | 4/2003 | Shevitz |
| 6,565,872 B2 | 5/2003 | Wu et al. |
| 6,582,926 B1 | 6/2003 | Chilkoti |
| 6,638,918 B2 | 10/2003 | Davison et al. |
| 6,641,735 B1 | 11/2003 | Yoshizako et al. |
| 6,673,598 B1 | 1/2004 | Akers et al. |
| 6,689,836 B2 | 2/2004 | Vaidya et al. |
| 6,706,187 B1 | 3/2004 | Okano et al. |
| 6,709,862 B2 | 3/2004 | Curtis |
| 6,737,235 B1 | 5/2004 | Cros et al. |
| 6,765,081 B2 | 7/2004 | Lin et al. |
| 6,770,758 B2 | 8/2004 | Pan et al. |
| 6,805,793 B2 | 10/2004 | Yoshizako et al. |
| 6,821,515 B1 | 11/2004 | Cleland et al. |
| 6,830,670 B1 | 12/2004 | Viovy et al. |
| 6,852,819 B2 | 2/2005 | Ohnishi et al. |
| 6,858,694 B2 | 2/2005 | Ohnishi et al. |
| 6,863,437 B2 | 3/2005 | Ohnishi et al. |
| 6,867,268 B2 | 3/2005 | Vaidya et al. |
| 6,926,832 B2 | 8/2005 | Collins et al. |
| 6,956,077 B1 | 10/2005 | Akiyama et al. |
| 6,967,085 B1 | 11/2005 | Hughes et al. |
| 6,974,660 B2 | 12/2005 | Manias et al. |
| 7,001,953 B2 | 2/2006 | Chen et al. |
| 7,011,930 B2 | 3/2006 | Manias et al. |
| 7,012,136 B2 | 3/2006 | Yamanaka et al. |
| 7,052,917 B1 | 5/2006 | Ohnishi et al. |
| 7,070,696 B2 | 7/2006 | Weir et al. |
| 7,083,948 B1 | 8/2006 | Sassenfeld et al. |
| 7,157,603 B2 | 1/2007 | Hilbrig |
| 7,160,971 B2 | 1/2007 | Mallapragada et al. |
| 7,169,908 B2 | 1/2007 | Lester et al. |
| 7,195,925 B2 | 3/2007 | Ohnishi et al. |
| 7,300,545 B2 | 11/2007 | Ohara et al. |
| 7,355,020 B2 | 4/2008 | Yamanaka et al. |
| 7,377,686 B2 | 5/2008 | Hubbard |
| 7,393,698 B2 | 7/2008 | Furukawa et al. |
| 7,422,724 B1 | 9/2008 | Manginell et al. |
| 7,429,458 B2 | 9/2008 | Chilkoti |
| 7,442,515 B2 | 10/2008 | Ratner et al. |
| 7,514,007 B2 | 4/2009 | Chen et al. |
| 7,541,167 B2 | 6/2009 | Dave et al. |
| 7,547,747 B2 | 6/2009 | Hashimoto et al. |
| 7,553,658 B2 | 6/2009 | Kepka et al. |
| 7,625,764 B2 | 12/2009 | Stayton et al. |
| 7,632,656 B2 | 12/2009 | Kanazawa et al. |
| 7,695,905 B2 | 4/2010 | Furukawa et al. |
| 7,767,399 B2 | 8/2010 | Murphy et al. |
| 8,163,886 B2 | 4/2012 | Moya |
| 2002/0058786 A1 | 5/2002 | Chivers |
| 2002/0098567 A1 | 7/2002 | Vaidya et al. |
| 2003/0059840 A1 | 3/2003 | Chilkoti |
| 2003/0186293 A1 | 10/2003 | Ohnishi et al. |
| 2004/0010163 A1 | 1/2004 | Hilbrig |
| 2004/0039177 A1 | 2/2004 | Yamanaka et al. |
| 2004/0062140 A1 | 4/2004 | Cadogan et al. |
| 2004/0134846 A1 | 7/2004 | Akiyama et al. |
| 2005/0016620 A1 | 1/2005 | Proulx et al. |
| 2005/0063259 A1 | 3/2005 | Isshiki et al. |
| 2005/0158782 A1 | 7/2005 | Furukawa et al. |
| 2005/0158851 A1 | 7/2005 | Furey |
| 2005/0175702 A1 | 8/2005 | Muller-Schulte |
| 2005/0224415 A1 | 10/2005 | Akiyama et al. |
| 2005/0272146 A1 | 12/2005 | Hodge et al. |
| 2005/0282169 A1 | 12/2005 | Turner et al. |
| 2006/0121519 A1 | 6/2006 | Patchornik |
| 2006/0162882 A1 | 7/2006 | Ohara et al. |
| 2006/0189795 A1 | 8/2006 | Van Alstine et al. |
| 2006/0251610 A1 | 11/2006 | Nakahama |
| 2007/0148437 A1 | 6/2007 | Muller-Schulte |
| 2007/0193954 A1 | 8/2007 | Busson |
| 2007/0224241 A1 | 9/2007 | Stayton et al. |
| 2007/0249737 A1 | 10/2007 | Miller et al. |
| 2008/0131957 A1 | 6/2008 | Ryan et al. |
| 2008/0160559 A1 | 7/2008 | Carre et al. |
| 2008/0193981 A1 | 8/2008 | Fahrner et al. |
| 2008/0220531 A1 | 9/2008 | Stayton et al. |
| 2008/0255027 A1 | 10/2008 | Moya et al. |
| 2008/0284163 A1 | 11/2008 | Proulx et al. |
| 2008/0293118 A1 | 11/2008 | Furukawa et al. |
| 2008/0293926 A1 | 11/2008 | Hallgren et al. |
| 2009/0001025 A1 | 1/2009 | Takahashi et al. |
| 2009/0036651 A1 | 2/2009 | Moya |
| 2009/0148961 A1 | 6/2009 | Luchini et al. |
| 2009/0155201 A1 | 6/2009 | Mandeville, III et al. |
| 2009/0232737 A1 | 9/2009 | Moya et al. |
| 2009/0233327 A1 | 9/2009 | Lau et al. |
| 2009/0311776 A1 | 12/2009 | Kelly, Jr. et al. |
| 2010/0190963 A1 | 7/2010 | Moya et al. |
| 2010/0193148 A1 | 8/2010 | McKay et al. |
| 2010/0267933 A1 | 10/2010 | Wilson |
| 2010/0282425 A1 | 11/2010 | Karppi et al. |
| 2011/0020327 A1 | 1/2011 | Moya et al. |
| 2011/0313066 A1 | 12/2011 | Jaber et al. |

FOREIGN PATENT DOCUMENTS

| | | |
|---|---|---|
| EP | 0534016 A1 | 3/1993 |
| EP | 0420937 B1 | 11/1994 |
| EP | 0922715 A2 | 6/1999 |
| EP | 0922715 A3 | 11/2003 |
| EP | 1923461 A1 | 5/2008 |
| GB | 2305936 A | 4/1997 |
| WO | 91/00360 A1 | 1/1991 |
| WO | 92/20373 A1 | 11/1992 |
| WO | 93/04173 A1 | 3/1993 |
| WO | 93/04713 A1 | 3/1993 |
| WO | 93/08829 A1 | 5/1993 |
| WO | 93/14110 A1 | 7/1993 |
| WO | 93/16185 A2 | 8/1993 |
| WO | 94/15951 A1 | 7/1994 |
| WO | 95/06249 A1 | 3/1995 |
| WO | 95/19181 A1 | 7/1995 |
| WO | 95/23865 A1 | 9/1995 |
| WO | 96/02577 A1 | 2/1996 |
| WO | 96/27011 A1 | 9/1996 |
| WO | 96/30046 A1 | 10/1996 |
| WO | 96/40210 A1 | 12/1996 |
| WO | 97/26912 A2 | 7/1997 |
| WO | 98/06248 A2 | 2/1998 |
| WO | 98/23761 A1 | 6/1998 |
| WO | 98/33162 A1 | 7/1998 |
| WO | 98/45331 A2 | 10/1998 |
| WO | 98/51793 A1 | 11/1998 |
| WO | 99/01556 A2 | 1/1999 |
| WO | 00/12618 A1 | 3/2000 |
| WO | 00/46262 A1 | 8/2000 |
| WO | 00/67901 A1 | 11/2000 |
| WO | 00/75348 A1 | 12/2000 |
| WO | 01/07548 A1 | 2/2001 |
| WO | 01/40309 A2 | 6/2001 |
| WO | 2004/056312 A2 | 7/2004 |
| WO | 2004/092393 A1 | 10/2004 |
| WO | 2005/010141 A2 | 2/2005 |
| WO | 2005/021129 A1 | 3/2005 |
| WO | 2005/108546 A2 | 11/2005 |

(56) References Cited

FOREIGN PATENT DOCUMENTS

| | | | |
|---|---|---|---|
| WO | 2005/118771 A2 | 12/2005 |
| WO | 2006/085321 A2 | 8/2006 |
| WO | 2006/138143 A1 | 12/2006 |
| WO | 2007/002690 A1 | 1/2007 |
| WO | 2007/038523 A2 | 4/2007 |
| WO | 2007/073311 A1 | 6/2007 |
| WO | 2007/104456 A1 | 9/2007 |
| WO | 2007/148230 A2 | 12/2007 |
| WO | 2008/004988 A1 | 1/2008 |
| WO | 2008/079280 A1 | 7/2008 |
| WO | 2008/079302 A2 | 7/2008 |
| WO | 2008/091740 A2 | 7/2008 |
| WO | 2008/097154 A1 | 8/2008 |
| WO | 2009/089570 A1 | 7/2009 |
| WO | 2009/141664 A1 | 11/2009 |
| WO | 2009/158606 A2 | 12/2009 |
| WO | 2010/082894 A1 | 7/2010 |

OTHER PUBLICATIONS

Brodeur, et al., "Monoclonal Antibody Production Techniques and Applications", Marcel Dekker, Inc., New York, 1987, pp. 51-63.

Brüggemann, et al., "Designer mice: the production of human antibody repertoires in transgenic animals", The Year in Immunology, vol. 7, 1993, pp. 33-40.

Carter, et al., "High Level Escherichia coli Expression and Production of a Bivalent Humanized Antibody Fragment", Nature Biotechnology, vol. 10, 1992, pp. 163-167.

Carter, et al., "Highly Branched Stimuli Responsive Poly[(N-isopropyl acrylamide)-co-(1,2-propandiol-3-methacrylate)]s with Protein Binding Functionality", Macromolecular Bioscience, vol. 5, No. 5, May 23, 2005, pp. 373-378.

Carter, et al., "Humanization of an anti-p185HER2 antibody for human cancer therapy", Proc. Natl. Acad. Sci. USA, vol. 89, May 1992, pp. 4285-4289.

Cellseed Inc., "Technology: Temperature-responsive polymers", document retrieved on Oct. 13, 2010, available at: http://www.cellseed.com/technology-e/index.html.

Ceriani, et al., "Biological Activity of Two Humanized Antibodies against Two Different Breast Cancer Antigens and Comparison to Their Original Murine Forms", Cancer Research (Suppl.), vol. 55, Dec. 1, 1995, pp. 5852s-5856s.

Chen, et al., "A new temperature- and pH-responsive copolymer for possible use in protein conjugation", Macromolecular Chemistry and Physics, vol. 196, No. 4, Apr. 1995, pp. 1251-1259.

Chen, et al., "Graft copolymers that exhibit temperature-induced phase transitions over a wide range of pH", Nature, vol. 373, No. 5, Jan. 5, 1995, pp. 49-52.

Chen, et al., "pH-Dependence of the Properties of Hydrophobically Modified Polyvinylamine", Langmuir, vol. 21, No. 25, 2005, pp. 11673-11677.

Chen, et al., "Polymer-protein conjugates. II. Affinity precipitation separation of human immunogammaglobulin by a poly(N-isopropylacrylamide)-protein A conjugate", Biomaterials, vol. 11, No. 9, 1990, pp. 631-634.

Chern, et al., "Characterization of pH-sensitive polymeric supports for selective precipitation of proteins", Colloids and Surfaces B: Biointerfaces vol. 6, 1996, pp. 37-49.

Chothia, et al., "Canonical Structures for the Hypervariable Regions of Immunoglobulins", Journal of Molecular Biology, vol. 196, No. 4, Aug. 20, 1987, pp. 901-917.

Choy, et al., "Percentage of anti-CD4 monoclonal antibody-coated lymphocytes in the rheumatoid joint is associated with clinical improvement. Implications for the development of immunotherapeutic dosing regimens", Arthritis & Rheumatism, vol. 39, No. 1, Jan. 1996, pp. 52-56.

Clackson, et al., "Making antibody fragments using phage display libraries", Nature, vol. 352, Aug. 15, 1991, pp. 624-628.

Dainiak, et al., "Affinity precipitation of monoclonal antibodies by nonstoichiometric polyelectrolyte complexes", Bioseparation, vol. 7, No. 4-5 (Abstract Only supplied), Jul. 1, 1999, pp. 231-240.

Deng, et al., "Temperature-Sensitive Flocculants Based on Poly(N-isopropylacrylamide-co-diallyldimethylammonium Chloride)", Journal of Colloid and Interface Science, vol. 179, No. 1, Apr. 15, 1996, pp. 188-193.

Dhainaut, et al., "CDP571, a humanized antibody to human tumor necrosis factor-alpha: Safety, pharmacokinetics, immune response, and influence of the antibody on cytokine concentrations in patients with septic shock", Critical Care Medicine, vol. 23, No. 9, Sep. 1995, pp. 1461-1469.

Ding, et al., "Size-dependent control of the binding of biotinylated proteins to streptavidin using a polymer shield", Nature, vol. 411, May 3, 2001, pp. 59-62.

Duchosal, et al., "Immunization of hu-PBL-SCID mice and the rescue of human monoclonal Fab fragments through combinatorial libraries", Nature, vol. 355, Jan. 16, 1992, pp. 258-262.

Eisenberg, et al., "Viscosities of dilute aqueous solutions of a partially quaternized poly-4-vinylpyridine at low gradients of flow", Journal of Polymer Science, vol. 13, No. 68, Feb. 1954, pp. 85-91.

Ellis, et al., "Engineered anti-CD38 monoclonal antibodies for immunotherapy of multiple myeloma", The Journal of Immunology, vol. 155, No. 2, 1995, pp. 925-937.

Eriksson, et al., "Flocculation of E.coli Bacterial With Cationic Polyelectrolytes", Flocculation in Biotechnology and Separation Systems, 1987, pp. 441-455.

Esser, et al. "Genetic Control of Flocculation of Yeast With Respect to Application in Biotechnology", Flocculation in Biotechnology and Separation Systems, 1987, pp. 383-398.

Ferreira, et al., "Purification of human immunoglobulin G by thermoseparating aqueous two-phase systems", Journal of Chromatography A, vol. 1195, 2008, pp. 94-100.

Fong, et al., "Affinity Separation Using an Fv Antibody Fragment-"Smart" Polymer Conjugate", BioTechnology and BioEngineenng, vol. 79, No. 3, Aug. 5, 2002, pp. 271-276.

Fong, et al., "Thermoprecipitation of Streptavidin via Oligonucleotide-Mediated Self-Assembly with Poly(N-isopropylacrylaminde)", Bioconjugate Chem., vol. 10, 1999, pp. 720-725.

Freitag, et al., "Stimulus-Responsive Polymers for Bioseparation", Chimia, vol. 55, No. 3, 2001, pp. 196-200.

Galaev, I Yu, "'Smart' polymers in biotechnology and medicine", Russian Chemical Reviews, vol. 64 No. 5, 1995, pp. 471-489.

Garret-Flaudy, et al., "Use of the Avidin (Imino) biotin System as a General Approach to Affinity Precipitation", BioTechnology and BioEngineering, vol. 71, No. 3, 2000/2001, pp. 223-234.

Gawande, et al., "Purification of Aspergillus sp xylanase by precipitation with an anionic polymer Eudragit S100", Process Biochemistry, vol. 34, No. 6-7, Sep. 1999, pp. 577-580.

Gil, et al., "Stimuli-reponsive polymers and their bioconjugates", Progress in Polymer Science, vol. 29, No. 12, Dec. 2004, pp. 1173-1222.

Goding, "Monoclonal Antibodies: Principles and Practice", Academic Press. 1986, pp. 59-103.

Graziano, et al., "Construction and characterization of a humanized anti-gamma-Ig receptor type I (Fc gamma RI) monoclonal antibody", The Journal of Immunology, vol. 155, No. 10, 1995, pp. 4996-5002.

Gruber, et al., "Efficient tumor cell lysis mediated by a bispecific single chain antibody expressed in Escherichia coli", The Journal of Immunology, vol. 152, No. 11, 1994, pp. 5368-5374.

Guoqiang, et al., "Alternative modes of precipitation of Eudragit S-100: a potential ligand carrier for affinity precipitation of protein", Bioseparation, vol. 5, 1995, pp. 339-350.

Gupta, et al., "Affinity Precipitation of Proteins", Journal of Molecular Recognition, vol. 9, 1996, pp. 356-359.

Han, et al., "Flocculation of biological cells: Experiment vs. theory", AIChE Journal, vol. 49, No. 7, Jul. 2003, pp. 1687-1701.

Hayashi, et al., "Capturing of acidic macromolecules from biological samples using a temperature-responsive polymer modified with poly-L-lysine", Analyst, vol. 129, 2004, pp. 421-427.

Hilbrig, et al., "Protein purification by affinity precipitation", Journal of Chromatography B: Biomedical Sciences and Applications, vol. 790, Jun. 25, 2003, pp. 79-90.

(56) References Cited

OTHER PUBLICATIONS

Holliger, et al., "Diabodies: small bivalent and bispecific antibody fragments", The Proceedings of the National Academy of Sciences, USA, vol. 90, No. 14., Jul. 15, 1993, pp. 6444-6448.
Hoogenboom, et al., "By-passing immunisation : Human antibodies from synthetic repertoires of germline VH gene segments rearranged in vitro", Journal of Molecular Biology, vol. 227, No. 2, Sep. 20, 1992, pp. 381-388.
Hoogenboom, et al., "Construction and expression of antibody-tumor necrosis factor fusion proteins", Molecular Immunology, vol. 28, No. 9, Sep. 1991, pp. 1027-1037.
Hoshino, et al., "Preparation of a New Thermo-Responsive Adsorbent with Maltose as a Ligand and Its Application to Affinity Precipitation", BioTechnology and BioEngineering, vol. 60, No. 5, Dec. 5, 1998, pp. 568-579.
Zuker, Michael "Mfold web server for nucleic acid folding and hybridization prediction", Nucleic Acids Research, vol. 31, No. 13, Jul. 1, 2003, pp. 3406-3415.
International Search Report and Written Opinion received for PCT Application No. PCT/US2011/039595, mailed on Dec. 6, 2011, 15 pages.
Fujii et al., "Application of Reversibly soluble polymers in Bioprocessing", Trends in Biotechnology, vol. 9, 1991, pp. 191-196.
Galaev et al., "'Smart' Polymers and What They Could Do in Biotechnology and Medicine", Trends in Biotechnology, vol. 17, No. 8, Aug. 1999, pp. 335-340.
Agarwal et al., "Sequential Precipitation with Reversibly Soluble Insoluble Polymers as a Bioseparation Strategy: Purification of β-Glucosidase from *Trichoderma longibrachiatum*", Protein Expression and Purification, vol. 7, 1996, pp. 294-298.
Galaev et al., "Interaction of Cibacron Blue with Polymers: Implications for Polymer-Shielded Dye-Affinity Chromatography of Phosphofructokinase from Baker's Yeast", Journal of Chromatography A, vol. 684, 1994, pp. 45-54.
Lali et al., "Carboxymethyl Cellulose as a New Heterobifunctional Ligand Carrier for Affinity Precipitation of Proteins", Bioseparation, vol. 7, 1999, pp. 195-205.
Lehermayr et al., "Assessment of Net Charge and Protein—Protein Interactions of Different Monoclonal Antibodies", Journal of Pharmaceutical Sciences, vol. 100, No. 7, Jul. 2011, pp. 2551-2562.
International Search Report and Written Opinion received for PCT Application No. PCT/US2011/036648, mailed on Oct. 31, 2011, 5 pages.
Seo, et al., "Self-organization of poly(allylamine)s Containing Hydrophobic Groups and Its Effect on the Interaction With Small Molecules. 1. Static Fluorometry", Macromolecules, vol. 24, No. 15, 1991, pp. 4255-4263.
Roush, et al., "Advances in Primary Recovery: Centrifugation and Membrane Technology", Biotechnology Progress, vol. 24, No. 3, May/Jun. 2008, pp. 488-495.
Saitoh, et al., "Concentration of Hydrophobic Organic Compounds by Polymer-Mediated Extraction", Anal. Chem., vol. 71, No. 20, 1999, pp. 4506-4512.
Sakohara, et al., "Flocculation Mechanism of Suspended Particles Using the Hydrophilic/Hydrophobic Transition of a Thermosensitive Polymer", Kona, No. 20, 2002, pp. 246-250.
Schmaljohann, "Thermo-and pH-responsive polymers in drug delivery", Advanced drug delivery reviews, vol. 58, No. 15, 2006, pp. 1655-1670.
Schwarz, et al., "Cationic Flocculants Carrying Hydrophobic Functionalities: Applications for Solid/Liquid Separation", The Journal of Physical Chemistry B, vol. 111, No. 29, 2007, pp. 8649-8654.
Senstad, et al., "Purification of Wheat Germ Agglutinin Using Affinity Flocculation with Chitosan and a Subsequent Centrifugation or Flotation Step", Biotechnology and Bioengineering, vol. 34, Jan. 1, 1989, pp. 387-393.
Shalaby, et al., "Development of humanized bispecific antibodies reactive with cytotoxic lymphocytes and tumor cells overexpressing the HER2 protooncogene", J. Exp. Med., vol. 175, Jan. 1, 1992, pp. 217-225.

Shan, et al., "Flocculation of cell, cell debris and soluble protein with methacryloyloxyethyl trimethylammonium chloride—acrylonitrile copolymer", Journal of Biotechnology, vol. 49, 1996, pp. 173-178.
Sharkey, et al., "Evaluation of a complementarity-determining region-grafted (humanized) anti-carcinoembryonic antigen monoclonal antibody in preclinical and clinical studies", Cancer Research (Suppl.) vol. 55, 1995, pp. 5935s-5945s.
Sims, et al., "A humanized CD18 antibody can block function without cell destruction", The Journal of Immunology, vol. 151, No. 4, 1993, pp. 2296-2308.
St. John, et al., "Immunologic therapy for ARDS, septic shock, and multiple-organ failure", Chest, vol. 103, 1993, pp. 932-943.
Stamenkovic, et al., "The B lymphocyte adhesion molecule CD22 interacts with leukocyte common antigen CD45RO on T cells and α2-6 sialyltransferase, CD75, on B cells", Cell, vol. 66, No. 6, Sep. 20, 1991, pp. 1133-1144.
Stoppa, et al., "Anti-LFA1 monoclonal antibody (25.3) for treatment of steroid-resistant grade III-IV acute graft-vershost disease", Transplant International, vol. 4, No. 1, Jan. 1991, pp. 3-7.
Suedee, et al., "Temperature sensitive dopamine-imprinted (N,N-methylene-bis-acrylamide cross-linked) polymer and its potential application to the selective extraction of adrenergic drugs from urine", Journal of Chromatography A, vol. 1114, May 12, 2006, pp. 239-249.
Toei, Kyoji "Ion-Association Reagents A Review", Analytical Sciences, vol. 3, No. 6, 1987, pp. 479-488.
Traunecker, et al., "Bispecific single chain molecules (Janusins) target cytotoxic lymphocytes on HIV infected cells", The EMBO Journal, vol. 10, No. 12, Jul. 1, 1991, pp. 3655-3659.
Tutt, et al., "Trispecific F(ab')3 derivatives that use cooperative signaling via the TCR/CD3 complex and CD2 to activate and redirect resting cytotoxic T cells", The Journal of Immunology, vol. 147, 1991, pp. 60-69.
Unz, "Aspects of Bioglocculation: An Overview", Flocculation in Biotechnology and Separation Systems, 1987, pp. 351-368.
Vaughan, et al., "Human Antibodies with Sub-nanomolar Affinities Isolated from a Large Non-immunized Phage Display Library", Nature Biotechnology, vol. 14, Mar. 1996, pp. 309-314.
Verhoeyen, et al., "Reshaping human antibodies: grafting an antilysozyme activity", Science, vol. 239, Mar. 25, 1988, pp. 1534-1536.
Waterhouse, et al., "Combinatorial infection and in vivo recombination: a strategy for making large phage antibody repertoires", Nucleic Acids Research, vol. 21, No. 9, 1993, pp. 2265-2266.
Westoby, et al., "Effects of solution environment on mammalian cell fermentation broth properties: Enhanced impurity removal and clarification performance", Biotechnology and Bioengineering, vol. 108, No. 1, Jan. 1, 2011, pp. 50-58.
Wickramasinghe, et al., "Clearance of minute virus of mice by flocculation and microfiltration", Biotechnology and Bioengineering, vol. 86, No. 6, Jun. 20, 2004, pp. 612-621.
Wickramasinghe, et al., "Enhanced microfiltration of yeast by flocculation", Desalination, vol. 147, No. 1-3, Sep. 10, 2002, pp. 25-30.
Yu, et al., "Selective Precipitation of Water-Soluble Proteins Using Designed Polyelectrolyte", Separation Science and Technology, vol. 37, No. 1, 2002, pp. 217-228.
Zapata, et al., "Engineering linear F(ab')2 fragments for efficient production in *Escherichia coli* and enhanced antiproliferative activity", Protein Engineering, vol. 8, No. 10, 1995, pp. 1057-1062.
Attia Yosry A., "Flocculation in biotechnology and separation systems", Process Technology Proceedings, 4, Proceedings of the International Symposium on Flocculation in Biotechnology and Separation Systems, vol. 8, No. 10, Jul. 28-Aug. 1, 1986, pp. 429 & 441.
Hourmant, et al., "Administration of an anti-CD11a monoclonal antibody in recipients of kidney transplantation. A pilot study", Transplantation, vol. 58, No. 3, 1994, pp. 377-380.
Hughes, et al., "The flocculation of bacteria using cationic synthetic flocculants and chitosan", Biotechnology Techniques, vol. 4, No. 1, 1990, pp. 55-60.
Izumrudov, et al., "Polycomplexes—potential for bioseparation", Bioseparation, vol. 7, No. 4-5, 1999, pp. 207-220.
Jakobovits, et al., "Analysis of homozygous mutant chimeric mice: Deletion of the immunoglobulin heavy-chain joining region blocks

(56) References Cited

OTHER PUBLICATIONS

B-cell development and antibody production", Proc. Natl. Acad. Sci. USA, vol. 90, Mar. 1993, pp. 2551-2555.

Jakobovits, et al., "Germ-line transmission and expression of a human-derived yeast artificial chromosome", Nature, vol. 362, Mar. 18, 1993, pp. 255-258.

Jones, et al., "Replacing the complementarity-determining regions in a human antibody with those from a mouse", Nature, vol. 321, May 29, 1986, pp. 522-525.

Jurcic, et al., "Radiolabeled Anti-CD33 Monoclonal Antibody M195 for Myeloid Leukemias", Cancer Research (Suppl.), vol. 55., Dec. 1, 1995, pp. 5908s-5910s.

Juweid, et al., "Treatment of Non-Hodgkin's lymphoma with radiolabeled murine, chimeric, or humanized LL2, an anti-CD22 monoclonal antibody", Cancer Research (Suppl.), vol. 55, Dec. 1, 1995, pp. 5899s-5907s.

Kamihira, et al., "Purification of recombinant protein A by aqueous two-phase extraction integrated with affinity precipitation", Biotechnology and Bioengineering, vol. 40, No. 11, Dec. 1992, pp. 1381-1387.

Kanazawa, et al., "Temperature-responsive liquid chromatography. 2. Effects of hydrophobic groups in N-isopropylacrylamide copolymer-modified silica", Anal Chem., vol. 69, No. 5, 1997, pp. 823-830.

Kanazawa, et al., "Temperature-responsive stationary phase utilizing a polymer of proline derivative for hydrophobic interaction chromatography using an aqueous mobile phase", Journal of Chromatography A, vol. 1106, Feb. 17, 2006, pp. 152-158.

Karim, et al., "Flocculation enhanced microfiltration of *Escherichia coli* lysate", Biochemical Engineering Journal, vol. 40, No. 3, Jul. 1, 2008, pp. 512-519.

Kim, et al., "Flocculation to enhance microfiltration", Journal of Membrane Science, vol. 182, No. 1-2, Feb. 15, 2001, pp. 161-172.

Kim, et al., "Removal of Cell and Cell Debris by Electrostatic Adsorption of Positively Charged Polymeric Particles", Flocculation in Biotechnology and Separation Systems, 1987, pp. 429-439.

Kim, et al., "The vascular endothelial growth factor proteins: identification of biologically relevant regions by neutralizing monoclonal antibodies", Growth Factors, vol. 7, 1992, pp. 53-64.

Kohler, et al., "Continuous cultures of fused cells secreting antibody of predefined specificity", Nature, vol. 256 (Attached version of document is reprinted with permission in The Journal of Immunology, 2005, vol. 174, pp. 2453-2455)., Aug. 7, 1975,pp. 495-497.

Kostelny, et al., "Formation of a bispecific antibody by the use of leucine zippers", The Journal of Immunology, vol. 148, No. 5, 1992, pp. 1547-1553.

Kozbor, et al., "A human hybrid myeloma for production of human monoclonal antibodies", The Journal of Immunology, vol. 133, No. 6, 1984, pp. 3001-3005.

Kumar, et al., Isolation and Purification of Proteins, edited by Rajni Hatti-Kaul et al.,2003, pp. 236-275.

Kumar, et al., "Affinity precipitation of α-amylase inhibitor from wheat meal by metal chelate affinity binding using Cu(II)-loaded copolymers of 1-vinylimidazole with N-isopropylacrylamide", Biotechnology and Bioengineering, vol. 59, No. 6, 1998, pp. 695-704.

Kumar, et al., "Smart Polymers: Physical forms and bioengineering applications", Prog. Polym. Sci., vol. 32, 2007, pp. 1205-1237.

Kumar, et al., "Type-Specific Separation of animal cells in an aqueous two-phase systems using antibody conjugates with temperature-sensitive polymers", Biotechnology and Bioengineering, vol. 75, No. 5, Dec. 5, 2001, pp. 570-580.

Ladisch, et al., "Scale-Up of Bioseparations for Microbial and Biochemical Technology", ACS Symposium Series, vol. 362, Chapter 7, 1988, pp. 72-101.

Laemmli, "Cleavage of structural proteins during the assembly of the head of bacteriophage T4", Nature, vol. 227, No. 5259, Aug. 15, 1970, pp. 680-685.

Larsson, et al., "Evaluation of affinity precipitation and a traditional affinity Chromatographic procedure for purification of soybean lectin, from extracts of soya flour", Journal of Biotechnology, vol. 49, No. 1-3, Aug. 20, 1996, pp. 189-199.

Li, et al., "Effect of molecular weight of poly(N-isopropyl acrylamide) temperature-sensitive flocculants on dewatering", AIChE Journal, vol. 55, No. 8, Aug. 2009, pp. 2070-2080.

Litton, et al., "Antibody-targeted superantigen therapy induces tumor-infiltrating lymphocytes, excessive cytokine production, and apoptosis in human colon carcinoma", European Journal of Immunology, vol. 26, No. 1, Jan. 1996, pp. 1-9.

Lorenz, et al., "In vivo blockade of TNF-alpha by intravenous infusion of a chimeric monoclonal TNF-alpha antibody in patients with rheumatoid arthritis. Short term cellular and molecular effects", The Journal of Immunology, vol. 156, No. 4, 1996, pp. 1646-1653.

Ma, et al., "Using precipitation by polyamines as an alternative to chromatographic separation in antibody purification processes", Journal of Chromatography B, vol. 878, No. 9-10, Mar. 15, 2010, pp. 798-806.

Maharjan, et al., "Novel chromatographic separation—The potential of smart polymers", Innovative Food Science and Emerging Technologies, 2007, pp. 1-11.

Majd, Gisela S., "The affinity precipitation for the isolation of biomolecules", Thèse EPFL, No. 3862, Aug. 2007, 146 pages.

Malmstadt, et al., "A Smart Microfluidic Affinity Chromatography Matrix Composed of Poly(N-isopropylacrylamide)-Coated Beads", Analytical Chemistry, vol. 75, No. 13., Jul. 1, 2003, pp. 2943-2949.

Malmstadt, et al., "Affinity Thermoprecipitation and Recovery of Biotinylated Biomolecules via a Mutual Streptavidin-Smart Polymer Conjugate", Bioconjugate Chem., vol. 14, No. 3, 2003, pp. 575-580.

Marks, et al., "By-passing immunization : Human antibodies from V-gene libraries displayed on phage", Journal of Molecular Biology, vol. 222, No. 3, Dec. 5, 1991, pp. 581-597.

Marks, et al "By—Passing Immunization: Building High Affinity Human Antibodies by Chain Shuffling", Nature Biotechnology, vol. 10, 1992, pp. 779-783.

McCafferty, et al., "Phage antibodies: filamentous phage displaying antibody variable domains", Nature, vol. 348, Dec. 6, 1990, pp. 552-554.

Millstein, et al., "Hybrid hybridomas and their use in immunohistochemistry", Nature, vol. 305, Oct. 6, 1983,pp. 537-540.

Morimoto, et al., "Single-step purification of F(ab').sub.2 fragments of mouse monoclonal antibodies (immunoglobulins G1) by hydrophobic interaction high performance liquid chromatography using TSKgel Phenyl-5PW", Journal of Biochemical and Biophysical Methods, vol. 24, 1992, pp. 107-117.

Morrison, et al., "Chimeric human antibody molecules: Mouse antigen-binding domains with human constant region domains", Proc. Nati. Acad. Sci. USA, vol. 81, Nov. 1984, pp. 6851-6855.

International Search Report received for PCT Application No. PCT/US2007/026040, mailed on Mar. 31, 2008, 1 page.

International Search Report received for PCT Application No. PCT/US2007/026090, mailed on Apr. 24, 2008, 1 page.

International Search Report received for PCT Application No. PCT/US2008/013736, mailed on Aug. 27, 2009, 5 pages.

International Search Report received for PCT Application No. PCT/US2009/006363, mailed on Feb. 18, 2010, 3 pages.

Peram, et al., "Monoclonal antibody purification using cationic polyelectrolytes: An alternative to column chromatography", Biotechnology Progress, vol. 26, No. 5, Sep./Oct. 2010, pp. 1322-1331.

Persson, et al., "Flocculation of Cell Debris for Improved Separation Centrifugation", Flocculation in Biotechnology and Separation Systems, 1987, pp. 457-466.

Presta, et al., "Humanization of an antibody directed against IgE", The Journal of Immunology, vol. 151, No. 5, 1993, pp. 2623-2632.

Presta, Leonard G., "Antibody engineering", Current Opinion in Structural Biology, vol. 2, No. 4, Aug. 1992,pp. 593-596.

Richman, et al., "Radioimmunotherapy for Breast Cancer Using Escalating Fractionated Doses of 131I-labeled Chimeric L6 Antibody with Peripheral Blood Progenitor Cell Transfusions", Cancer Research (Suppl.), vol. 55, Dec. 1, 1995, pp. 5916s-5920s.

Riechmann, et al., "Reshaping human antibodies for therapy", Nature, vol. 332, Mar. 24, 1988, pp. 323-327.

(56) References Cited

OTHER PUBLICATIONS

Riske, et al., "The use of chitosan as a flocculant in mammalian cell culture dramatically improves clarification throughput without adversely impacting monoclonal antibody recovery", Journal of Biotechnology, vol. 128, No. 4, Mar. 10, 2007, pp. 813-823.

"Merriam Webster Dictionary", available online at <http://www.merriam-webster.com/dictionary/associated>, retrieved on May 15, 2013, 4 pages.

"Ultrafiltration Discs and Stirred Cells" available online at <www.millipore.com/amicon>, Solvent-resistant Stirred Cells, p. 127.

Extended European Search Report received for EP Patent Application No. 09161982.5, mailed on Nov. 17, 2009, 6 pages.

International Preliminary Report on Patentability received for PCT Patent Application No. PCT/US2009/002787, issued on Dec. 13, 2010, 6 pages.

International Search Report and Written Opinion received for PCT Patent Application No. PCT/US2009/002787, mailed on Dec. 11, 2009, 9 pages.

International Preliminary Report on Patentability received for PCT Patent Application No. PCT/US2009/006363, mailed on Jun. 21, 2011, 6 pages.

International Search Report and Written Opinion received for PCT Patent Application No. PCT/US2009/067097, dated Jan. 29, 2010, 7 pages.

International Preliminary Report on Patentability & Written Opinion received for PCT Patent Application No. PCT/US2009/067097, mailed on Jun. 30, 2011, 7 pages.

International Preliminary Report on Patentability received for PCT Patent Application No. PCT/US2011/036648, mailed on Nov. 29, 2012, 9 pages.

International Preliminary Report on Patentability received for PCT Patent Application No. PCT/US2011/039595, mailed on Dec. 20, 2012, 10 pages.

STIMULUS RESPONSIVE POLYMERS FOR THE PURIFICATION OF BIOMOLECULES

PRIORITY DATA

The present application claims the benefit of priority of U.S. Provisional Patent Application No. 61/395,769, filed on May 17, 2010, the entire content of which is incorporated by reference herein in its entirety.

FIELD OF INVENTION

The present invention relates to polymers useful for protein purification. In particular, the present invention relates, at least in part, to stimulus responsive polymers useful for the purification of a target molecule from a sample containing the target molecule and one and more impurities.

BACKGROUND

Efficient and economic large scale purification of biomolecules such as, e.g., therapeutic proteins including antibodies, is an increasingly important consideration for the biotechnology and pharmaceutical industries. Generally, the purification processes are quite elaborate and expensive and include many different steps. For example, typically, in the case of proteins, proteins are produced using cell culture methods, e.g., using either mammalian or bacterial cell lines engineered to produce the protein of interest by insertion of a recombinant plasmid containing the gene encoding that protein. In general, following the expression of the target protein, its separation from one or more undesired components including, e.g., host cell proteins, media by-products and DNA, poses a formidable challenge. Such separation is especially important when the therapeutic proteins are meant for use in humans and have to be approved by the Food and Drug Administration (FDA).

In general, separation and/or purification processes that are currently being used for proteins, include at least the following steps: cell lysis to recover an intracellular protein or recovery of a protein from the media in case of a secreted protein; removal of cells and cellular debris using differential centrifugation or filtration to obtain a clarified sample containing the protein of interest; and use of a variety of chromatography media in a multi-step process to separate a protein of interest from the various impurities in the sample.

Various types of polymers, including polyelectrolytes, have been employed in one or more steps for the purification of biomolecules, especially proteins. For example, the use of polyelectrolytes in flocculation to purify proteins is well established (see, e.g., International PCT Patent Application No. WO2008/091740). This can be accomplished with a wide range of polymers, with the only required general characteristic being the polymer must have some level of interaction with a species of interest (e.g., a target molecule or an impurity). The most common methodology is the use of polymers containing ion species, such as polyelectrolytes. Generally, polyelectrolytes are added to the protein mixture and purification is achieved via selective flocculation of one or more components of the mixture. A critical drawback of this approach is that carefully controlled levels of polyelectrolytes have to be added in order to avoid residual polymer contamination (e.g., when polymer level too high) or inefficient flocculation (e.g., when polymer level too low). Because ion exchange and other charged chromatography media are commonly used in the purification of proteins, residual polyelectrolytes can potentially bind to the media used in downstream purification steps, thereby fouling and complicating the process.

Recently, technology has been developed which overcomes some of the challenges associated with the use of polymers for purification of biomolecules (see, e.g., International PCT Publication No. WO 2008/079302 A2). For example, stimulus-responsive or "Smart" polymers have been developed which can bind to both soluble (e.g., host cell proteins, DNA, cell culture additives) as well as insoluble (e.g., cells and cellular debris) components (see, e.g., US Publication Nos. 20080255027 and 20090036651). Although stimulus-responsive polymers show great promise in general, a key challenge that faces a broad use of such polymers is the existence of a simple stimulus which may be implemented at a variety of scales, ranging from laboratory scale to large production scale.

SUMMARY OF THE INVENTION

The present invention provides novel polyelectrolyte based stimulus responsive polymers which are easily scalable and operate over a wide range of pH and conductivity, thereby enabling their use in the purification of a wide array of biomolecules including, e.g., therapeutic proteins.

In some embodiments according to the present invention, a stimulus responsive polymer comprising a polyelectrolyte backbone comprising one or more hydrophobic groups is provided, where the polymer is capable of binding and precipitating a biomolecule of interest in a sample following the addition of a stimulus.

In some embodiments, the polyelectrolyte backbone of a polymer according to the present invention comprises at least two monomeric units or at least three monomeric units. In some embodiments, at least 50% of the monomeric units comprise a charge. In other embodiments, each monomeric unit of the polyelectrolyte backbone comprises a charge.

In some embodiments, a stimulus responsive polymer according to the present invention comprises a polyamine backbone. In some embodiments, one or more hydrophobic groups is a phenyl group.

The stimulus responsive polymers according to the present invention are useful for purifying a desired target molecule and do so by separating the desired target molecule from one or more undesirable entities present in a sample along with the desired target molecule.

Accordingly, in some embodiments, a stimulus responsive polymer according to the present invention binds and precipitates a biomolecule of interest, which itself is the desirable target molecule bound and precipitated by the stimulus responsive polymer. In other embodiments, a stimulus responsive polymer binds and precipitates a biomolecule of interest, which is an undesirable entity present in a sample along with the desirable target molecule.

In some embodiments, the biomolecule of interest is a therapeutic polypeptide (i.e., the desirable target molecule). In some embodiments, the therapeutic polypeptide is an antibody (e.g., a monoclonal antibody).

In other embodiments, the biomolecule of interest is selected from the group consisting of host cell protein, DNA, RNA, lipids, viruses, endotoxins, cell culture additives, whole cells and cellular debris.

In some embodiments, a polymer according to the present invention is responsive to a stimulus which is a complex forming salt.

Also encompassed by the present invention are methods of using the polymers described herein. The stimulus responsive polymers are unique and inventive over the polymers described in the prior art, in that they supplant or improve upon one or more steps in a purification process, thereby to substantially increase the overall purity of a target molecule desired to be purified or separated from one or more undesirable entities.

Accordingly, in some embodiments, a method of increasing the purity of a target molecule is provided, wherein the method comprises the steps of (a) providing a sample comprising a target molecule and one or more impurities; (b) contacting the sample with a stimulus responsive polymer comprising a polyelectrolyte backbone comprising one or more hydrophobic groups attached to the backbone under a first set of conditions suitable for the polymer to bind the target molecule in solution, thereby to form a complex of polymer and the target molecule; and (c) adding a stimulus to the sample under a second set of conditions suitable to precipitate the complex out of solution, where the precipitation of the complex results in the separation of the target molecule from one or more impurities, thereby to increase the purity of the target molecule.

In some embodiments according to the methods of the present invention, the method further comprises the step of recovering a target molecule from the complex.

In another embodiment, a stimulus responsive polymer according to the present invention binds and precipitates one or more impurities, instead of the target molecule, where the precipitation of a complex of the polymer and one or more impurities results in the separation of the target molecule from the one or more impurities, thereby to increase the purity of the target molecule. Accordingly, such a method comprises the steps of: (a) providing a sample comprising a target molecule and one or more impurities; (b) contacting the sample with a stimulus responsive polymer comprising a polyelectrolyte backbone comprising one or more hydrophobic groups attached to the backbone under a first set of conditions suitable for the polymer to bind the one or more impurities, thereby to form a complex of polymer and the one or more impurities; and (c) adding a stimulus to the sample under a second set of conditions suitable to precipitate the complex, where the precipitation of the complex results in the separation of the target molecule from one or more impurities, thereby to increase the purity of the target molecule.

In some embodiments, a stimulus responsive polymer according to the present invention comprises the following structure:

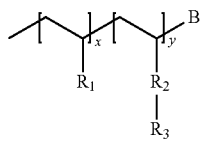

where x and y represent monomeric units of the polymer; $R_1$ and $R_2$ are charged groups which form a part of the polyelectrolyte backbone (B); and $R_3$ is a hydrophobic group attached to a charged group in the backbone. The ratio of y monomeric units (i.e., having a hydrophobic group attached to the backbone) to the total number of monomeric units (i.e., sum of x and y monomeric units) represents the "percent of hydrophobic modification" of the polymer.

In some embodiments, a stimulus responsive polymer according to the present invention comprises the following structure:

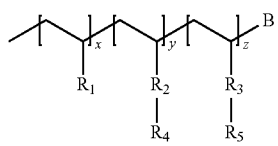

where x, y and z are monomeric units in the polymer; $R_1$, $R_2$ and $R_3$ are charged groups which form a part of the polyelectrolyte backbone (B); R4 is a hydrophobic group attached to a charged group in the backbone; and $R_5$ is a functional group attached to a charged group in the backbone. The ratio of y monomeric units (i.e., having hydrophobic group attached to backbone) to the total number of monomeric units in the polymer (i.e., sum of x, y and z monomeric units) represents the "percent hydrophobic modification" of the polymer. Further, the ratio of z monomeric units (i.e., having a functional group attached to a charged group on the backbone) to the total number of monomeric units (i.e., sum of x, y and z units) represents the "percent functional group modification" of the polymer.

In general, it is understood that a polymer encompassed by the present invention may have "n" number of any of monomeric units x, y or z, described herein, where n is equal or greater than two.

In still other embodiments, a stimulus responsive polymer according to the present invention comprises the following structure:

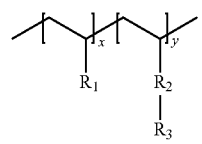

where x and y represent monomeric units; $R_1$, $R_2$ are aliphatic amine, groups (e.g., primary or secondary and/or aromatic amines) which form a part of a carbon containing backbone of a polyelectrolyte; and $R_3$ is a hydrophobic group attached to the amine group $R_2$ and contains 4 or more carbon atoms (e.g., an alkyl group, an alkenyl group, an aralkenyl group or a fluorocarbon group). In some embodiments, the ratio of y (i.e., monomeric units having a hydrophobic group attached to a charged group in the polyelectrolyte backbone) to x (i.e., unmodified charged group in the polyelectrolyte backbone) is 0.01 to 0.75 or 0.05 to 0.75. Accordingly, the percent hydrophobic group modification would be between 1% to 75% or between 5% to 75% of the total polyelectrolyte monomeric units (i.e., x+y).

in yet other embodiments, a stimulus responsive polymer according to the present invention comprises the following structure:

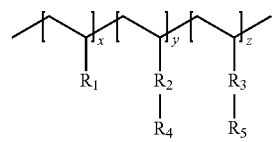

where $R_1$, $R_2$ and $R_3$ are aliphatic amine groups which form a part of the carbon containing polyelectrolyte backbone (e.g., primary or secondary amines and/or aromatic amines); $R_4$ is a hydrophobic group containing 4 or more carbon atoms and selected from alkenyl, aralkyl and aralkenyl groups; and $R_5$ is a hydrophobic group containing 4 or more 4 carbon atoms and selected from an alkyl or a fluorocarbon group. The ratio of y monomeric units to the total number of polyelectrolyte monomeric units is between 0.01 and 0.75. The ratio of z monomeric units to the total number of polyelectrolyte monomeric units is between 0.05 and 0.5 or between 0.01 and 0.5. Accordingly, the percent hydrophobic group modification is between 1% and 75% or between 5% and 75% and the percent functional group modification is between 1% and 50% or between 5% and 50%.

Additional methods of using the stimulus responsive polymers according to the present invention include methods which enable the purification of a target molecule or product of interest (e.g., an antibody) while minimizing the amount of residual polymer in the sample.

In some embodiments, a method of separating a target molecule (e.g., an antibody) from one or more impurities using a stimulus responsive polymer according to the present invention while minimizing residual amounts of polymer is provided, where the method comprises the steps of: (a) providing a sample comprising a target molecule and one or more impurities; (b) contacting the sample with a stimulus responsive polymer under a first set of conditions suitable for the polymer to bind the one or more impurities, thereby to form a first complex of polymer and one or more impurities, where the first set of conditions comprise adjusting pH or salt concentration of the sample before or after the addition of the polymer; (c) precipitating the first complex from the sample under a second set of conditions; (d) contacting the sample with a multivalent ion, thereby to form a second complex of residual polymer and multivalent ion; (e) precipitating the second complex; and (f) recovering the target molecule from the sample; thereby to separate the target molecule from one or more impurities in the sample while reducing the amount of residual polymer in the sample.

In some embodiments, the target molecule is an antibody. In a particular embodiment, the antibody is a monoclonal antibody.

In a particular embodiment, recovering the target molecule in various methods according to the present invention comprises a chromatography step. In another embodiment, recovering the target molecule comprises a filtration step.

In some embodiments, methods according to the present invention may include two or more steps which employ a stimulus responsive polymer according to the invention. For example, a stimulus responsive polymer may be used to precipitate one or more impurities in one step of the purification process and same or different polymer may be used to precipitate a target molecule or the desired product in a different step of the process.

In some embodiments, the one or more impurities is selected from the group consisting of host cell protein, DNA, RNA, antibody aggregates, viruses, endotoxins, whole cells, cellular debris and cell culture additives.

DETAILED DESCRIPTION

Figure 1:
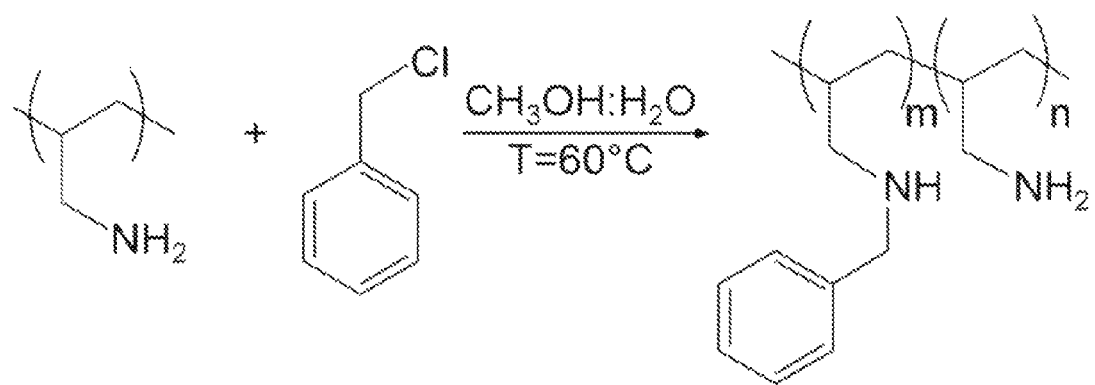
FIG. 1 is a schematic depicting the reaction of a polyallylamine polymer with benzylchloride

The present invention provides, at least in part, a novel and improved stimulus responsive polymer comprising a polyelectrolyte backbone modified with one or more hydrophobic groups, where the polymer solubility can be altered by the addition of a stimulus.

The stimulus responsive polymers and methods of using the same described herein are more efficient than those described in the prior art, in that, they provide an improved range of pH for purification of desired target molecules, including, e.g., proteins, as well as removal of undesirable entities such as impurities, e.g., host cell proteins, DNA, RNA, lipids, endotoxins, cell culture additives, cells and cellular debris. In some embodiments, the polymers described herein are responsive to low concentrations of simple multivalent salts, thereby allowing for improved scalability and reduced conductivity relative to existing salt responsive polymers. In various embodiments, the polymers according to the present invention can effectively remove whole cells, cellular debris as well as other soluble impurities from cell culture media. The polymers can also effectively remove impurities from protein mixtures containing a protein of interest and one or more impurities. Further, various polymers described herein are able to effectively capture target molecules and proteins/products of interest in a sample, thereby to separate them from one or more impurities present in the sample and increase the purity of the target molecule.

Also encompassed by the present invention are methods of using the polymers described herein for purification of target molecules, e.g., therapeutic proteins, using a wide array of conditions.

Without wishing to be bound by theory, it is contemplated that the stimulus responsive polymers described herein can be used for the binding and precipitation of either a desired target molecule, e.g., a therapeutic protein or a desirable product, or an undesired entity, e.g., one or more impurities including, e.g., host cell protein, DNA, RNA, lipids, endotoxins, cell culture additives, whole cells and cellular debris. In general, a molecule bound by a polymer according to the present invention is referred to as a biomolecule of interest, whether it is the desired target molecule or an undesired entity.

The selection of a particular stimulus responsive polymer to use, as described herein, is determined based on what the polymer is intended to bind. For example, in case of a biomolecule of interest which possesses a net negative charge at a pH above its pI (e.g., whole cells, cellular debris, DNA, endotoxins, and proteins), a stimulus responsive polymer comprising a polyelectrolyte backbone which is cationic (i.e., positively charged) is desirable to use. On the other hand, in case of a biomolecule of interest which comprises a net positive charge at a pH below its pI (e.g. proteins), a stimulus responsive polymer comprising a polyelectrolyte backbone which is anionic (i.e., negatively charged) is desirable to use.

A positive charge could be inherent to the polymer under conditions used during the purification process or, the positive charge can be generated with a change in pH which renders the stimulus responsive polymer charged.

An important parameter affecting the overall recovery of a biomolecule is the ratio of hydrophobic modification groups to the remaining unmodified charged groups in the polyelectrolyte backbone. For example, as the percentage of hydrophobic groups increases so does the resulting loss of the biomolecule through non-specific interactions. Therefore, for a given biomolecule, a specific ratio of charged groups to hydrophobic groups can be used in order to maximize biomolecule recovery. Additionally, a high percentage of hydrophobic groups may limit polymer solubility and the effectiveness of charged groups on the polyelectrolyte backbone.

Further, modification of a charged amine group in the backbone of the polyelectrolyte polyallylamine with benzyl chloride, results in a secondary amine which is charged under a wide array of pH conditions. However, such a benzyl modification adds a steric bulk to the amine group which can affect charge-charge interactions. Additionally, modification of a charged group in a polyelectrolyte backbone with a hydrophobic group can result in a reduction in the number of charged groups. For example, modification of an amine group of polyallylamine with benzyl chloride results in the formation of an amide linkage which is not a charged group, thereby resulting in a reduction in the number of charged groups in the backbone. Accordingly, a reduction in the number of charged groups can also affect both the polymer's solubility as well as the polymer's ability to bind through charge-charge interactions.

While, certain polymers according to the present invention are cationic and others are anionic, hybrid polymers may also be synthesized, which comprise a polyelectrolyte backbone which is cationic and modified with one or more hydrophobic as well as anionic groups. In case of such hybrid polymers, unmodified groups on the cationic polyelectrolyte are responsive to a complex forming salt, while the anionic modification groups on the backbone can bind a biomolecule of interest which possesses a net positive charge. Accordingly, the ratio of unmodified cationic groups in the polyelectrolyte backbone to anionic and hydrophobic groups is important to determine the solubility and stimulus necessary for the polymer to complex and capture the biomolecule of interest. For example, too few unmodified cationic groups in the polyelectrolyte backbone can result in limited to no response to stimulus. Whereas, too few anionic groups can limit the ability to capture a biomolecule of interest.

The requisite level of modification of polyelectrolyte backbone by hydrophobic groups as well as the type and amount of stimulus that is used can be determined based on the biomolecule of interest to be purified using the polymer as well as the conditions used, and the inherent solubility and molecular weight of the polymer backbone. For example, in order to minimize the amount of stimulus used, e.g., a multivalent salt, it is desirable to have more hydrophobic groups attached to the polyelectrolyte backbone. Alternatively, increased amount of multivalent ion stimulus reduces the extent of the hydrophobic modification or percent hydrophobic modification required. In some instances, it may be possible to completely eliminate the need for hydrophobic modification, for example, if the multivalent ion stimulus is at a very high concentration. Alternatively, increasing the polymer molecular weight reduces the inherent solubility of the polyelectrolyte backbone and may allow for low (5% or less) or no polyelectrolyte hydrophobic modification. However, the elimination of hydrophobic modification can increase the amount of residual polymer for lower molecular weight or more soluble polymer backbones at high polymer doses.

In various embodiments, the extent of hydrophobic modification on a polyelectrolyte backbone ranges from 1% to 85% or 5% to 50%. Accordingly, depending on the biomolecule of interest to be bound by a stimulus responsive polymer, the percentage of hydrophobic modification is at least 1%, 2%, 3%, 4%, 5%, 10%, 15%, 20%, 25%, 30%, 35%, 40%, 45%, 50%, 55%, 60%, 65%, 70%, 75%, 80% or 85%.

In some embodiments, a complex forming salt is used as a stimulus. In various embodiments, the concentration of the complex forming salt ranges from 2 mM to 500 mM, or from 25 mM to 100 mM. Exemplary complex forming salts include but are not limited to multivalent ions such as, e.g., citrate, phosphate, sulfate and EDTA, and ion-association salts such as perchlorate, dodecyl sulfate sodium salt, dodecyl benzene sulfate, Fe(II)-4-chloro-2-nitrophenol anion, tetraphenyl borate sodium salt and hexanitrodiphenol amine (see. e.g., ANALYTICAL SCIENCES, DECEMBER 1987, VOL. 3, p. 479). In general, an ordinary skill in the art would be familiar with numerous complex forming salts which are known in the art and may be used as a stimulus for the polymers described herein.

The amount of a complex forming salt which is required to induce precipitation depends on factors such as, e.g., pH, polymer concentration and concentration of biomolecule of interest in a sample. For example, some polyelectrolytes such as polyallylamine have a charge density which varies with pH (level of amine protonation). As the pH is increased, the level of charge density is reduced so the degree of stimulus required to induce precipitation will be different than at a lower pH or higher charge density state.

In general, a stimulus responsive polymer according to the present invention maybe added to a feedstock containing a target molecule or a target molecule containing sample, in the form of a solid or in the form of a liquid. The final polymer concentration is generally between 0.01% and 2%. In some methods described herein, a mixture of a polymer and a biomolecule of interest is generated followed by the addition of a stimulus, e.g., a complex forming salt such as a multivalent anion. The amount of stimulus may depend on the polymer concentration. For example, a polymer concentration of 2% will require a higher amount of stimulus required to induce polymer precipitation. It is important that the stimulus is applied in the correct or in a slight excess amount in order to ensure complete polymer precipitation through the stimulus response. This is in contrast to polymer flocculation, where overdosing leads to problematic residual polymer.

The present invention can be used in a variety of purification schemes. The stimulus responsive polymer can be beneficial at any step of the process, although the preferred use is at the beginning of the process during clarification or during capture of the target molecule. A single stimulus responsive polymer or mixture of polymers can be added in one or more steps and subsequently precipitated using one or more stimuli. The stimulus can be applied before, during or after the polymer associates with the biomolecule of interest (i.e., one or more impurities or a desired target molecule). Also, the stimulus can be applied before, during or after the removal of the precipitate, which is generally in solid form. The precipitate can be subsequently removed using one or more techniques known in the art and/or those described herein such as, e.g., filtration, settling, centrifugation or any other solid/liquid separation method or a combination of methods in simultaneous, parallel or series separation schemes.

Addition of the stimulus responsive polymer can be accomplished in several ways. The cell culture media may be adjusted to a desired condition prior to the addition of a stimulus responsive polymer, for example adjustment (e.g., reduction) of pH and/or conductivity. The stimulus responsive polymer can then be added to the cell culture media and mixed. The stimulus responsive polymer can be added in a liquid or a solid format. The polymer containing solution itself can be formulated just that it adjusts the pH of the cell culture media to a desired condition. For example, the stimulus responsive polymer can be dissolved in a concentrated acetic acid solution. The concentration of this acetic acid solution can be altered based on the volume, fermentation solution condition and protein concentration in order to provide the necessary pH adjustment upon addition of the stimulus responsive polymer, thereby to result in the desired polymer concentration and solution pH. The stimulus responsive polymer can be added in concentrations where spontaneous flocculation occurs, typically in the range of 0.01 to 0.1% wt polymer or 0.01 to 0.5% wt polymer, depending on the type and percent solids, such that the solution becomes cloudy and begins to form a precipitate. Alternatively, the stimulus responsive polymer can be added in concentrations where spontaneous flocculation does not occur but polymer-biomolecule association does occur, e.g., typically, in the range of 0.5% to 2% wt polymer, and the solution could be clear or slightly cloudy or more turbid than the original solution. Also, the stimulus responsive polymer can be added in concentrations where a mixture of spontaneous flocculation and polymer-biomolecule association occurs.

Although, use of a stimulus in a purification scheme is more desirable as it alleviates some of the problems associated with overdosing with the polymer, e.g., as in case of flocculation processes, it is contemplated that the polymers described herein may also be used as flocculants.

In an exemplary purification scheme, a stimulus responsive polymer according to the present invention is added to the cell culture after fermentation is complete and polymer is formulated to bind a biomolecule of interest which is not the desired target molecule. In such a method, a stimulus responsive polymer is added to the cell culture under a first set of conditions, e.g., conditions which may be adjusted before, during or after the addition of the polymer which binds the biomolecule of interest. After the stimulus responsive polymer is added under the first set of conditions, a stimulus is added under a second set of conditions, thereby generating a precipitate which includes the biomolecule of interest (e.g., one or more impurities such as cells, cellular debris, host cell proteins, DNA, endotoxins, and viruses). The solid precipitate can be subsequently removed by centrifugation and/or filtration, thereby resulting in a clarified cell culture fluid. The resulting clarified cell culture fluid may be subsequently passed through a capture step using a chromatography media to bind the desired target molecule. The target molecule may subsequently be eluted from the capture step. Accordingly, in some cases, by using a stimulus responsive polymer according to the present invention, which enables removal of one or more impurities at the clarification step, number of additional steps may be reduced/eliminated or modified.

In some embodiments, a stimulus responsive polymer is added to the cell culture under conditions where the polymer binds a biomolecule of interest, which is not the target molecule. After the stimulus responsive polymer is well mixed at the desired solution conditions, a flocculate which includes the biomolecule of interest is allowed to form. The solid containing the biomolecule of interest is removed by primary clarification. The resulting cell culture fluid is collected and a stimulus is applied to precipitate residual polymer. The precipitated residual polymer is subsequently removed by secondary clarification. The resulting clarified cell culture solution is passed through a capture step using a chromatography media to bind the target molecule. It may be possible to remove the residual polymer using the addition of a stimulus at any of the purification steps following primary clarification. Also, it may be possible to add a stimulus to remove residual polymer at any step or add one or more stimuli multiple times throughout the process.

In another purification scheme, a stimulus responsive polymer is added to the cell culture fluid after fermentation is complete under conditions suitable for the polymer to bind one or more impurities, such that the polymer does not bind the target molecule. After the stimulus responsive polymer is well mixed under the desired solution conditions, a stimulus is added which forms a solid precipitate with one or more impurities. The solid precipitate is removed by centrifugation and/or filtration. The resulting clarified cell culture solution is passed through a filter which is capable of binding the stimulus responsive polymer. One of ordinary skill in the art can readily select/identify a filter which can bind the stimulus responsive polymer. For example, a filter with similar properties to the biomolecule of interest which is to be bound by the polymer may be provided. Alternatively, a filter possessing a charged group that has the same charge as the biomolecule of interest and a charge opposite that of the stimulus responsive polymer may be used.

Membranes, packed beds or filters may also be used to remove a polymer from solution. For example, an anionic membrane containing sulfonic acid groups could be used to remove a polyamine stimulus responsive polymer. Also, a filter with binding properties similar to the stimulus used to precipitate the polymer can be used. If the stimulus is a multivalent anion, then providing a filter with a surface that contains multivalent anions can remove the polymer from solution. For example, a membrane modified with polyvinylphosphate could bind to polyamines in much the same way that phosphate ions can complex with polyamines, thereby to induce precipitation. Also, beads (e.g., polymethacrylate) modified with polyvinylphosphate could be used. In some embodiments, following filtration of the solution with a filter that can remove the stimulus responsive polymer, the resulting solution is passed through a capture step using a chromatography media to bind the target biomolecule. It is possible to remove the polymer using a chromatography media, depth filter or other porous material that can bind the stimulus responsive polymer. It is also possible to remove the polymer with adsorptive means at a single step or more than one or multiple steps. Further, it is possible to remove the polymer via adsorptive means at any step after the polymer's addition to the mixture.

It is anticipated that the present invention can be used in many variations of the purifications schemes described herein. The stimulus responsive polymer can be used to substitute or enhance both the clarification and capture steps. For example, two separate stimulus responsive polymers could be used; the first polymer which binds one or more impurities but does not bind the target molecule and a second polymer which binds the target molecule. These two polymers could be applied in separate steps or a single step. Likewise, a single polymer could be used which has functional groups capable of binding the target molecule and a polyelectrolyte backbone capable of binding one or more impurities. The single polymer could bind the target molecule and one or more impurities in a single step or multiple steps. Subsequent elution of the target molecule from the polymer may occur after several different precipitation/stimulus additions or washing steps. The stimulus responsive polymer can be added after the capture step and used to clarify suspended solids and impurities which result from virus inactivation or other steps after the capture step. The stimulus responsive polymer can also substitute for or enhance polishing steps.

In some embodiments, a virus inactivation step (i.e., exposure of solution to low pH, surfactants or heat) is included. The solution conditions may be adjusted and the sample processed through a series of polishing steps (i.e., one or more of ion exchange, hydrophobic interaction, mixed mode and others). The solution may then undergo a series of filtration steps, including virus filtration and ultrafiltration or diafiltration.

In order that the present disclosure may be more readily understood, certain terms are first defined. Additional definitions are set forth throughout the

DETAILED DESCRIPTION

I. Definitions

The term "stimulus" or "stimuli," as used interchangeably herein, is meant to refer to a physical or chemical change in the environment which results in a response by a stimulus responsive polymer according to the present invention. Accordingly, the present invention provides novel polymers which are responsive to a stimulus and which stimulus results in a change in the solubility of the polymer. Examples of stimuli to which one or more polymers described herein are responsive, include, but are not limited to, e.g., changes in temperature, changes in conductivity and/or changes in pH. In some embodiments, a stimulus comprises addition of a complexing agent or a complex forming salt to a sample. In various embodiments, a stimulus is generally added after the addition of a polymer to a sample. Although, the stimulus may also be added during or before addition of a polymer to a sample.

The term "polymer" as used herein, refers to a molecule formed by covalent linkage of two or more monomer units. These monomer units can be synthetic or occur in nature. The polymers formed by the repeating units can be linear or branched. Examples of polymers include, but are not limited to, polyethylene glycol, polypropylene glycol, polyethylene, polyallylamine, polyvinylalcohol, polystyrene and copolymers (e.g. polystyrene-co-polypyridine, polyacrylic acid-co-methyl methacrylate, pluronics, PF68 etc). In some embodiments according to the present invention, polymers comprise a polyelectrolyte backbone. Also described herein are copolymers, which may be used in the methods according to the present invention, where the copolymers are responsive to a stimulus. In general, it is understood that in case of polymers, the monomeric units are of the same type, whereas, a copolymer will usually have different types of monomeric units.

The term "stimulus responsive polymer," as used herein, is a polymer or copolymer which exhibits a change in a physical and/or chemical property after the addition of a stimulus. A typical stimulus response is a change in the polymer's solubility. For example, the polymer poly(N-isopropylacrylamide) is water soluble at temperatures below about 35° C., but become insoluble in water at temperatures of about 35° C. In a particular embodiment, a stimulus responsive polymer is a polyallylamine or a polyvinylamine polymer which is responsive to a multivalent ion stimulus (e.g, phosphate stimulus).

The term "polyelectrolyte backbone," as used herein, refers to a carbon containing polymer comprising two or more monomeric units, where at least 50% of the units, or at least 55% of the units, or at least 60% of the units, or at least 65% of the units, or at least 70% of the units, or at least 75% of the units, or at least 80% of the units, or at least 85% of the units, or at least 90% of the units, or at least 95% of the units, contain a charged functionality. In other words, at least 50% of the monomeric units include a charged group which forms a part of the unit. In some embodiments, a polyelectrolyte backbone described herein contains at least two or more monomeric units, where each of the units contains a charged functionality. In case of the polyelectrolyte backbone of polymers, in which each of the monomeric units contains a charged functionality, such polymers may be referred to as referred to as "continuous polyelectrolytes." Exemplary polyelectrolytes include, but are not limited to, polyallylamine, polyvinylamine, polyacrylic acid, polyethyleneimine, chitosan, and polyvinylphosphoric acid. It is also contemplated that one or more entities, which are different from the monomeric units, may be linked to polyelectrolyte backbone.

The term "hydrophobic group," as used herein, refers to a nonpolar entity or chemical group, which has little to no affinity for water. Exemplary hydrophobic groups include, but are not limited to, phenyl groups, tertiary butyl groups, cyclic hydrocarbons, polycyclic aliphatic hydrocarbons, polycyclic aromatic hydrocarbons, and short chain hydrocarbons such as hexyl and octyl groups. In a particular embodiment, the hydrophobic group is a phenyl group. The hydrophobic group can also be a non-hydrocarbon and contain heteroatoms such as nitrogen, oxygen, sulfur, phosphorus etc. In various embodiments according to the present invention, stimulus responsive polymers are provided, which comprise a polyelectrolyte backbone having one or more hydrophobic group attached to a charged group in the backbone. Without wishing to be bound by theory, it is understood that the number of hydrophobic groups attached to the polyelectrolyte backbone is important for altering the polymer solubility, thereby to improve the stimulus responsiveness of the polymer. However, it may be undesirable to have a number of hydrophobic groups which render the polymer water insoluble without a stimulus.

The percentage of charged groups in a polyelectrolyte backbone which are modified with a hydrophobic group is generally referred to as "percent hydrophobic modification" of the polymer. Accordingly, in various embodiments, the percent hydrophobic modification is important and ranges 1% to 85% or from 5% to 85%. Accordingly, the percent hydrophobic modification may be at least 1%, or at least 2%, or at least 3%, or at least 4% or at least 5%, or at least 6%, or at least 7%, or at least 8%, or at least 9%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%.

The term "percent hydrophobic modification" as used herein generally refers the ratio of unmodified polyelectrolyte charged groups to hydrophobic group modified polyelectrolyte charged groups as a percent of the total polyelectrolyte monomeric units in a polyelectrolyte polymer backbone.

In some embodiments, a hydrophobic group attached to a polyelectrolyte backbone further has a charged group attached to the hydrophobic group, which is distinct entity from the charged group in the backbone.

As used herein, the term "alkyl," generally refers to a straight or branched hydrocarbon chain. Straight chain or branched chain hydrocarbon chains refer to any substituted or unsubstituted acyclic carbon-containing compounds, including, e.g., alkanes, alkenes and alkynes. Examples of alkyl groups include lower alkyl, for example, methyl, ethyl, n-propyl, iso-propyl, n-butyl, iso-butyl, tert-butyl or iso-hexyl; upper alkyl, for example, n-heptyl, n-octyl, iso-octyl, nonyl, decyl, and the like; lower alkylene, for example, ethylene, propylene, propylyne, butylene, butadiene, pentene, n-hexene or iso-hexene; and upper alkylene, for example, n-heptene, n-octene, iso-octene, nonene, decene and the like. An ordinary skill in the art would be familiar with numerous straight, i.e., linear, as well as branched alkyl groups, which are encompassed by the present invention.

In addition, such alkyl groups may also contain various substituents in which one or more hydrogen atoms is replaced by a functional group. Examples of functional groups include but not limited to, carboxylic, sulfonic, phosphonic groups and the like. As used herein, the term "alkenyl" refers to a straight or branched hydrocarbon chain, whereat least one of the carbon-carbon linkages is a carbon-carbon double bond.

As used herein, the term "aralkyl" refers to an alkyl group which is terminally substituted with at least one aryl group.

As used herein, the term "aralkenyl" refers to an alkenyl group which is terminally substituted with at least one aryl group.

As used herein, the term "aryl" refers to a hydrocarbon ring bearing a system of conjugated double bonds, often comprising at least six n (pi) electrons. Examples of aryl groups include, but are not limited to, phenyl, naphthyl, anisyl, toluyl and xylenyl.

As used herein, the term "fluorocarbon" refers to a straight or branched carbon chain in which one or more hydrogen atoms is replaced by a fluorine group. Straight chain or branched chain fluorocarbon chain generally refers to any substituted or unsubstituted acyclic carbon-containing compound, including, e.g., alkanes, alkenes and alkynes. Examples of alkyl groups include lower alkyl, for example, methyl, ethyl, n-propyl, iso-propyl, n-butyl, iso-butyl, tert-butyl or iso-hexyl; upper alkyl, for example, n-heptyl, n-octyl, iso-octyl, nonyl, decyl, and the like; lower alkylene, for example, ethylene, propylene, propylyne, butylene, butadiene, pentene, n-hexene or iso-hexene; and upper alkylene, for example, n-heptene, n-octene, iso-octene, nonene, decene and the like. In general, it is understood that one or ordinary skill in the art would be familiar with numerous straight, i.e., linear, as well as branched alkyl groups, which are within the scope of the present invention. In addition, such alkyl groups may also contain various substituents in which one or more hydrogen or one or more fluorine atoms is replaced by a functional group. Examples of functional groups include, but are not limited to, carboxylic, sulfonic, phosphonic groups and the like.

The term "functional group," as used herein, is a group which imparts additional functionality to a polymer described herein. In other words, a functional group is a group, which is distinct from a hydrophobic group, and is also attached to the polyelectrolyte backbone, e.g., to a charged group in the backbone. For example, in some embodiments, a functional group can be a ligand for changing the binding properties of the polymer, for example, carboxylic acid, sulfonic acid, sulfate, primary amine, quaternary amine and diethylamino groups. The functional group can also alter properties or provide additional desired properties to the polymer such as, for example, altering a stimulus response or making the polymer responsive to a second stimulus. Exemplary functional groups for altering stimulus response behavior include, but are not limited to, carboxylic acid group (pH responsive), pyridine group (pH responsive) and N-isopropylacrylamido group (temperature response).

The term "ligand," as used herein, generally refers to an entity which provides a specific binding capability for another entity. Examples of "ligands" include, but are not limited to, ion exchange groups, bioaffinity or biospecific groups, hydrophobic groups, thiophilic interaction groups, chelate or chelating groups, groups having so called pi-pi interactions with target compounds, hydrogen bonding groups, and hydrophilic groups.

The term "flocculation," as used herein, refers to the addition of a flocculant, such as a polymer described herein, to a solution in order to remove one or more suspended insoluble or soluble impurities. The polymer must be added to the solution at a concentration which allows for spontaneous formation of insoluble aggregates which can be removed from solution via typical solid-liquid separation methods.

The term "composition," "solution" or "sample," as used herein, refers to a mixture of a target molecule or a desired product to be purified using one or more stimulus responsive polymers described herein along with one or more undesirable entities or impurities. In some embodiments, the sample comprises feedstock or cell culture media into which a target molecule or a desired product is secreted. In some embodiments, the sample comprises a target molecule (e.g., a therapeutic protein or an antibody) along with one or more impurities (e.g., host cell proteins, DNA, RNA, lipids, cell culture additives, cells and cellular debris). In some embodiments, the sample comprises a target molecule of interest which is secreted into the cell culture media. In some embodiments, a sample from which a target molecule is to be purified using one or more stimulus responsive polymers described herein is "partially purified" prior to contacting the sample with a stimulus responsive polymer. Partial purification may be accomplished, for example, by subjecting the sample to one or more purification steps, such as, e.g., one or more non-affinity chromatography steps. The target molecule may be separated from one or more undesirable entities or impurities either by precipitating the one or more impurities or by precipitating the target molecule.

In some embodiments, a stimulus responsive polymer according to the present invention binds to a biomolecule of interest which itself is a target molecule or product (e.g., a target protein or polypeptide), under a first set of conditions and precipitates the target molecule under a second set of conditions, e.g., upon the addition of a stimulus to the sample. In other embodiments, a biomolecule of interest is a molecule other than a target molecule. In other words, the biomolecule of interest bound by a stimulus responsive polymer described herein may be a molecule which is not desired to be associated with a target molecule in a sample. Without wishing to be bound by theory, it is contemplated that in some embodiments, a stimulus responsive polymer according to the present invention binds and precipitates one or more of host cell proteins, DNA, whole cells, cellular debris, viruses, endotoxins, and/or cell culture additives, upon the addition of a stimulus. Accordingly, a target molecule (e.g., a target protein or polypeptide) could be purified using a polymer described herein either by precipitating the desired target molecule or by precipitating one or more undesirable entities (e.g., one or more impurities) which may be present in a sample containing the desired target molecule.

The term "precipitate," precipitating" or "precipitation," as used herein, refers to the alteration of a bound (e.g., in a complex with a biomolecule of interest) or unbound polymer from an aqueous and/or soluble state to a non-aqueous and/or insoluble state.

The term "biomolecule of interest," as used herein, refers to any molecule which is bound and precipitated by a stimulus responsive polymer described herein. For example, the biomolecule of interest can be a desired target molecule such as, for example, a desired product or polypeptide of interest (e.g., an antibody), or it can be an undesirable entity, which needs to be removed from a sample containing the desired target molecule. Such undesirable entities include but are not limited to, for example, one or more impurities selected from host cell protein, DNA, RNA, protein aggregates, cell culture additives, viruses, endotoxins, whole cells and cellular debris.

The terms "target molecule," "target biomolecule," "desired target molecule" and "desired target biomolecule," as used interchangeable herein, generally refer to a polypeptide or product of interest, which is desired to be purified or separated from one or more undesirable entities, e.g., one or more impurities, which may be present in a sample containing the polypeptide or product of interest. The terms "protein of interest," "target polypeptide," "polypeptide of interest," and "target protein," as used interchangeably herein, generally refer to a therapeutic protein or polypeptide, including but not limited to, an antibody that is to be purified using a stimulus responsive polymer according to the present invention.

As used herein interchangeably, the term "polypeptide" or "protein," generally refers to peptides and proteins having more than about ten amino acids. In some embodiments, a stimulus responsive polymer described herein is used to separate a protein or polypeptide from one or more undesirable entities present in a sample along with the protein or polypeptide. In some embodiments, the one or more entities are one or more impurities which may be present in a sample along with the protein or polypeptide being purified. As discussed, above, in some embodiments, a stimulus responsive polymer described herein specifically binds and precipitates a protein or polypeptide of interest upon the addition of a stimulus to the sample. In other embodiments, a stimulus responsive polymer described herein binds to and precipitates an entity other than the protein or polypeptide of interest such as, for example, host cell proteins, DNA, viruses, whole cells, cellular debris and cell culture additives, upon the addition of a stimulus.

In some embodiments, a protein or polypeptide being purified using a stimulus responsive polymer described herein is a mammalian protein, e.g., a therapeutic protein or a protein which may be used in therapy. Exemplary proteins include, but are not limited to, for example, renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; Dnase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as α-FGF and β-FGF; epidermal growth factor (EGF); transforming growth factor (TGF) such as TGF-alpha and TGF-beta, including TGF-β1, TGF-β2, TGF-β3, TGFβ4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (Ils), e.g., IL-1 to IL-10; superoxide dismutase; T-cell receptors; surface membrane proteins; decay accelerating factor; viral antigen such as for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides.

Further, in some embodiments, a protein or polypeptide purified using a smart polymer according to the present invention is an antibody, functional fragment or variant thereof. In some embodiments, a protein of interest is a recombinant protein containing an Fc region of an immunoglobulin.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. Immunoglobulins or antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or a ligand such as a growth factor.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clarkson et al., Nature 352:624-628 (1991) and Marks et al., J. Mol. Biol. 222:581-597 (1991), for example.

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sc. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, $5^{th}$ Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In some embodiments, an antibody which is separated or purified using a stimulus responsive polymer according to the present invention is a therapeutic antibody. Exemplary therapeutic antibodies include, for example, trastuzumab (HERCEPTIN™, Genentech, Inc., Carter et al (1992) Proc. Natl. Acad. Sci. USA, 89:4285-4289; U.S. Pat. No. 5,725,856); anti-CD20 antibodies such as chimeric anti-CD20 "C2B8" U.S. Pat. No. 5,736,137); rituximab (RITUXAN™), ocrelizumab, a chimeric or humanized variant of the 21-17 antibody (U.S. Pat. No. 5,721,108; WO 04/056312) or tositumomab (BEXXAR™); anti-IL-8 (St John et at (1993) Chest, 103:932, and WO 95/23865); anti-VEGF antibodies including humanized and/or affinity matured anti-VEGF antibodies such as the humanized anti-VEGF antibody huA4.6.1 bevacizumab (AVASTAN™, Genentech, Inc., Kim et al (1992) Growth Factors 7:53-64, WO 96/30046, WO 98/45331); anti-PSCA antibodies (WO 01/40309); anti-CD40 antibodies, including S2C6 and humanized variants thereof (WO 00/75348); anti-CD11a (U.S. Pat. No. 5,622,700; WO 98/23761; Steppe et al (1991) Transplant Intl. 4:3-7; Hourmant et al (1994) Transplantation 58:377-380); anti-IgE (Presta et al (1993) J. Immunol. 151:2623-2632; WO 95/19181); anti-CD18 (U.S. Pat. No. 5,622,700; WO 97/26912); anti-IgE, including E25, E26 and E27 (U.S. Pat. No. 5,714,338; U.S. Pat. No. 5,091,313; WO 93/04173; U.S. Pat. No. 5,714,338); anti-Apo-2 receptor antibody (WO 98/51793); anti-TNF-alpha antibodies including cA2 (REMICADE™), CDP571 and MAK-195 (U.S. Pat. No. 5,672,347; Lorenz et al (1996) J. Immunol. 156(4):1646-1653; Dhainaut et al (1995) Crit. Care Med. 23(9):1461-1469); anti-Tissue Factor (TF) (EP 0 420 937 B1); anti-human alpha 4 beta 7 integrin (WO 98/06248); anti-EGFR, chimerized or humanized 225 antibody (WO 96/40210); anti-CD3 antibodies such as OKT3 (U.S. Pat. No. 4,515,893); anti-CD25 or anti-tac antibodies such as CHI-621 SIMULECT™ and ZENAPAX™ (U.S. Pat. No. 5,693,762); anti-CD4 antibodies such as the cM-7412 antibody (Choy et at (1996) Arthritis Rheum 39(1):52-56); anti-CD52 antibodies such as CAMPATH-1H (Riechmann et al (1988) Nature 332:323-337); anti-Fc receptor antibodies such as the M22 antibody directed against Fe gamma RI as in Graziano et al (1995) J. Immunol. 155(10):4996-5002; anti-carcinoembryonic antigen (CEA) antibodies such as hMN-14 (Sharkey et al (1995) Cancer Res. 55(23Suppl): 5935s-5945s; antibodies directed against breast epithelial cells including huBrE-3, hu-Mc 3 and CRL6 (Ceriani et al (1995) Cancer Res. 55(23): 5852s-5856s; and Richman et al (1995) Cancer Res. 55(23 Supp): 5916s-5920s); antibodies that bind to colon carcinoma cells such as C242 (Litton et al (1996) Eur J. Immunol. 26(1):1-9); anti-CD38 antibodies, e.g. AT 13/5 (Ellis et al (1995) J. Immunol. 155(2):925-937); anti-CD33 antibodies such as Hu M195 (Jurcic et al (1995) Cancer Res 55(23 Suppl):5908s-5910s and CMA-676 or CDP771: anti-CD22 antibodies such as LL2 or LymphoCide (Juweid et al (1995) Cancer Res 55(23 Suppl):5899s-5907s); anti-EpCAM antibodies such as 17-1A (PANOREX™); anti-GpIIb/IIIa antibodies such as abciximab or c7E3 Fab (REOPRO™); anti-RSV antibodies such as MEDI-493 (SYNAGIS™); anti-CMV antibodies such as PROTOVIR™); anti-HIV antibodies such as PRO542; anti-hepatitis antibodies such as the anti-Hep B antibody OSTAVIR™); anti-CA 125 antibody OvaRex; anti-idiotypic GD3 epitope antibody BEC2; anti-alpha v beta3 antibody VITAXIN™; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

The terms "contaminant," "impurity," and "debris," as used interchangeably herein, refer to any foreign or objectionable material, including a biological macromolecule such as a DNA, an RNA, one or more host cell proteins (HCPs or CHOPs), endotoxins, viruses, lipids and one or more additives which may be present in a sample containing a protein or polypeptide of interest (e.g., an antibody) being separated from one or more of the foreign or objectionable molecules using a stimulus responsive polymer according to the present invention. In some embodiments, a stimulus responsive polymer described herein binds and precipitates a protein or polypeptide of interest from a sample containing the protein or polypeptide of interest and one or more impurities. In other embodiments, a stimulus responsive polymer described herein binds and precipitates one or more impurities, thereby to separate the polypeptide or protein of interest from one or more impurities.

The terms "chinese hamster ovary cell protein" and "CHOP," as used interchangeably herein, refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid containing a protein or polypeptide of interest (e.g., an antibody or immunoadhesin expressed in a CHO cell). Generally, the amount of CHOP present in a mixture comprising a protein of interest provides a measure of the degree of purity for the protein of interest. Typically, the amount of CHOP in a protein mixture is expressed in parts per million relative to the amount of the protein of interest in the mixture.

It is understood that where the host cell is another mammalian cell type, an *E. coli*, a yeast cell, an insect cell, or a plant cell, HCP refers to the proteins, other than target protein, found in a lysate of the host cell.

The term "cell culture additive," as used herein, refers to a molecule (e.g., a non-protein additive), which is added to a cell culture process in order to facilitate or improve the cell culture or fermentation process. In some embodiments according to the present invention, a stimulus responsive polymer, as described herein, binds and precipitates one or more cell culture additives. Exemplary cell culture additives include anti-foam agents, antibiotics, dyes and nutrients.

The term "parts per million" or "ppm," as used interchangeably herein, refers to a measure of purity of a desired target molecule (e.g., a target protein or antibody) purified using a stimulus responsive polymer described herein. Accordingly, this measure can be used either to gauge the amount of a target molecule present after the purification process or to gauge the amount of an undesired entity. In some embodiments, the units "ppm" are used herein to refer to the amount of an impurity in a solution, e.g., HCP or CHOP, in nanograms/milliliter of protein of interest in milligrams/milliliter (i.e., CHOP ppm=(CHOP ng/ml)/(protein of interest mg/ml). When the proteins are dried (e.g., by lyophilization), ppm refers to (CHOP ng)/(protein of interest mg)).

The terms "isolating," "purifying" and "separating," are used interchangeably herein, in the context of purifying a target molecule (e.g., a polypeptide or protein of interest) from a composition or sample comprising the target molecule and one or more impurities, using a stimulus responsive polymer described herein. In some embodiments, the degree of purity of the target molecule in a sample is increased by removing (completely or partially) one or more impurities from the sample by using a stimulus responsive polymer, as described herein. In another embodiment, the degree of purity of the target molecule in a sample is increased by precipitating the target molecule away from one or more impurities in the sample.

In some embodiments, a purification process additionally employs one or more "chromatography steps." Typically, these steps may be carried out, if necessary, after the separation of a target molecule from one or more undesired entities using a stimulus responsive polymer according to the present invention.

In some embodiments, a "purification step" to isolate, separate or purify a polypeptide or protein of interest using a stimulus responsive polymer described herein, may be part of an overall purification process resulting in a "homogeneous" or "pure" composition or sample, which term is used herein to refer to a composition or sample comprising less than 100 ppm HCP in a composition comprising the protein of interest, alternatively less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm of HCP.

The term "clarification step," as used herein, generally refers to one or more initial steps in the purification of biomolecules. The clarification step generally comprises removal of cells and/or cellular debris using one or more steps including any of the following alone or various combinations thereof, e.g., centrifugation and depth filtration, precipitation, flocculation and settling. Clarification step generally involves the removal of one or more undesirable entities and is typically performed prior to a step involving capture of the desired target molecule. Another key aspect of clarification is the removal of soluble and insoluble components in a sample which may later on result in the fouling of a sterile filter in a purification process, thereby making the overall purification process more economical. In some embodiments, the present invention provides an improvement over the conventional clarification steps commonly used in various purification schemes, as demonstrated by reduced turbidity/impurities and higher throughput of downstream filters, described in the Examples herein.

The term "chromatography," as used herein, refers to any kind of technique which separates an analyte of interest (e.g., a target molecule) from other molecules present in a mixture. Usually, the analyte of interest is separated from other molecules as a result of differences in rates at which the individual molecules of the mixture migrate through a stationary medium under the influence of a moving phase, or in bind and elute processes.

The term "chromatography resin" or "chromatography media" are used interchangeably herein and refer to any kind of phase (e.g., a solid phase) which separates an analyte of interest (e.g., a target molecule) from other molecules present in a mixture. Usually, the analyte of interest is separated from other molecules as a result of differences in rates at which the individual molecules of the mixture migrate through a stationary solid phase under the influence of a moving phase, or in bind and elute processes. Examples of various types of chromatography media include, for example, cation exchange resins, affinity resins, anion exchange resins, anion exchange membranes, hydrophobic interaction resins and ion exchange monoliths.

The term "capture step" as used herein, generally refers to a method used for binding a target molecule with a stimulus responsive polymer or a chromatography resin, which results in a solid phase containing a precipitate of the target molecule and the polymer or resin. Typically, the target molecule is subsequently recovered using an elution step, which removes the target molecule from the solid phase, thereby resulting in the separation of the target molecule from one or more impurities. In various embodiments, the capture step can be conducted using a chromatography media, such as a resin, membrane or monolith, or a polymer, such as a stimulus responsive polymer, polyelectrolyte or polymer which binds the target molecule.

The term "salt," as used herein, refers to a compound formed by the interaction of an acid and a base. Various salts which may be used in various buffers employed in the methods described herein include, but are not limited to, acetate (e.g. sodium acetate), citrate (e.g., sodium citrate), chloride (e.g., sodium chloride), sulphate (e.g., sodium sulphate), or a potassium salt.

The term "multivalent salt" or "multivalent ion," as used interchangeably herein, refers to a compound which contains more than one charge or a charge containing group. In some embodiments, a multivalent salt is used as a stimulus which results in changing the solubility of a polymer responsive to the salt stimulus, usually resulting in precipitating the polymer out of solution. Exemplary multivalent salts which may be used include, for example, phosphate and sulfate. Also encompassed by the present invention are counter ions which may be used such as, for example, citrate. A multivalent salt, when used a stimulus as described herein, may be added as a stand alone reagent to a sample containing a biomolecule of interest along with a stimulus responsive polymer. Alternatively, the salt may be attached to a substrate, e.g., a membrane. In a particular embodiment, a membrane is modified with polyvinylphosphate, which is a multivalent salt containing polymer coating. A multivalent ion used as a stimulus, as described herein, is considered less detrimental to protein structure and stability, relative to other stimuli such as temperature and pH.

In some embodiments, multivalent salts are capable of interacting with one or more entities, thereby to form an associated species or complex. Accordingly, such salts may also be referred to as "complex forming salts." Non-limiting examples of complex forming salts and their resultant complexes are multivalent cations such as $Cu^{2+}$ and $Ca^{2+}$ and their complexes with the carboxylic acid groups found in ethylenediaminetetraacetate; multivalent anions such as phosphate ($PO_4^{3-}$) and citrate and their complexes with primary amines found in polyallylamine; and ion-associating salts such as perchlorate, dodecyl sulfate and dodecyl benzene sulfonate and their complexes with primary amines found in polyallylamine.

An "ion-associating salt" is a univalent (cation or anion), bulky and charge-dispersed salt. In some embodiments, an ion-associating salt is used as a stimulus which results in changing the solubility of a polymer responsive to the salt stimulus, thereby resulting in precipitating the polymer out of solution. Exemplary ion-associating salts which may be used include, for example, perchlorate, dodecyl sulfate, dodecyl benzene sulfonate, tetraphenyl borate and hexanitrodiphenol amine.

The term "solvent," as used herein, generally refers to a liquid substance capable of dissolving or dispersing one or more other substances to provide a solution. Solvents include aqueous and organic solvents, where useful organic solvents include a non-polar solvent, ethanol, methanol, isopropanol, acetonitrile, hexylene glycol, propylene glycol, and 2,2-thiodiglycol.

The term "pI" or "isoelectric point" of a polypeptide, as used interchangeably herein, refers to the pH at which the polypeptide's positive charge balances its negative charge. pI can be calculated from the net charge of the amino acid residues or sialic acid residues of attached carbohydrates of the polypeptide or can be determined by isoelectric focusing.

This invention is further illustrated by the following examples which should not be construed as limiting. The contents of all references, patents and published patent applications cited throughout this application, as well as the Figures, are incorporated herein by reference.

EXAMPLES

Example 1

Preparation of Unclarified Non-Expressing Cell Culture Fluid (CCF)

In a representative experiment, cells derived from a non-expressing Chinese Hamster Ovary (CHO) cell line were grown in a 10 L bioreactor (New Brunswick Scientific) to a density of $10 \times 10^6$ cells/mL and harvested at 64% viability. IgG was spiked to a concentration of 1.3 g/L. The level of host cell proteins (HCP) was found to be 8300 ng/mL using an ELISA (Cygnus #CM015). The pH of the unclarified cell culture was pH 7.2.

Example 2

Synthesis of a Stimulus Responsive Polymer Comprising a Polyelectrolyte Backbone Modified with a Hydrophobic Group In a representative experiment, a stimulus responsive polymer comprising a polyallylamine (BzMPAA) backbone modified with a hydrophobic group was synthesized. A polymer comprising a cationic polyelectrolyte backbone modified with a hydrophobic group was synthesized using a mixture of 10.3 g of 40% wt linear polyallylamine (NITTOBO, 150 kD), 2 g of lithium hydroxide and 20 mL of 50% water/methanol, which was stirred until well mixed. A solution of 2.1 mL of benzyl chloride in 15 mL of methanol was added to the polymer solution. The resulting mixture was heated at 60° C. for 14 hours. The benzyl modified polyallylamine was precipitated at the end of the reaction period as a result of thermodynamic incompatibility with the solvent. The precipitate was washed with 30 mL of acetone and redissolved in 400 mL of 1M acetic acid. The polymer was further purified by precipitation using 50 mM sodium phosphate at pH 7. FIG. 1 depicts a schematic of the reaction of the polyallylamine polyelectrolyte polymer with a hydrophobic group, i.e., benzylchloride.

Example 3

Preparation of a Solution of Benzyl Modified Polyallyamine (BzMPAA)

A 10% solution of BzMPAA was prepared by dissolving 10 g of the polymer from Example 2 in 90 g of 1M acetic acid with continuous agitation at room temperature for 16 hours. The resulting viscous solution was slightly hazy.

Example 4

Use of Different Concentrations of Benzyl Modified Polyallyamine (BxMPAA) in Clarification of a Non-Expressing Cell Culture Fluid (CCF)

BzMPAA from Example 3 was added in amounts of 0.2 g, 0.3 g, 0.4 g and 0.5 g to a 5 mL sample of the unclarified cell culture fluid (CCF) from Example 1. The samples were mixed at room temperature for 2 minutes. Since polymer addition reduced the pH to a range of pH 4.5 to 5.5, the pH of the mixtures were adjusted using 2M Tris base to a pH of 7. To the resulting solution, 0.043 g of potassium phosphate dibasic was added in order to precipitate the polymer-target molecule, cell and cell debris complex. The precipitate, in the form of a dispersed solid suspension was mixed continuously for five minutes. The precipitate was then collected via centrifugation (4000 rpm for 1 minute). The supernatant from each sample was then filtered through a 0.2 um Durapore® filter. The resulting purification is detailed in Table 1 below.

Example 5

Use of Different pH Values in the Clarification of Non-Expressing CCF with BzMPAA BzMPAA from Example 3 was added to four samples (0.4 g each) containing 5 mL of the unclarified cell culture fluid from Example 1. The samples were mixed at room temperature for 2 minutes. Since polymer addition reduced the pH to a range of pH 4.5 to 5.5, the pH of the mixtures were adjusted using 2M Tris base to pHs of 5.5, 6.5 7.5 and 8.5, respectively. To the resulting solution, 0.043 g of potassium phosphate dibasic was added in order to precipitate the polymer-target molecule, cell and cell debris complex. The precipitate, which was in the form of a dispersed solid suspension, was mixed continuously for five minutes. The precipitate was then collected via centrifugation (4000 rpm for 1 minute). The supernatant from each sample was then filtered through a 0.2 um Durapore® filter. The resulting purification is detailed in Table 1 below, which describes BzMPAA purification of spiked non-expressing CHO CCF.

TABLE 1

| Polymer Concentration (wt %) | Ph | IgG Recovery (%) | HCP Removal (%) | DNA Removal (LRV) |
|---|---|---|---|---|
| 0.4 | 7 | 97 | 63 | 2.7 |
| 0.6 | 7 | 92 | 82 | 2.8 |
| 0.8 | 7 | 86 | 83 | 2.7 |
| 1.0 | 7 | 82 | 85 | 2.7 |
| 0.8 | 5.5 | 95 | 83 | 3.0 |
| 0.8 | 6.5 | 86 | 91 | 2.9 |
| 0.8 | 7.5 | 90 | 86 | 2.8 |
| 0.8 | 8.5 | 95 | 62 | 2.9 |

Example 6

Assaying for the Purity Levels Resulting From the Use of BzMPAA in the Clarification of CCF Samples from Example 4 and Example 5 were assayed for IgG recovery using an affinity Protein A analytical HPLC assay. The level of IgG in solution was alternatively measured using an analytical Protein A column. Specifically, a Poros A/20 Protein A column (Applied Biosystems) was equilibrated with PBS, eluted with 0.1 M lysine (pH 2) and cleaned with 6M guanidine HCl. An IgG standard curve was created using a series of varying injection volumes of polyclonal IgG (Seracare). Samples were injected and IgG concentrations determined from the standard curve.

Samples from Example 4 and Example 5 were assayed for host cell proteins (HCP) using a commercial enzyme-linked immunosorbent assay (ELISA) kit (Cygnus Technologies Inc., Southport, N.C., Cygnus #CM015). Samples from Example 4 and Example 5 were also assayed for DNA using a standard pico green assay and Herring sperm DNA as a standard.

Example 7

Preparation of Unclarified Cell Culture Fluid (CCF)

Cells derived from an expressing Chinese Hamster Ovary (CHO-DG44) cell line were grown in a 10 L bioreactor (New Brunswick Scientific) to a density of 10×10$^6$ cells/mL and harvested at 30% viability. Monoclonal antibody (MAb) titer was determined to be 0.8 g/L. The level of host cell proteins (HCP) was found to be 200,000 ng/mL using an ELISA assay (Cygnus #3G ELISA). The pH of the unclarified cell culture was pH 6.9.

Example 8

Synthesis of 20% Benzyl Modified Polyallylamine (BzMPAA)

10 g of polyallylamine (PAA) (Nittobo, 150 kD; 40% wt./wt.) was placed in a 100 mL round bottom flask and a solution of 3.34 g of sodium hydroxide (1.2 Eq. per monomer) in 25 mL H$_2$O was added in small amounts at room temperature under magnetic stirring. The benzyl chloride (1.38 g, 1.25 mL) was then added at once, stirred for few minutes at room temperature then heated to 60° C. overnight for 17 hours. The reaction was cooled to room temperature and solvent was removed resulting in polymer precipitation. The precipitated polymer was washed with water and subsequently stirred in 1M aqueous AcOH solution (40 mL) until complete solubilization is achieved. The solution was then diluted with H$_2$O to a final volume of 400 mL (1% polymer solution), potassium dibasic phosphate (K$_2$HPO4) (3.48 g) was added under stirring and pH of the solution was adjusted to about 6.8 to precipitate the modified polymer. The polymer was collected by filtration over a fritted funnel and finally dried overnight in a vacuum oven overnight at 50-60° C.

Example 9

Synthesis of 40% Benzyl Modified Polyallylamine (BzMPAA)

10 g of polyallylamine (PAA) (Nittobo, 150 kD; 40% wt./wt.) was placed in a 100 mL round bottom flask and a solution of 3.34 g of sodium hydroxide (1.2 Eq. per monomer) in 25 mL H$_2$O was added at room temperature under magnetic stirring and in small amounts. Benzyl chloride (2.30 g, 2.09 mL) was then added, stirred for few minutes at room temperature and then heated to 60° C. overnight for 17 hours. The reaction was then cooled to room temperature and solvent is removed resulting in polymer precipitation. The precipitated polymer was washed with water and stirred in 1M aqueous AcOH solution (40 mL) until complete solubilization is achieved. The solution was then diluted with H$_2$O to a final volume of 400 mL (1% polymer solution), potassium dibasic phosphate (K$_2$HPO4) (3.48 g) is added under stirring and pH of the solution was adjusted to pH 6.8 to precipitate the modified polymer. The polymer was collected by filtration over a fritted funnel and finally dried overnight in a vacuum oven overnight at 50-60° C.

Example 10

Synthesis of 60% benzyl modified polyallylamine (BzMPAA)

10 g of polyallylamine (PAA) (NITTOBO, 150 kD; 40% wt./wt.) was placed in a 100 mL round bottom flask and a solution of 3.34 g of sodium hydroxide (1.2 Eq. per monomer) in 25 mL H$_2$O was added at room temperature under magnetic stirring and in small amounts. Benzyl chloride (3.23 g, 2.94 mL) was then added and stirred for few minutes at room temperature and subsequently heated to 60° C. overnight for 17 hours. The reaction was then cooled to room temperature and solvent was removed. The precipitated polymer was washed with water then stirred in 1M aqueous AcOH solution (40 mL) until complete solubilization is achieved. The solution was then diluted with H$_2$O to a final volume of 400 mL (1% polymer solution), potassium dibasic phosphate (K$_2$HPO4) (3.48 g) is added under stirring and pH of the solution was adjusted to pH 6.8 to precipitate the modified polymer. The polymer was collected by filtration over a fritted funnel and finally dried overnight in a vacuum oven overnight at 50-60° C.

Example 11

Synthesis of Diphenyl Modified Polyallylamine (DPhMPAA)

In an exemplary experiment, a polyelectrolyte polymer backbone, polyallylamine, was modified with a diphenyl group. Briefly, 10 g of polyallylamine (PAA) (Nittobo, 150 kD; 40% wt./wt.) was placed in a 100 mL round bottom flask and a solution of 3.34 g of sodium hydroxide (1.2 Eq. per monomer) in 25 mL H$_2$O is added at room temperature under magnetic stirring in small amounts. The chloro-diphenyl methane (3.68 g, 3.23 mL) was subsequently added, stirred for few minutes at room temperature then heated to 60° C. overnight for 17 hours. The reaction was subsequently allowed to cool to room temperature and the solvent was removed. The precipitated polymer was washed with water and stirred in 1M aqueous AcOH solution (40 mL). The remaining white solid, generated by hydrolysis of the diphenyl chloromethane, was filtered out. The solution was subsequently diluted with H$_2$O to a final volume of 400 mL (1% polymer solution), potassium dibasic phosphate (K$_2$HPO4) (3.48 g) was added under stirring and pH of the solution is adjusted to pH 6.8 to precipitate the modified polymer. The polymer was collected by filtration over a fritted funnel and finally dried overnight in a vacuum oven overnight at 50-60° C.

Example 12

Synthesis of 6% Dichlorobenzyl Modified Polyallylamine (DClBzMPAA)

In another experiment, 10 g of polyallylamine (PAA) (NITTOBO, 150 kD; 40% wt./wt.), was placed in a 100 mL round bottom flask and a solution of 3.34 g of sodium hydroxide (1.2 Eq. per monomer) in 25 mL of H$_2$O is added at room temperature under magnetic stirring and in small amounts. 3,4-Dichlorobenzyl chloride (1.71 g, 1.21 mL) was subsequently added and the mixture stirred at room temperature overnight for 17 hours. The reaction mixture was subsequently diluted with 100 ml of H$_2$O, after which pH is adjusted to neutral (pH 7.0) with phosphoric acid. The precipitated polymer was filtered out, washed with H₂O and dried in a vacuum oven overnight at 60° C. The polymer was collected by filtration over a fritted funnel and finally dried overnight in a vacuum oven overnight at 50-60° C.

Example 13

Synthesis of 10% Dichlorobenzyl Modified Polyallylamine (DClBzMPAA)

In another representative experiment, 10% dichlorobenzyl modified polyallylamine was synthesized as follows. 5 g polyallylamine (PAA) (NITTOBO, 150 kD; 40% wt./wt.) was placed in a 100 mL round bottom flask and a solution of 1.68 g of sodium hydroxide (1.2 Eq. per monomer) in 40 mL 50/50 H₂O/1,2 dimethoxyethane (DME) was added at room temperature under magnetic stirring and in small amounts. 3,4-dichlorobenzyl chloride (0.57 g, 0.40 mL) was subsequently added, stirred for few minutes at room temperature and then heated to 60° C. overnight for 21 hours. The reaction was subsequently allowed to cool to room temperature, DME was removed under vacuum at 60-70° C. and then the remaining solvent is removed. The precipitated polymer was washed with water and then stirred in 1M aqueous AcOH solution (20 mL) until complete solubilization is achieved. The solution was then diluted with H₂O to a final volume of 200 mL (1% polymer solution), potassium dibasic phosphate (K₂HPO4) (1.74 g) was added under stirring and pH of the solution was adjusted to pH 6.8 to precipitate the modified polymer. The polymer was collected by filtration over a fritted funnel and finally dried overnight in a vacuum oven at 50-60° C.

Example 14

Synthesis of 33% Chlorobenzyl Modified Polyallylamine (DClBzMPAA)

In another representative experiment, a 33% chlorobenzyl modified polyallylamine was synthesized as follows. 5 g polyallylamine (PAA) (NITTOBO, 150 kD, 40% wt./wt.) was placed in a 100 mL round bottom flask and a solution of 3.34 g of sodium hydroxide (1.2 Eq. per monomer) in 40 mL 50/50 H₂O/1,2 dimethoxyethane (DME) was added at room temperature under magnetic stirring and in small amounts. 4-chlorobenzyl chloride (1.48 g) was subsequently added, stirred for few minutes at room temperature and then heated to 60° C. overnight for 21 hours. The next day, DME was evaporated under vacuum at 60-70° C. and the remaining solvent was separated from the precipitated polymer. This latter was washed with water then stirred in 1M aqueous AcOH solution (20 mL) until complete solubilization is achieved. The solution was subsequently diluted with H₂O to a final volume of 200 mL (1% polymer solution), potassium dibasic phosphate (K₂HPO₄) (1.74 g) was added under stirring and pH of the solution is adjusted to pH 7 to precipitate the purified polymer. The polymer was collected by filtration over a fritted funnel and finally dried overnight in a vacuum at 50-60° C.

Example 15

Synthesis of 13% Phenyl-Benzyl Modified Polyallylamine (DClBzMPAA)

In another experiment 13% phenyl-benzyl modified polyallylamine was synthesized as follows. 4.7 g of polyallylamine (PAA) (Nittobo, 150 kD; 40% wt./wt.) was placed in a 100 mL round bottom flask and a solution of 3.34 g of sodium hydroxide (1.2 Eq. per monomer) in 40 mL 50/50 H₂O/1,2 dimethoxyethane (DME) was added at room temperature under magnetic stirring and in small amounts. 4-phenylbenzyl chloride (1 g) was then added and the mixture heated overnight at 55° C. for 20 hours. The reaction was subsequently allowed to cool to room temperature, DME was removed under vacuum at 60-70° C. and the remaining solvent was removed from the precipitated polymer. This latter was washed with water then stirred in 1M aqueous AcOH solution (40 mL) overnight to complete the solubilization. The solution was subsequently diluted with 1-170 to a final volume of 200 mL (1% polymer solution), potassium dibasic phosphate (K₂HPO₄) (1.74 g) was added under stirring and pH of the solution was adjusted to pH 7.0 in order to precipitate the purified polymer. The polymer was collected by filtration over a fritted funnel and finally dried overnight in a vacuum at 50-60° C.

Example 16

Synthesis of 27% Phenyl-Benzal Modified Polyallylamine (DClBzMPAA)

In another experiment, 27% phenyl-benzyl modified polyallylamine was synthesized as follows. 2.8 g polyallylamine (PAA) (Nittobo, 150 kD; 40% wt./wt.) was placed in a 100 mL round bottom flask and a solution of 3.34 g of sodium hydroxide (1.2 Eq. per monomer) in 24 mL 50/50 H₂O/1,2 dimethoxyethane (DME) was added at room temperature under magnetic stirring and in small amounts. 4-phenylbenzyl chloride (1 g) was subsequently added and the mixture was heated at 55° C. overnight for 20 hours. The reaction was subsequently allowed to cool to room temperature, DME was removed under vacuum at 60-70° C. and the remaining solvent was removed from the precipitated polymer. This latter was washed with water then stirred in 1M aqueous AcOH solution (32 mL) and stirred overnight to complete the solubilization. The solution was subsequently diluted with H₂O to a final volume of 200 mL (1% polymer solution), potassium dibasic phosphate (K₂HPO₄) (1.74 g) was added under stirring and pH of the solution was adjusted to pH 7.0 to precipitate the purified polymer. The polymer was collected by filtration over a fritted funnel and finally dried overnight in a vacuum at 50-60° C.

Example 17

Clarification of CCF with Different Polymer Concentrations

In an exemplary experiment, stimulus responsive polymers, described above in Examples 8-16, were evaluated for clarification of CCF, preparation of which is described above in Example 7. A polymer solution from Examples 8-16 was added in amounts of 0.2 g, 0.3 g, 0.4 g and 0.5 g to a 5 mL sample of the unclarified cell culture fluid. The samples were mixed at room temperature for 2 minutes. Since polymer addition reduced the pH to a range of pH 4.5 to 5.5, the pH of the mixtures were adjusted using 2M Tris base to a pH of 7. To the resulting solution, 0.043 g of potassium phosphate dibasic was added in order to precipitate the polymer-target molecule, cell and cell debris complex. The precipitate, in the form of a dispersed solid suspension, was mixed continuously for five minutes. The precipitate was then collected via centrifugation (4000 rpm for 1 minute). The supernatant from each sample was subsequently filtered through a 0.2 μm Durapore® filter. The resulting purification is detailed in Table 2.

Example 18

Clarification of CCF with Polymers at Different pH

In another experiment, a polymer solution from Examples 8-16 was added to four samples (0.4 g each) containing 5 mL of the unclarified cell culture fluid, as described in Example 7. The samples were mixed at room temperature for 2 minutes. Since polymer addition reduced the pH to a range of pH 4.5 to 5.5, the pH of the mixtures were adjusted using 2M Tris base to pHs of 5.5, 6.5 7.5 and 8.5, respectively. To the resulting solution, 0.043 g of potassium phosphate dibasic was added in order to precipitate the polymer-target molecule, cell and cell debris complex. The precipitate, in the form of a dispersed solid suspension, was mixed continuously for five minutes. The precipitate was then collected via centrifugation (4000 rpm for 1 minute). The supernatant from each sample was subsequently filtered through a 0.2 μm Durapore® filter. The resulting purification is described in Table 2.

Example 19

Clarification of CCF Using Polymers Responsive to Different Levels of Multivalent Ion Stimulus In another experiment, polymers described in Examples 8-15 were evaluated for the clarification of CCF, using different amounts of multivalent ion stimulus. Specifically, polymers from Examples 8-15 were added to four samples (0.4 g each) containing 5 mL of the unclarified cell culture fluid, described in Example 7. The samples were mixed at room temperature for 2 minutes. Since polymer addition reduced the pH to a range of pH 4.5 to 5.5, the pH of the mixtures were adjusted using 2M Tris base to pHs of 5.5, 6.5 7.5 and 8.5, respectively. To the resulting solution, a range from 0.031 to 0.043 g (50 to 70 mM final phosphate concentration) of potassium phosphate dibasic was added in order to precipitate the polymer-target molecule, cell and cell debris complexes. The precipitate, in the form of a dispersed solid suspension, was mixed continuously for five minutes. The precipitate was subsequently collected via centrifugation (4000 rpm for 1 minute). The supernatant from each sample was then filtered through a 0.2 μm Durapore® filter. The resulting purification is described in Table 2.

Example 20

Clarification of CCF Using a Commonly Used Flocculant

In another experiment, a commonly used flocculant, chitosan, was used for the clarification of CCF, in an attempt to generate comparative data. A polymer solution (2 wt %) was made according to the procedure describe in Riske, F. et. al.; Journal of Biotechnology, 128 (2007) 813-823. The polymer solution was added to CCF from Example 7 in varying amounts and at varying pH conditions. No stimulus was used with this polymer. The resulting purification is described in Table 2.

Example 21

Evaluation of Purity Levels Following Precipitation of CCF Using Stimulus Responsive Polymers In a representative experiment, polymers described in Examples 8-16 were assayed for IgG recovery using an affinity Protein A analytical HPLC assay. The level of IgG in solution was alternatively measured using an analytical Protein A column. A Poros A/20 Protein A column (Applied Biosystems) was equilibrated with PBS, eluted with 0.1 M lysine (pH 2) and cleaned with 6M guanidine HCl. An IgG standard curve was created using a series of varying injection volumes of polyclonal IgG (Seracare). Samples were injected and IgG concentrations determined from the standard curve. Samples from Examples 8-16 were assayed host cell proteins (HCP) using a commercial enzyme-linked immunosorbent assay (ELISA) kit (Cygnus Technologies Inc., Southport, N.C., Cygnus #3G). Samples from Examples 8-16 were assayed for DNA using a standard pico green assay and Herring sperm DNA as a standard. To assess the reduction of cells and cell debris, the turbidity was measured after centrifugation for 1 minute at 4000 rpm.

TABLE 2

Characterization Data for Examples 8-16 and 20.

| Example | Polymer Conc. (wt %) | Multivalent Salt Conc. (mM) | pH | Turbidity (NTU) | IgG Recovery (%) | HCP Removal (%) | DNA Removal (%) |
|---|---|---|---|---|---|---|---|
| 8 | 0.4 | 70 | 7.5 | 26.7 | 88 | 58 | 95 |
| 8 | 0.6 | 70 | 7.5 | 12.8 | 86 | 65 | 95 |
| 8 | 0.8 | 62 | 7.5 | 31.4 | 79 | 72 | 97 |
| 8 | 1.0 | 62 | 7.5 | 104 | 79 | 75 | 94 |
| 8 | 0.8 | 62 | 8.5 | 7.8 | 71 | 67 | 95 |
| 8 | 0.8 | 62 | 6.5 | 60.8 | 86 | 76 | 96 |
| 8 | 0.8 | 62 | 5.5 | 76.5 | 99 | 76 | 97 |
| 9 | 0.4 | 70 | 7.5 | 2.2 | 82 | 83 | 98 |
| 9 | 0.6 | 70 | 7.5 | 2.5 | 64 | 85 | >99 |
| 9 | 0.8 | 62 | 7.5 | 2.8 | 61 | 87 | >99 |
| 9 | 1.0 | 62 | 7.5 | 2.8 | 53 | 88 | >99 |
| 9 | 0.8 | 62 | 8.5 | 7.1 | 79 | 80 | >99 |
| 9 | 0.8 | 62 | 6.5 | 3.0 | 58 | 91 | 98 |
| 9 | 0.8 | 62 | 5.5 | 3.4 | 87 | 92 | 97 |
| 10 | 0.4 | 70 | 7.5 | 5.1 | 54 | 88 | 95 |
| 10 | 0.6 | 70 | 7.5 | 4.9 | 26 | 90 | 98 |
| 10 | 0.8 | 62 | 7.5 | 5.6 | 21 | 93 | >99 |
| 10 | 1.0 | 62 | 7.5 | 1.9 | 18 | 93 | >99 |
| 10 | 0.8 | 62 | 8.5 | 6.1 | 40 | 89 | >99 |

TABLE 2-continued

Characterization Data for Examples 8-16 and 20.

| Example | Polymer Conc. (wt %) | Multivalent Salt Conc. (mM) | pH | Turbidity (NTU) | IgG Recovery (%) | HCP Removal (%) | DNA Removal (%) |
|---|---|---|---|---|---|---|---|
| 10 | 0.8 | 62 | 6.5 | 5.0 | 14 | 96 | >99 |
| 10 | 0.8 | 62 | 5.5 | 2.8 | 26 | 95 | >99 |
| 11 | 0.4 | 70 | 7.5 | 124 | 97 | 42 | 98 |
| 11 | 0.6 | 70 | 7.5 | 210 | 61 | 52 | 98 |
| 11 | 0.8 | 62 | 7.5 | 478 | 92 | 56 | 99 |
| 11 | 1.0 | 62 | 7.5 | 474 | 84 | 55 | 98 |
| 11 | 0.8 | 62 | 8.5 | 94.2 | 54 | 65 | 98 |
| 11 | 0.8 | 62 | 6.5 | 380 | 88 | 60 | 97 |
| 11 | 0.8 | 62 | 5.5 | 212 | 99 | 58 | 97 |
| 12 | 0.6 | 70 | 7.5 | 3.4 | 50 | 74 | >99 |
| 12 | 0.8 | 62 | 7.5 | 1.9 | 85 | 58 | >99 |
| 12 | 1.0 | 62 | 7.5 | 1.3 | 70 | 66 | >99 |
| 12 | 0.8 | 62 | 8.5 | 1.4 | 33 | 81 | >99 |
| 12 | 0.8 | 62 | 6.5 | 1.0 | 37 | 93 | >99 |
| 12 | 0.8 | 62 | 5.5 | 1.4 | 93 | 77 | >99 |
| 12 | 0.6 | 50 | 7.5 | 1.7 | 81 | 85 | >99 |
| 12 | 0.6 | 50 | 6.5 | 3.1 | 87 | 80 | >99 |
| 12 | 0.4 | 50 | 5.5 | 1.6 | 98 | 66 | >99 |
| 13 | 0.4 | 70 | 7.5 | 2.3 | 86 | 71 | 98 |
| 13 | 0.6 | 70 | 7.5 | 1.9 | 71 | 73 | 98 |
| 13 | 0.8 | 62 | 7.5 | 2.4 | 81 | 77 | >99 |
| 13 | 1.0 | 62 | 7.5 | 1.4 | 68 | 80 | >99 |
| 13 | 0.8 | 62 | 8.5 | 1.5 | 60 | 69 | >99 |
| 13 | 0.8 | 62 | 6.5 | 1.1 | 77 | 87 | >99 |
| 13 | 0.8 | 62 | 5.5 | 1.3 | 98 | 90 | >99 |
| 13 | 0.6 | 50 | 7.5 | 1.7 | 78 | 84 | >99 |
| 13 | 0.6 | 50 | 6.5 | 3.1 | 39 | 84 | >99 |
| 13 | 0.4 | 50 | 5.5 | 1.6 | 69 | 78 | >99 |
| 14 | 0.4 | 70 | 7.5 | 5.4 | 69 | 91 | >99 |
| 14 | 0.6 | 70 | 7.5 | 7.3 | 46 | 89 | >99 |
| 14 | 0.8 | 62 | 7.5 | 5.1 | 57 | 94 | >99 |
| 14 | 1.0 | 62 | 7.5 | 4.3 | 22 | 87 | >99 |
| 14 | 0.8 | 62 | 8.5 | 2.8 | 41 | 92 | >99 |
| 14 | 0.8 | 62 | 6.5 | 3.7 | 2 | 97 | >99 |
| 14 | 0.8 | 62 | 5.5 | 8.5 | 7 | 94 | >99 |
| 14 | 0.6 | 50 | 7.5 | 7.5 | 44 | 89 | >99 |
| 14 | 0.6 | 50 | 6.5 | 6.5 | 57 | 96 | >99 |
| 14 | 0.4 | 50 | 5.5 | 6.6 | 43 | 90 | >99 |
| 15 | 0.4 | 70 | 7.5 | 3.0 | 93 | 75 | >99 |
| 15 | 0.6 | 70 | 7.5 | 1.5 | ~100 | 86 | >99 |
| 15 | 0.8 | 62 | 7.5 | 2.7 | 91 | 72 | >99 |
| 15 | 1.0 | 62 | 7.5 | 2.4 | 67 | 91 | >99 |
| 15 | 0.8 | 62 | 8.5 | 2.3 | ~100 | 77 | >99 |
| 15 | 0.8 | 62 | 6.5 | 1.4 | 57 | 87 | >99 |
| 15 | 0.8 | 62 | 5.5 | 2.0 | 89 | 90 | >99 |
| 15 | 0.6 | 50 | 7.5 | 5.3 | ~100 | 88 | >99 |
| 15 | 0.6 | 50 | 6.5 | 6.3 | ~100 | 70 | >99 |
| 15 | 0.4 | 50 | 5.5 | 7.9 | ~100 | 83 | >99 |
| 16 | 0.4 | 70 | 7.5 | 9.4 | 85 | 77 | >99 |
| 16 | 0.6 | 70 | 7.5 | 9.9 | 54 | 93 | >99 |
| 16 | 0.8 | 62 | 7.5 | 9.7 | ~100 | 85 | >99 |
| 16 | 1.0 | 62 | 7.5 | 19.0 | 67 | 94 | >99 |
| 16 | 0.8 | 62 | 8.5 | 9.1 | ~100 | 84 | >99 |
| 16 | 0.8 | 62 | 6.5 | 5.6 | 78 | 94 | >99 |
| 16 | 0.8 | 62 | 5.5 | 4.2 | 54 | 88 | >99 |
| 16 | 0.6 | 50 | 7.5 | 7.2 | 56 | 90 | >99 |
| 16 | 0.6 | 50 | 6.5 | 4.1 | 89 | 92 | >99 |
| 16 | 0.4 | 50 | 5.5 | 2.6 | 85 | 89 | >99 |
| 20 | 1 | 0 | 7.5 | 27.0 | ~100 | 39 | 30 |
| 20 | 0.8 | 0 | 8.5 | 22.0 | 61 | 63 | 54 |
| 20 | 0.8 | 0 | 6.5 | 16.0 | 70 | 30 | 34 |
| 20 | 0.8 | 0 | 5.5 | 195.0 | 63 | 62 | 96 |

Example 22

Synthesis of Benzyl Modified Polyethyleneimine (BzMPEI)

In another experiment, a benzyl modified polyethyleneimine stimulus responsive polymer was synthesized as follows. 10 g PEI (Aldrich, 750 kD; 50% wt./wt.) is placed in a 100 mL round bottom flask and a solution of ~3.34 g of sodium hydroxide (1.2 Eq. per monomer) in 25 mL $H_2O$ is added at room temperature under magnetic stirring and in small amounts. Benzyl chloride (2.30 g, 2.09 mL) is then added, stirred for few minutes at room temperature and then heated overnight at 60° C. for 17 hours. The reaction is then allowed to cool to room temperature and the solvent is removed. The precipitated polymer is washed with water then stirred in 1M aqueous AcOH solution (40 mL) until complete solubilization is achieved. The solution is subsequently diluted with H₂O to a final volume of 400 mL (1% polymer solution), potassium dibasic phosphate (K₂HPO4) (3.48 g) is added under stirring and pH of the solution is adjusted to pH 6.8 to precipitate the modified polymer. The polymer is collected by filtration over a fritted funnel and finally dried overnight in a vacuum oven at 50-60° C.

Example 23

Synthesis of Benzyl Modified Polyvinylamine (BzMPVA)

In a representative example, a benzyl modified polyvinylamine was synthesized as follows. 32 g of Poly(vinylamine) (PVA) hydrochloride (MW 83,500, Air Products and Chemicals Inc.) was weighed into a glass container. Add 200 mL H₂O and add 26 g 50% NaOH and stir until well mixed. Add 23.5 g benzyl chloride and mix at 70° C. for 16 hrs. A solid white mass separates from supernatant as the reaction progresses. Allow solid to settle and discard supernatant by decanting. Dissolve solid in 350 mL of 3% Acetic Acid overnight. Add 360 mL of H₂O and mix for 16 hrs until solution is homogenous. Dilute up to a 1% w/v solution by bringing the total volume up to 3.2 L with deionized (DI) H₂O. Add sodium phosphate to a concentration of 50 mM in order to initiate precipitation of the polymer. Add 1M NaOH to reach a pH of 6.8, providing additional polymer precipitation. Filter to dry cake and discard supernatant. Dry solid overnight at 70° C. Dissolve in 3% acetic acid until a homogenous solution is generated in order to make a 5% w/v solution.

Example 24

Comparison of Modified and Unmodified Polymer in Clarification in Presence of Stimulus Polyallyamine (PAA, Nittobo, 150 kD; 40% wt./wt.) and the polymer from Example. 10 (Bz-MPAA) were added to an aqueous solution to create a final polymer concentration of 0.2% wt and 0.4%, respectively. Potassium hydrogen phosphate was used as a stimulus and was added to the polymer solutions of PAA and Example 10 in varying amounts and the turbidity and nature of the aggregates formed was recorded. The results are shown in Table 3 below.

TABLE 3

| Polymer | Stimulus (mM Potassium Hydrogen Phosphate) | Turbidity (NTU) | Nature of Aggregate |
|---|---|---|---|
| PAA | 2.4 | 2.1 | Clear (No Agg) |
| PAA | 4.7 | 3 | Clear (No Agg) |
| PAA | 9.35 | 17.9 | Clear (No Agg) |
| PAA | 18.7 | 41.2 | Turbid |
| PAA | 37.5 | 152 | Turbid |
| PAA | 75 | 764 | Milky/Opaque |
| PAA | 150 | 760 | Milky/Opaque |
| Example 10 (BzMPAA) | 2.4 | 1 | Clear (No Agg) |
| Example 10 (BzMPAA) | 4.7 | 2 | Clear (No Agg) |
| Example 10 (BzMPAA) | 9.35 | 4 | Clear (No Agg) |
| Example 10 (BzMPAA) | 18.7 | 9 | Clear (No Agg) |
| Example 10 (BzMPAA) | 37.5 | 28 | Clear (No Agg) |
| Example 10 (BzMPAA) | 75 | 230 | Large Aggregates |
| Example 10 (BzMPAA) | 150 | 231 | Large Aggregates |

Example 25

Comparison of Modified and Unmodified Polymer in Clarification in Presence of a Stimulus Unmodified polymers polyallylamine (PAA, Nittobo, 150 kD; 40% wt./wt.), polyethyleneimine (PEI, Aldrich, 750 kD; 50% wt./wt.), polyvinyl amine (Poly(vinylamine) (PVA) hydrochloride, MW 83,500, Air Products and Chemicals Inc.) and the modified polymers from Examples 10 (Bz-MPAA), Example 22 (BzMPEI) and Example 23 (BzMPVA) were added to an aqueous solution to create a final polymer concentration of 0.2% and 0.4% by weight, respectively. Potassium hydrogen phosphate (150 mM) was used as a stimulus and was added to each of 0.4% polymer solutions and the turbidity and nature of the aggregates formed was recorded. The results are shown in Table 4.

TABLE 4

| Polymer | Stimulus (Potassium Hydrogen Phosphate) | Turbidity before Stimulus (NTU) | Turbidity after Stimulus (NTU) | Nature of Aggregate after Stimulus | Turbidity after Centrifuge (NTU) |
|---|---|---|---|---|---|
| PAA | 150 mM | 0.1 | >1000 | Milky | 348 |
| PEI | 150 mM | 2.9 | >1000 | Milky | >1000 |
| PVA | 150 mM | 0.5 | >1000 | Milky | 233 |
| Example 9 (BzMPAA) | 150 mM | 1.9 | >1000 | Large Aggregates | 9.6 |
| Example 18 (BzMPEI) | 150 mM | 5.1 | >1000 | Milky with Large Aggregates | 385 |
| Example 19 (BzMPVA) | 150 mM | 3.2 | >1000 | Large Aggregates | 12.7 |

Example 26

Synthesis of Hexanoic Acid and Tert-Butyl Modified Polyallyamine (HC-t-BuMPAA)

Figure 2:
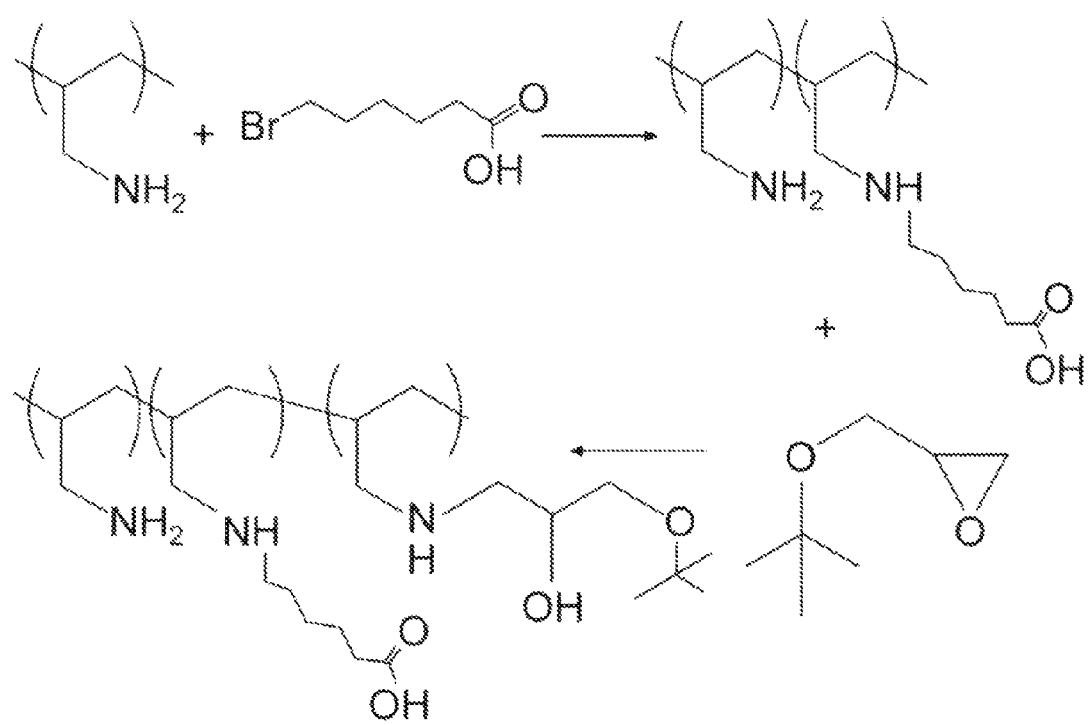
FIG. 2 depicts the reaction scheme for hexanoic acid and tert-butyl modified polyallylamine (HC-t-BuMPAA)

3.49 g of 6-bromohexanoic acid was dissolved in a solution comprising 10 ml of 40 wt % linear polymer poly(allylamine) (150 kda, NITTOBO) and 30 ml sodium hydroxide (1M). The mixture was reacted for 18 hrs at T=50° C. and the product was precipitated as a hydrated gel. The precipitate was dissolved in 100 mg/ml lithium hydroxide solution and mixed with 10 ml methanol containing 2.5 ml of tert-butyl glycidyl ether. The mixture was subsequently reacted for 18 hrs at T=50° C. The polymer solution was purified by extensive dialysis (3 days) against deionized (DI) water using 3.5 kda molecular weight cutoff dialysis tubing. The final concentration of the polymer solution was 7.2 wt %. A schematic of the synthesis reaction is shown below in FIG. 2.

Example 27

Figure 3:
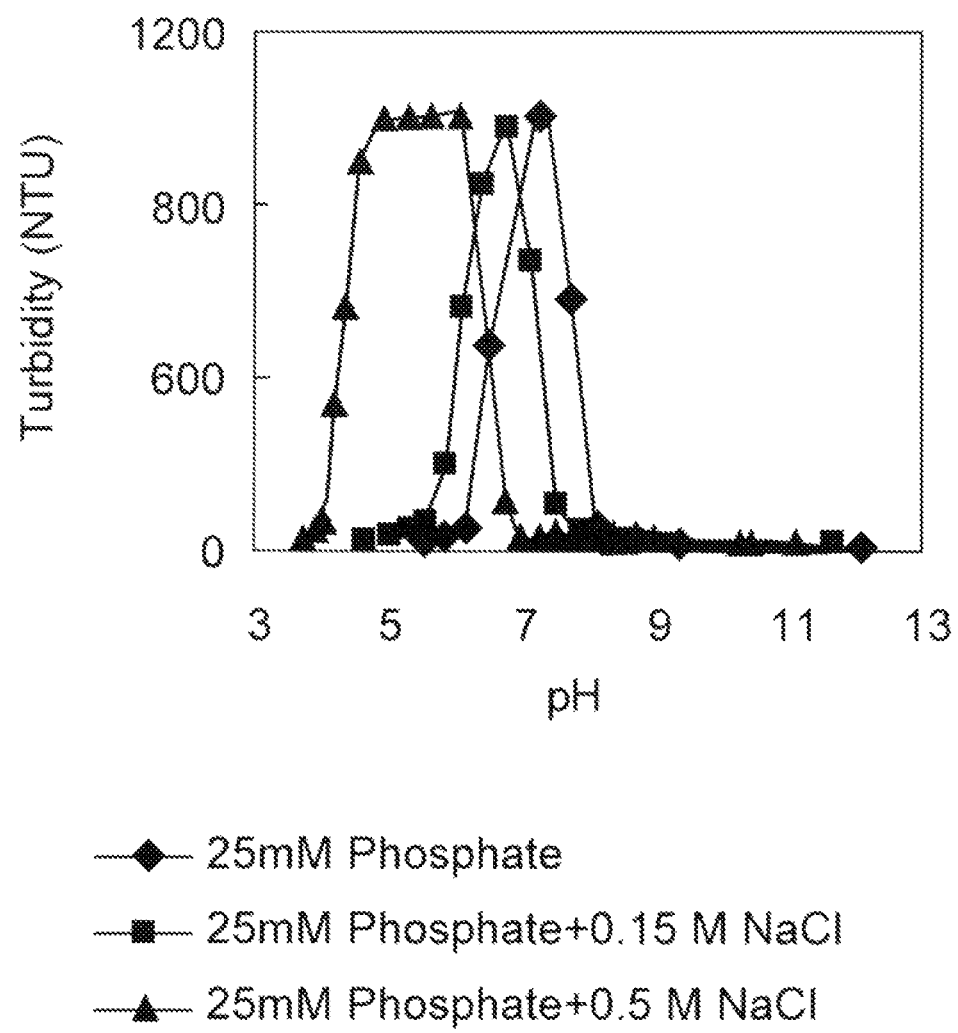
FIG. 3 is a graph depicting the effect of sodium chloride on the multivalent ion stimulus and pH responsiveness of hexanoic acid and tert-butyl modified polyallylamine (HC-t-BuMPAA). The X-axis depicts pH and Y-axis depicts turbidity of the centrate (i.e., output of a centrifuge).

Effect of Sodium Chloride on the Multivalent Stimulus of Hexanoic Acid and Tert-Butyl Modified Polyallylamine (HC-t-BuMPAA) when Dissolved in Tris Buffer 600 µl of HC-t-BuMPAA from Example 26 was added to 10 ml of 25 mM Sodium phosphate containing 0, 0.15 or 0.5 M sodium chloride. Final pH of the solution was 11.6. The solution was titrated with 3M acetic acid, and the turbidity of the solution was recorded after each addition. As depicted in FIG. 3, by adding sodium chloride in addition to sodium phosphate, a change in pH responsiveness, at which the phase transition occurs, was observed.

Example 28

Clarification of CCF Using the Polymer HC-t-BuMPAA at Different Polymer Concentrations In a representative experiment, unclarified CCF was clarified using a polymer according to the present invention as follows. 178, 356, or 534 µl of HC-t-BuMPAA from Example 26 was added to 5 ml of un-clarified cell culture fluid from Example 1 containing 25 mM sodium phosphate and adjusted to pH 8.7 using 25 µl of 3Macetic acid. After the addition of the polymer, final pH of the solution was titrated to 7.2 using 3M acetic acid, thereby precipitating the polymer-cells complex.

The precipitate, in the form of a dispersed solid suspension, was mixed continuously for another 5 min. The precipitate was then collected by centrifugation (4000 rpm for 1 min) and the supernatant was filtered through a 0.2 µm Durapore® filter. Regardless of the concentration of the polymer used, the process resulted in 100% Mab recovery.

Example 29

Synthesis of Polyvinylamine (PVA) Stimulus Responsive Polymer from Monomer

A stimulus responsive polymer comprised of repeat units containing primary amines was synthesized from a monomer as follows. 165 g of deionized water and 22.5 g of N-vinyl-formamide (NVF) (SIGMA-ALDRICH, 98%) was placed in a 250 mL round bottom flask. The flask was equipped with a magnetic stirrer and a $N_2$ dipstick. The solution was stirred and purged with $N_2$ for 0.5 hours followed by heating to 45° C. over an additional 0.5 hours with continuous purging. Initiator solution was prepared by adding 0.288 g of 2,2' Azobis(2-amidinopropane)dihydrochloride (ABAP) (Aldrich) to 10 mL of deionized water and dissolved. To the 250 mL round bottom flask the initiator solution was added under $N_2$ atmosphere. The solution was heated at 55° C. for 1 hour, followed by heating at 65° C. for 2 hours, further followed by heating at 75° C. for 1, hour with vigorous stirring under nitrogen. A viscous, homogenous solution was obtained and allowed to cool to room temperature. The viscosity was determined by Brookfield Viscosity DV-II+ Pro Visocometer (setting 100 RPM, 45% torque, spindle #34). The viscosity of the resulting solution was 278-350 centipoise (cP). The solution was transferred to a 500 mL flask and diluted with 330 mL of $H_2O$ and 40 g of 50% NaOH was added with stirring. The solution was heated at 85° C. for 8 hours.

A small sample was tested for sensitivity to a phosphate stimulus by adding a drop of 2 molar sodium phosphate to the hydrolyzed polymer and observing a white solid precipitate from the solution upon addition of the phosphate ion. To the hydrolyzed polymer solution, 25% HCl was added drop wise, until a pH of around 2 was reached. The solution was stirred vigorously overnight and a homogenous yellow solution was obtained. To that solution, 100 mL of 4 molar NaOH was added with stirring along with 500 mL isopropyl alcohol. The polymer was isolated by addition of 100 mL of 2 molar sodium phosphate and the solid was vacuum filtered and washed with deionized water. The solid polymer was dried over night in a vacuum oven at 65° C. The partially dry polymer was frozen with liquid nitrogen and ground to a fine powder and further dried in a vacuum oven at 65° C. for 24 hours. Finally, 40.7 g of a dry powder was recovered and dissolved in 1 molar acetic acid to a final concentration of 5% w/w.

Figure 4:
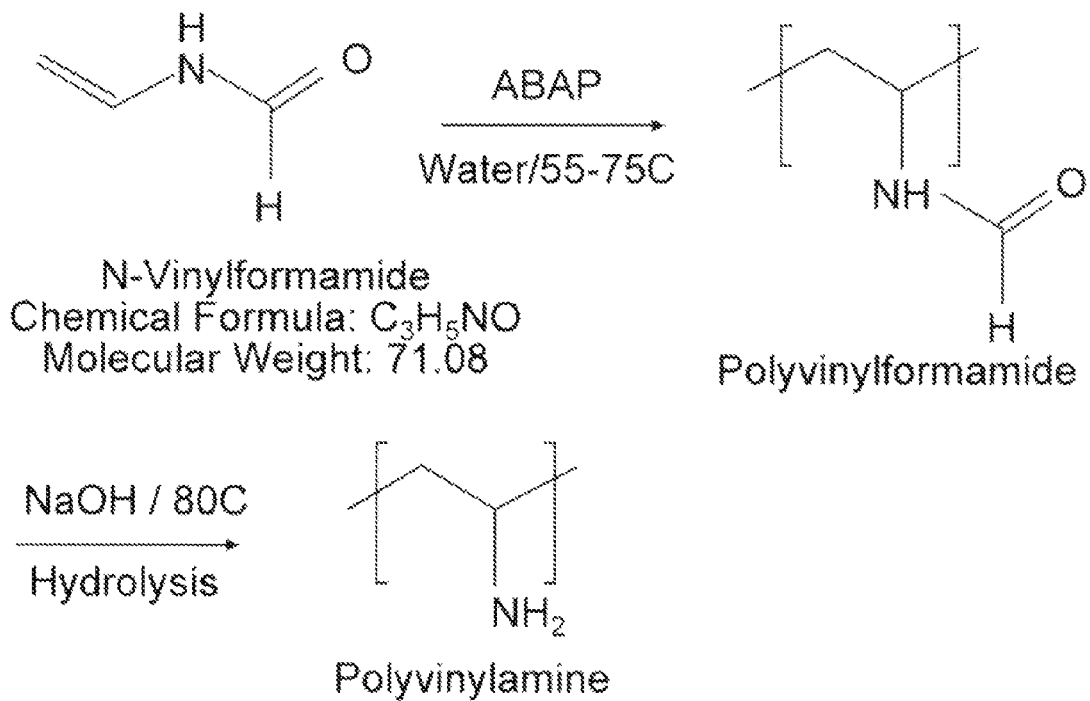
FIG. 4 depicts the synthesis of polyvinylamine, as described in Example 29.

An overview of the polyvinylamine synthesis process is depicted in FIG. 4.

Example 30

Synthesis of a Series of Hydrophobically Modified Polyvinylamine (PVA) Stimuli Responsive Polymers Using the PVA synthesized from Example 29, three separate hydrophobically modified stimuli responsive polymers were produced as follows. 100 mL of the 5% PVA solution from Example 29 was placed in each of three 500 mL glass jars and labeled jars 1, 2, and 3. To each of the three jars, 100 g of 4 molar NaOH was added with stirring. Next, 50 g of 1-propanol was added to each jar as a co-solvent and the solutions were stirred, followed by the addition of 0.74 g, 1.47 g, and 2.94 g of benzyl chloride to jars 1, 2, and 3, respectively. The three jars were heated at 60° C. for 16 hours. The resulting polymers were each isolated from the individual reaction solutions by bringing the volume of the reaction solution to 500 mL with deionized water, adjusting the pH to 8 with 25% HCl, and adding 100 g of 2 molar sodium phosphate. Upon addition of the phosphate ion, a solid precipitate was collected via vacuum filtration. The solid from each reaction was individually washed with deionized water and dissolved into 300 mL of 1 molar acetic acid. The polymer was further purified by adjusting the individual solutions to pH 7.4, precipitating the polymer with drop wise addition of 2 molar sodium phosphate, filtering the resulting solids, washing the solids with water, followed isopropyl alcohol, and drying in a vacuum oven at 65° C. for 2 days. Each sample of dried polymer was frozen with liquid nitrogen and ground to a fine powder. The mass of dried polymer recovered was 1.44, 2.12, and 2.47 g for jars 1, 2, and 3, respectively. The individual polymers were each dissolved to make a 2% solution in 1 molar acetic acid.

Example 31

Deprotection of Amines via Hydrolysis of a Very High Molecular Weight Poly(N-vinylacetamide) to Produce a Polyvinylamine (PVA) Stimuli Responsive Polymer In another exemplary experiment, a very high molecular weight stimulus responsive polymer was prepared as follows. Very high molecular weight polymer generally refers to a polymer having a molecular weight equal or greater than 1000 KDa.

A stimuli responsive polymer comprised of repeat units containing primary amines was prepared as follows. In a 2 liter glass jar 40 g of poly(N-vinylacetamide)-linear homopolymer (POLYSCIENCES, INC.) with an average molecular weight of 4,060 kDa was dissolved into 0.8 liter of deionized water by vigorous stirring for 16 hours. To this solution, 140 g concentrated HCl was added with continuous stirring over 1 hour. The jar was lightly capped and the solution was heated to 99° C. for 5 days with intermittent rotation to mix the solution. After 5 days of heating, the solution was allowed to cool to room temperature and the total volume was adjusted to 4 liters with deionized water. The solution was adjusted to pH 7 with 8 molar NaOH with vigorous stirring. The hydrolyzed product was precipitated with drop wise addition of 2 molar sodium phosphate until no further precipitate was observed. The white precipitate was washed with deionized water and pressed to remove excess water. The recovered polymer was dried in a vacuum oven at 65° C. for 2 days. The dried polymer was frozen with liquid nitrogen and ground to a fine powder. The recovered dry mass was 42.5 g. A 2% solution was made by dissolving the dried powder into 1 molar acetic acid and 0.08% HCl. The resulting solution was compared to a 2% solution of starting material (poly(N-vinylacetamide)-linear homopolymer) for response to a phosphate or citrate stimuli. This was performed by drop wise addition of 2 molar sodium phosphate or 0.2 molar sodium citrate to 50 ml samples of both the starting material and the resulting hydrolyzed polymer.

The resulting hydrolyzed polymer precipitated to a white mass with the addition of phosphate or citrate ions while the solution of starting material had no precipitate upon drop wise addition of phosphate or citrate ions, thereby indicating that the starting material is not responsive to a stimulus (e.g., a multivalent anion such as phosphate or citrate), while the very high molecular weight polymer synthesized, as described in this Example, is responsive to a stimulus (e.g., a multivalent anion such as phosphate or citrate).

Figure 5:
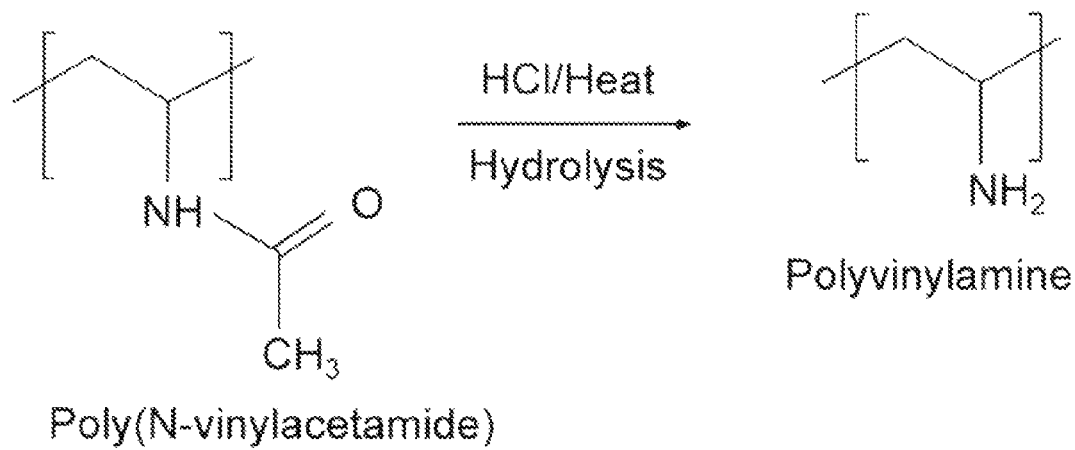
FIG. 5 depicts a reaction for the deprotection of polyamine after polymerization.

FIG. 5 depicts a process for deprotection of polyamine polymer, thereby resulting in the formation of a stimulus responsive Polyvinylamine (PVA).

Example 32

Synthesis of a Hydrophobically Modified Polyvinylamine (PVA) Stimuli Responsive Polymer Based on a Deprotected Poly(N-vinylacetamide)

Using the PVA obtained from deprotected 4,060 kDa poly (N-vinylacetamide)-linear homopolymer from Example 31 a very high molecular weight hydrophobically modified stimuli responsive polymer was prepared as follows.

100 g of a 2% solution of deprotected 4,060 kDa poly(N-vinylacetamide) was placed in a glass jar. To the glass jar, 100 g of 4 molar NaOH was added to adjust to pH to approximately 13. Next, 20 g of 1-propanol was added to the jar as a co-solvent. Finally, 0.58 g of benzyl chloride was added and the jar was capped. The reaction was heated at 60° C. for 3 hours with vigorous shaking. After 3 hours, the reaction mixture was cooled to room temperature and the product was precipitated with acetone and subsequently collected. The resulting solids were washed with deionized water, followed by isopropyl alcohol, and were dried in a vacuum oven at 65° C. for 2 days. The dry solids were ground to a fine powder and the final dry mass of polymer collected was 1.44 g. A 2% solution was made by dissolving the dried powder into 1 molar acetic acid and 0.08% HCl. The resulting solution was tested for sensitivity to a multivalent ion stimulus by drop wise addition of 2 molar sodium phosphate or 0.2 molar sodium citrate to 5 mL samples of 0.5% polymer solutions. Upon addition of the phosphate or citrate ions a white precipitate is observed, thereby indicating that the polymer was responsive to a multivalent anion stimulus.

Figure 6:
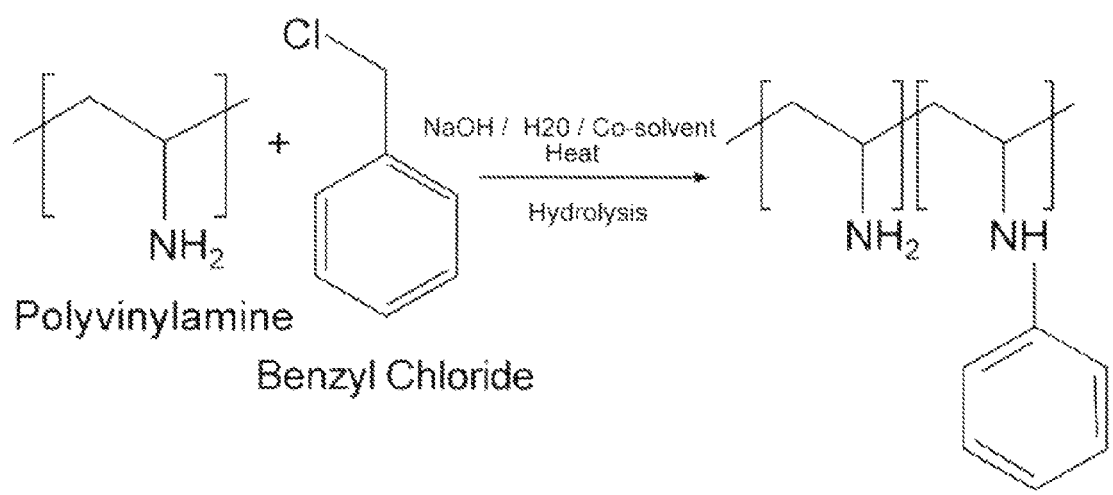
FIG. 6 depicts a reaction of polyvinylamine with benzylchloride.

FIG. 6 provides a schematic of the synthesis process described in this Example.

Example 33

Synthesis of a Stimulus Responsive Vinylamine/Vinylbutylether Copolymer (VA-co-VBE)

In another experiment, a stimulus responsive copolymer was prepared, which had one of the monomeric units included a hydrophobic group.

A stimulus responsive polymer comprised of repeat units containing primary amines and butylether was synthesized from monomers as follows. 90 g of octane, 2.5 g of Span-85 (SIGMA), 16 g of N-vinylformamide (NVF)(ALDRICH, 98%), 5 g of N-butylvinylether (SIGMA), and 30 g of deionized water was placed in a 250 mL round bottom flask. The flask was equipped with a magnetic stirrer and a $N_2$ dipstick. The solution was stirred and purged with $N_2$ for 1 hour as the temperature was increased to 55° C.

Initiator solution was prepared by adding 0.10 g of 2,2' Azobis(2-amidinopropane)dihydrochloride (ABAP) (ALDRICH) to 10 mL of deionized water and dissolved. The initiator solution was charged to the 250 mL round bottom flask containing the reaction solution under nitrogen purged atmosphere. The solution was heated at 55° C. for 1 hour, followed by heating at 60° C. for 1 hour, further followed by heating at 70° C., for 1 hour and followed by heating at 80° C. for 1 hour, with vigorous stirring with continuous nitrogen purging. This resulted in a two phase solution with a viscous gel layer on the bottom. The top layer was decanted and discarded. To the bottom layer, 200 mL of deionized water was added and 20 g of 50% NaOH was added with vigorous stirring. The solution was heated at 80° C. for 6 hours. After 6 hours, the solution was removed from heat and allowed to cool to room temperature. The volume was increased to 2 L with deionized water. The product was isolated by dropwise addition of 2 molar sodium phosphate, resulting in a large white precipitate. The precipitate was collected by decanting the supernatant and the precipitate was washed with deionized water. The isolated polymer was dissolved in 500 mL deionized water, 10 g acetic acid, and 2 g concentrated HCl. The resulting solution was tested for sensitivity to a multivalent ion stimulus by drop wise addition of 2 molar sodium phosphate or 0.2 molar sodium citrate to 5 mL samples of 0.5% polymer solutions. Upon addition of the phosphate or citrate ions a white precipitate was observed, thereby indicating that the polymer was responsive to a multivalent anion stimulus.

Figure 7:
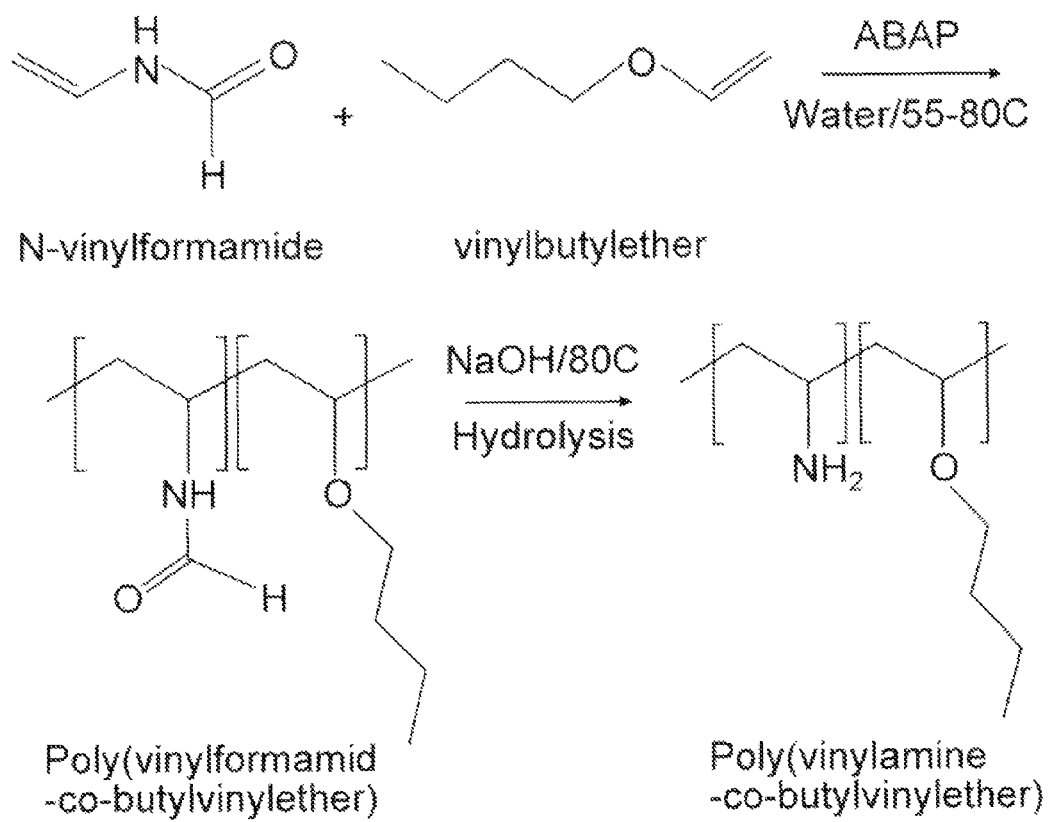
FIG. 7 depicts a polymerization and reaction scheme to form a multivalent ion stimulus responsive copolymer.

FIG. 7 depicts a schematic of the reaction described in this Example. This example demonstrates that copolymers containing an amine or charged functionality copolymerized with a hydrophobic monomer are responsive to a multivalent ion stimulus.

Example 34

Synthesis of Very High Molecular Weight Polyvinylamine (PVA) Stimulus Responsive Polymer from NVF Monomer via Inverse Emulsion Polymerization A stimulus responsive polymer comprised of repeat units containing primary amines was synthesized from a monomer as follows. 90 g of octane, 2.5 g of Span-85 (SIGMA), 16 g of N-vinylformamide (NVF)(ALDRICH, 98%), and 30 g of deionized water was placed in a 250 mL round bottom flask. The flask was equipped with a magnetic stirrer and a $N_2$ dipstick. The solution was stirred and purged with $N_2$ for 1 hour as the temperature was increased to 55° C. Initiator solution was prepared by adding 0.20 g of 2,2' Azobis(2-amidinopropane)dihydrochloride (ABAP) (ALDRICH) to 20 mL of deionized water and dissolving. The initiator solution was charged to the 250 mL round bottom flask containing the reaction solution under nitrogen purged atmosphere. The solution was heated to 60° C. for 2 hours, followed by heating to 75° C. for 1 hour with vigorous stirring with continuous nitrogen purging. A two phase solution results with a viscose gel layer on the bottom. The lop layer is decanted and discarded. To the bottom layer 500 mL of deionized water is added and 48 g of 50% NaOH is added with vigorous stirring. The solution was heated to 80° C. for 16 hours. After 16 hours the solution was removed from heat and allowed to cool to room temperature. The volume was increased to 1 L with deionized water. The product was isolated by drop wise addition of 2 molar sodium phosphate resulting in a large white precipitate. The precipitate was collected by decanting the supernatant and the precipitate was washed with deionized water and soaked in isopropyl alcohol for 2 hours and finally washed again with deionized water. The resulting solid mass was dried in a vacuum oven at 65° C. for 3 days. The dried polymer was frozen with liquid nitrogen and ground to a fine powder and further dried for 1 day. The resulting mass of the dry powder was 21.5 g. A 2% solution was made by dissolving the dried powder into 1 molar acetic acid and 0.08% HCl. The resulting solution was tested for sensitivity to a multivalent ion stimulus by drop wise addition of 2 molar sodium phosphate or 0.2 molar sodium citrate to 50 mL samples of 1% polymer solutions. Upon addition of the phosphate or citrate ions a white precipitate is observed.

Example 35

Synthesis of a High Molecular Weight Hydrophobically Modified Polyvinylamine (PVA) Stimulus Responsive Polymer Using a solution of Lupamin 9095 (linear polyvinylamine, average MW=340 kDa, 20% solids, pH 7-9) obtained from BASF, a hydrophobically modified stimulus responsive polymer was produced as follows. 300 g of Lupamin 9095 (approximately 60 g of polyvinylamine) was added to a 2 liter glass jar. Next, 40 g of NaOH pellets and 500 mL of deionized water were dissolved and added to the jar. This was followed by the addition of 500 mL 1,2-dimethoxyethane (SIGMA) as a co-solvent and the solution was stirred vigorously until homogenous. Next, 17.66 g benzyl chloride (ACROS ORGANICS, 99%) was added to the reaction jar with stirring. The solution was heated to 60° C. for 16 hours with magnetic stirring. The solution was subsequently allowed to cool to room temperature and transferred to a 5 liter beaker. Next, 1500 mL of deionized water was added with stirring. The pH was adjusted to 5 with glacial acetic acid. The product was precipitated with slow addition of 250 mL 2 molar sodium phosphate and the solid was collected and washed with deionized water.

Figure 8:
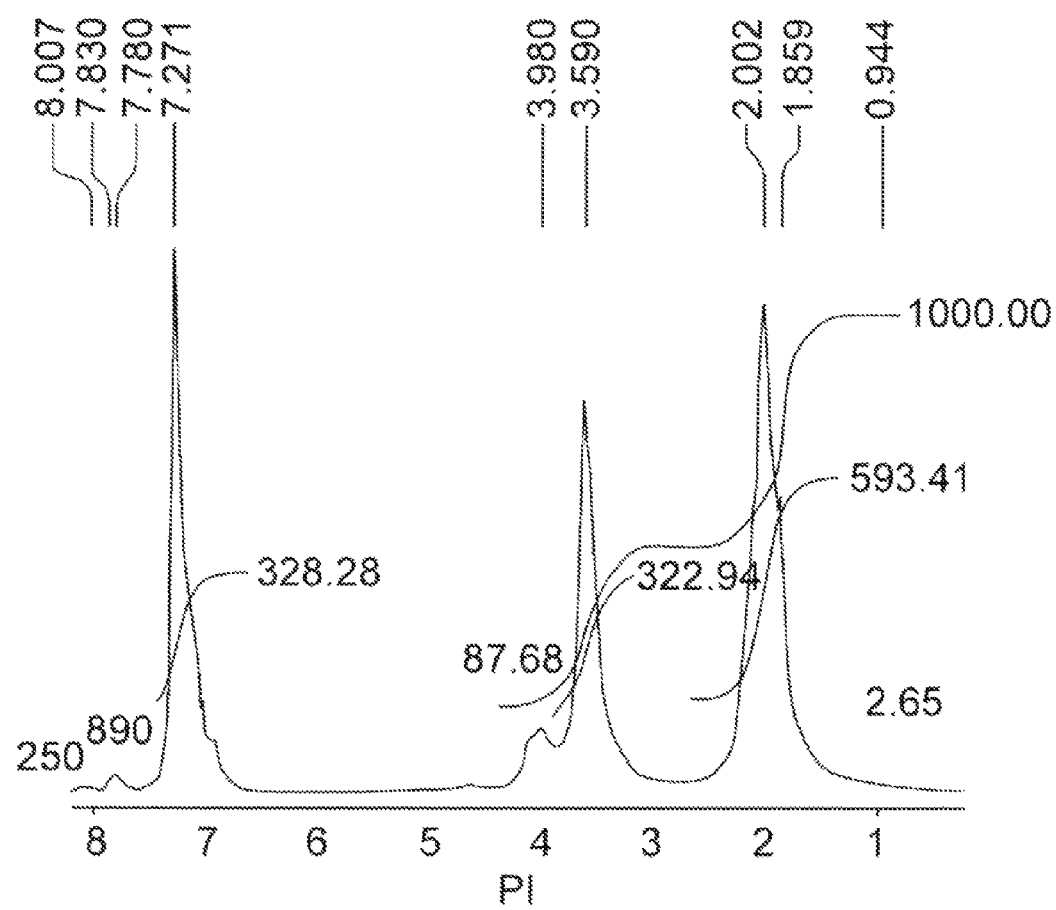
FIG. 8 depicts an NMR spectrum for modified polyvinylamine (PVA) from Example 35. Integration of the 1H NMR shows benzyl modification level of about 18%.

The polymer was further purified by the following method. The solid was dissolved in 2 liter of 1 molar acetic acid with stirring. The total volume was brought to 10 liters with deionized water and the pH is adjusted to 7 with drop wise addition of 50% NaOH. The product was precipitated with addition 600 g of 2 molar sodium phosphate. The solid was isolated via vacuum filtration and washed with deionized water. The resulting solid mass was dried in a vacuum oven at 65° C. for 3 days. The dried polymer was frozen with liquid nitrogen and ground to a fine powder and further dried for 1 day. The resulting mass of the dry powder was 46 g. A small sample was dissolved in 1 molar $CD_3COOD/D_2O$ acid and $^1$H-NMR spectra were obtained, which are depicted in FIG. 8. The $^1$H-NMR peaks were integrated and the amount of benzyl modification was determined to be 18%.

Example 36

200 g Scale Synthesis of a Hydrophobically Modified Polyallylamine Based Stimulus Responsive Polymer In an exemplary experiment described herein, it was demonstrated that the polymers described herein could be manufactured on a large scale.

Using a solution of Polyallyamine (PAA, NITTOBO, 150 kD; 40% wt./wt.), a hydrophobically modified stimulus responsive polymer was produced as follows. 500 g of Polyallyamine (PAA, NITTOBO, 150 kD; 40% wt./Wt.) (approximately 200 g of polyallylamine) was added to a 4 liter glass jar. Next, 80 g of NaOH pellets and 1000 mL of deionized water were dissolved and added to the jar. Followed by the addition of 1000 mL 1,2-dimethoxyethane (SIGMA) as a co-solvent and the solution was stirred vigorously until homogenous. Next, 114 g of benzyl chloride (ACROS ORGANICS, 99%) was added to the reaction jar. The solution was heated at 60° C. for 16 hours with magnetic stirring. The solution was allowed to cool to room temperature and transferred to a 10 liter beaker.

Figure 9:
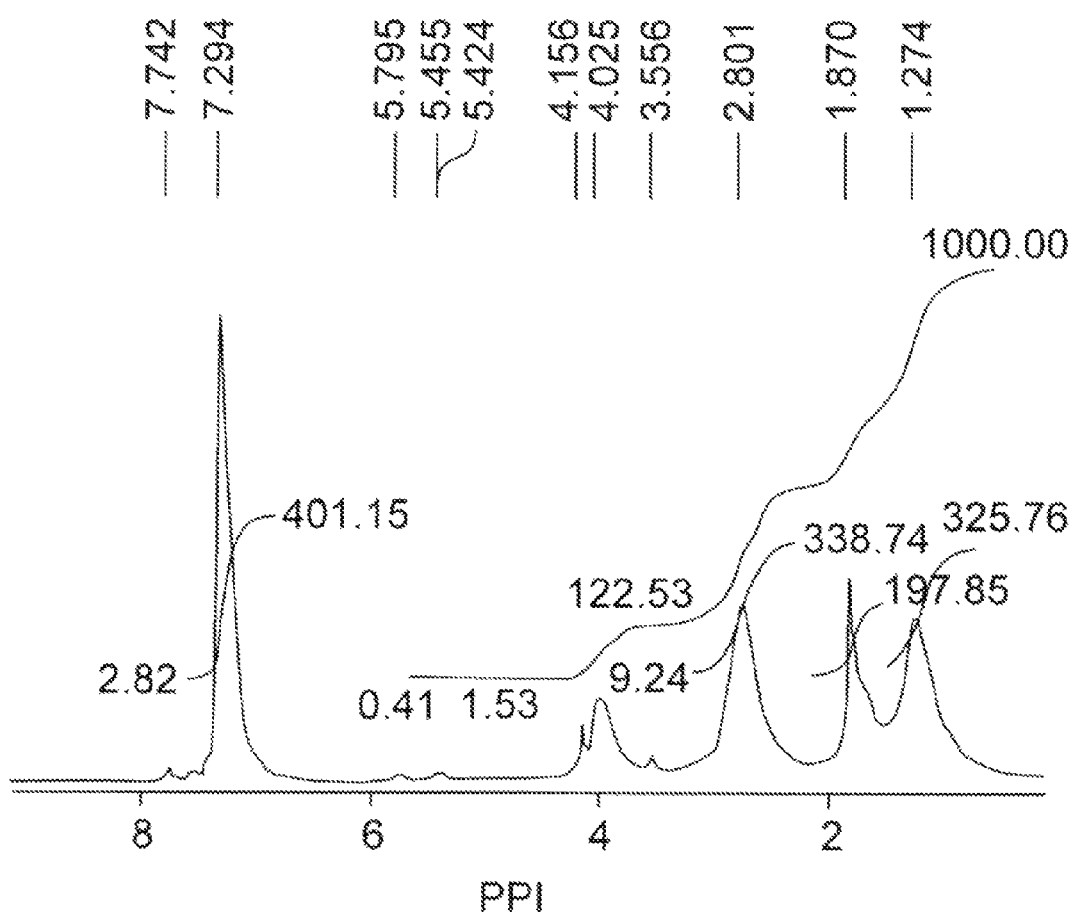
FIG. 9 depicts an NMR spectrum for modified polyallylamine from Example 36. Integration of the 1H NMR shows benzyl modification level of about 33%

Next, 1000 mL of deionized water was added with stirring and a sticky solid mass precipitated out of solution. The product was further precipitated with slow addition of 200 mL 2 molar sodium phosphate and the solid was collected and washed with deionized water. The polymer was further purified by the following method. The solid was dissolved in 3 liter of 1 molar acetic acid with stirring. The total volume was brought to 10 liters with deionized water and the pH was adjusted to 7 with drop wise addition of 50% NaOH. The product was precipitated with addition 800 g of 2 molar sodium phosphate and the solids was collected and washed with deionized water. The polymer was even further purified by the following method. The solid was dissolved in 3 liter of 1 molar acetic acid with stirring. The total volume was brought to 10 liters with deionized water and the pH was adjusted to 7 with drop wise addition of 50% NaOH. The product was precipitated with addition 800 g of 2 molar sodium phosphate and the solids was collected and washed with deionized water. The resulting solid mass was dried in a vacuum oven at 65° C. for 3 days. The dried polymer was frozen with liquid nitrogen and ground to a fine powder and further dried for 1 day. The resulting mass of the dry powder was 250 g. A small sample was dissolved in 1 molar $CD_3COOD/D_2O$ acid and $^1$H-NMR spectra were obtained, as depicted in FIG. 9. The $^1$H-NMR peaks were integrated and the amount of benzyl modification was determined to be 33%.

Example 37

Determination of Flocculation Performance and Supernatant Quality for Increasing Doses of a Stimulus Responsive Polymer vs a Cationic Polyelectrolyte in a CHO Cell Culture In an exemplary experiment described herein, the stimulus responsive polymers according to the present invention were compared to a known polymer, i.e., chitosan, for certain desirable properties.

CHO cell culture was prepared using a method, as described in Example 1: A solution of 2% w/w solution of medium molecular weight chitoson (MMW chitosan) (Sigma-Aldrich) was prepared in 1 molar acetic acid. A 2% w/w solution of hydrophobically modified polyallylamine based stimulus responsive (33%-BnPAA) polymer was prepared according to Example #36. 10 mL of the CHO cell culture was dispensed into 15 mL conical tubes. Individual polymer doses of 0.0, 0.1, 0.2, 0.03, 0.04, 0.05, 0.06, 0.07, 0.08, 0.09, 0.1, 0.14, 0.18, 0.22, and 0.4% w/v were added to each conical tube containing CHO cell culture for each the LMW chitosan and 33%-BnPAA. For the conical tubes containing the 33%-BnPAA only, the pH was adjusted to 7.2 and a stimulus of 150 mM sodium phosphate was applied. All the conical tubes were centrifuged at 3000 RPM for 2 minutes and the supernatant was decanted and the turbidity was determined.

Figure 10:
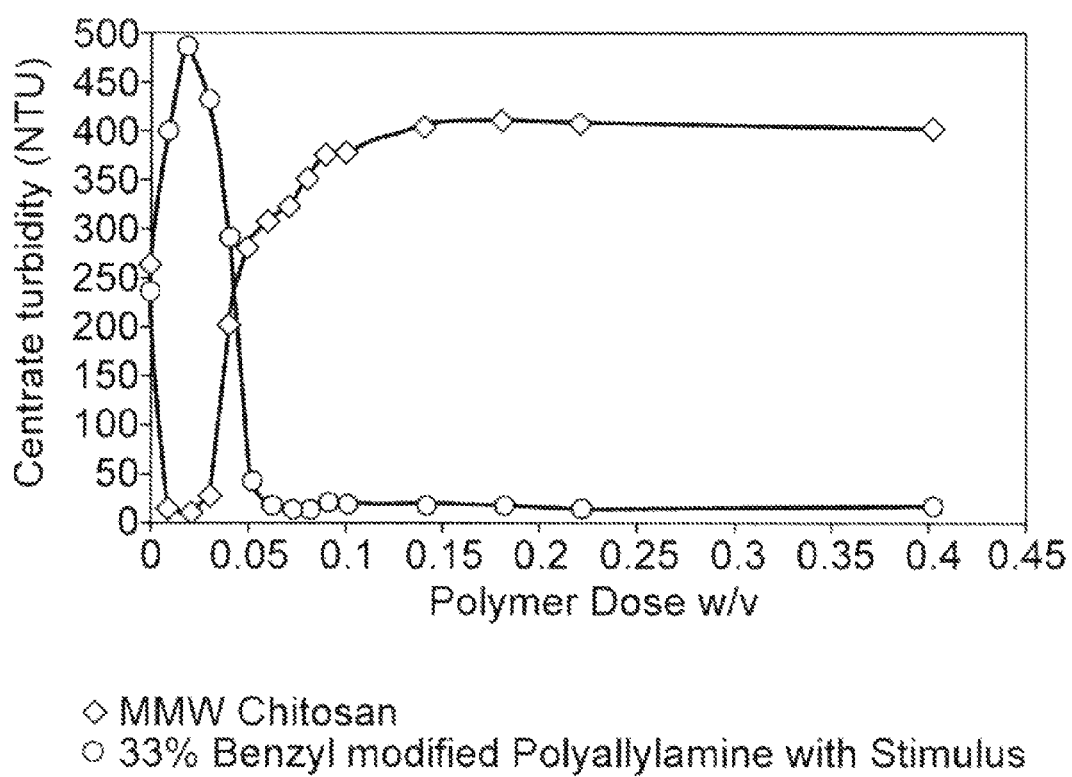
FIG. 10 depicts a graph demonstrating the effect of polymer dosing for a non-stimulus responsive polymer (e.g., chitosan) and a stimulus responsive polymer (e.g., benzyl modified polyallylamine) on centrate turbidity. The X-axis is the polymer dose (wt %) and the Y-axis is the centrate turbidity (NTU), as described in Example 37.

Table 5 below and FIG. 10 summarize the results of a representative experiment to demonstrate that a non-stimulus responsive polymer (e.g., chitosan) requires dose optimization for efficient flocculation, whereas, a stimulus responsive polymer according to the present invention does not appear to require dose optimization. In other words, in case of a non-stimulus responsive polymer such as chitosan, once an optimal dose of the polymer is added for efficient flocculation, exceeding that optimal dose results in increased turbidity, which is undesirable. Whereas, in case of stimulus responsive polymers such as those described herein, the stimulus responsive polymer continues to be an effective flocculant/precipitant regardless of increase in the dose.

TABLE 5

| Polymer Flocculant Dose (w/v)% | Polymer Flocculant | Stimulus (y/n) | Supernatant Turbidiy (NTU) |
|---|---|---|---|
| 0 | MMW Chitosan | n | 266 |
| 0.01 | MMW Chitosan | n | 14 |
| 0.02 | MMW Chitosan | n | 13 |
| 0.03 | MMW Chitosan | n | 28 |
| 0.04 | MMW Chitosan | n | 200 |
| 0.05 | MMW Chitosan | n | 282 |

TABLE 5-continued

| Polymer Flocculant Dose (w/v)% | Polymer Flocculant | Stimulus (y/n) | Supernatant Turbidiy (NTU) |
|---|---|---|---|
| 0.06 | MMW Chitosan | n | 311 |
| 0.07 | MMW Chitosan | n | 325 |
| 0.08 | MMW Chitosan | n | 353 |
| 0.09 | MMW Chitosan | n | 378 |
| 0.1 | MMW Chitosan | n | 379 |
| 0.14 | MMW Chitosan | n | 404 |
| 0.18 | MMW Chitosan | n | 409 |
| 0.22 | MMW Chitosan | n | 405 |
| 0.4 | MMW Chitosan | n | 400 |
| 0 | 33% Benzyl modified Polyallylamine | y | 237 |
| 0.01 | 33% Benzyl modified Polyallylamine | y | 399 |
| 0.02 | 33% Benzyl modified Polyallylamine | y | 486 |
| 0.03 | 33% Benzyl modified Polyallylamine | y | 433 |
| 0.04 | 33% Benzyl modified Polyallylamine | y | 293 |
| 0.05 | 33% Benzyl modified Polyallylamine | y | 42 |
| 0.06 | 33% Benzyl modified Polyallylamine | y | 19 |
| 0.07 | 33% Benzyl modified Polyallylamine | y | 14 |
| 0.08 | 33% Benzyl modified Polyallylamine | y | 16 |
| 0.09 | 33% Benzyl modified Polyallylamine | y | 21 |
| 0.1 | 33% Benzyl modified Polyallylamine | y | 20 |
| 0.14 | 33% Benzyl modified Polyallylamine | y | 17 |
| 0.18 | 33% Benzyl modified Polyallylamine | y | 17 |
| 0.22 | 33% Benzyl modified Polyallylamine | y | 12 |
| 0.4 | 33% Benzyl modified Polyallylamine | y | 14 |

Example 38

Determination of Flocculation Performance and Supernatant Quality with Increasing Doses of a Stimulus Responsive Polymer in the Presence of a Multivalent Anion Stimulus Relative to No Stimulus, in CHO Cell Culture CHO cell culture was prepared using a method, as described in Example 1. A 2% w/w solution of hydrophobically modified polyallylamine based stimuli responsive (33%-BnPAA) polymer was prepared according to Example #36. Individual polymer doses of 0.0, 0.05, 0.06, 0.07, 0.08, 0.09, 0.1, 0.14, 0.18, 0.22, and 0.4% w/v were added to each conical tube containing CHO cell culture in triplicates (one for phosphate and one for citrate and one for no stimuli) for 33%-BnPAA polymer. The pH was adjusted to 7.2 and a stimulus of 150 mM sodium phosphate or 150 mM sodium citrate was applied or no stimulus was applied. All the conical tubes were centrifuged at 3000 RPM for 2 minutes and the supernatant was decanted and the centrate turbidity was determined. The results from the experiments described in this example are shown in Table 6 and FIG. 11.

Figure 11:
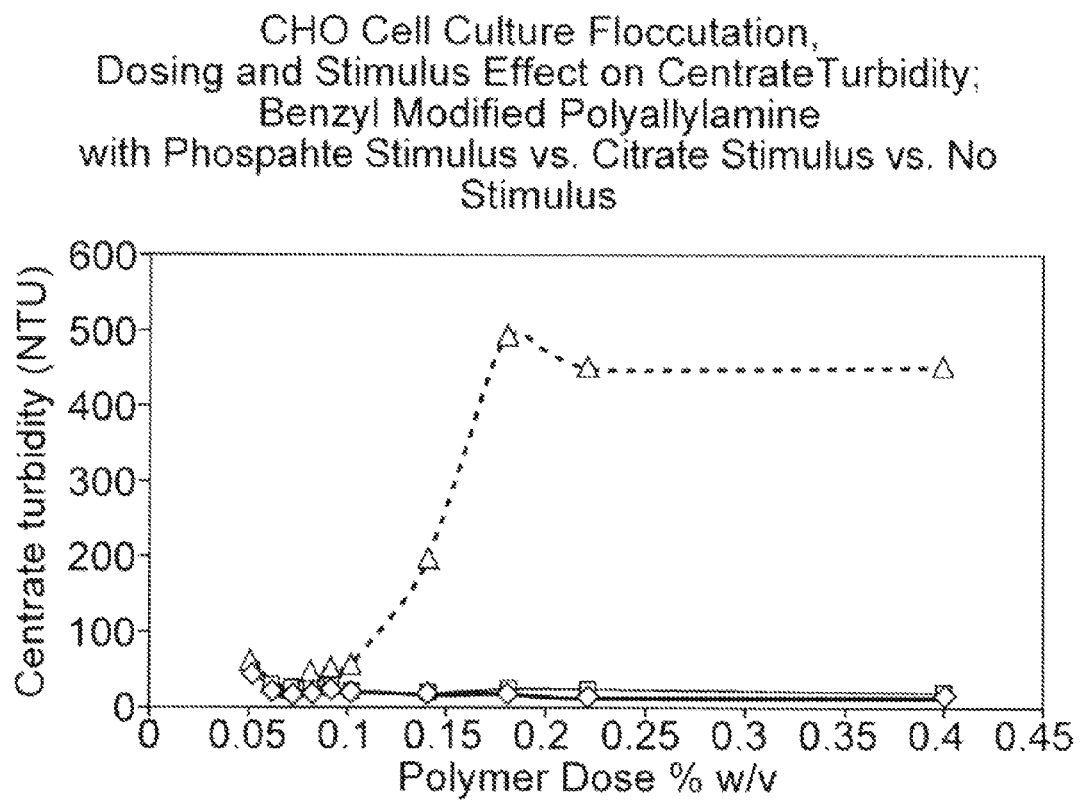
FIG. 11 depicts a graph demonstrating the effect of polymer dose in the presence and absence of a stimulus for a benzyl polyallylamine stimulus responsive polymer. The X-axis is the polymer dose in wt % and Y-axis is the centrate turbidity (NTU), as described in Example 38.
Figure 12:
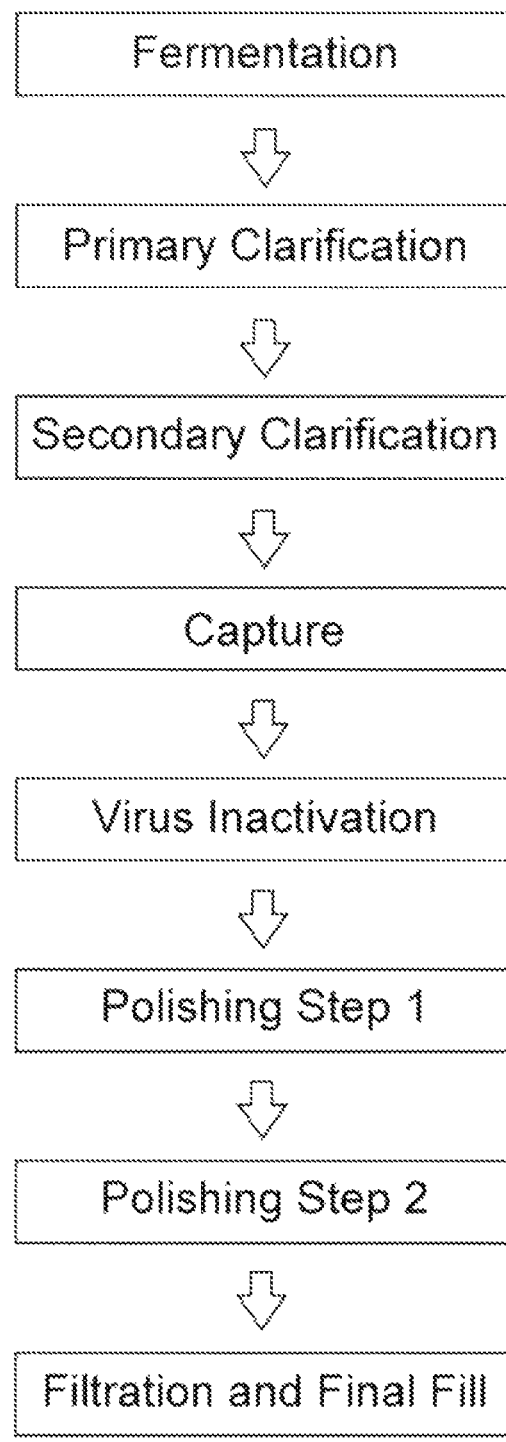
FIG. 12 depicts a typical scheme used for the purification of biomolecules.
Figure 13:
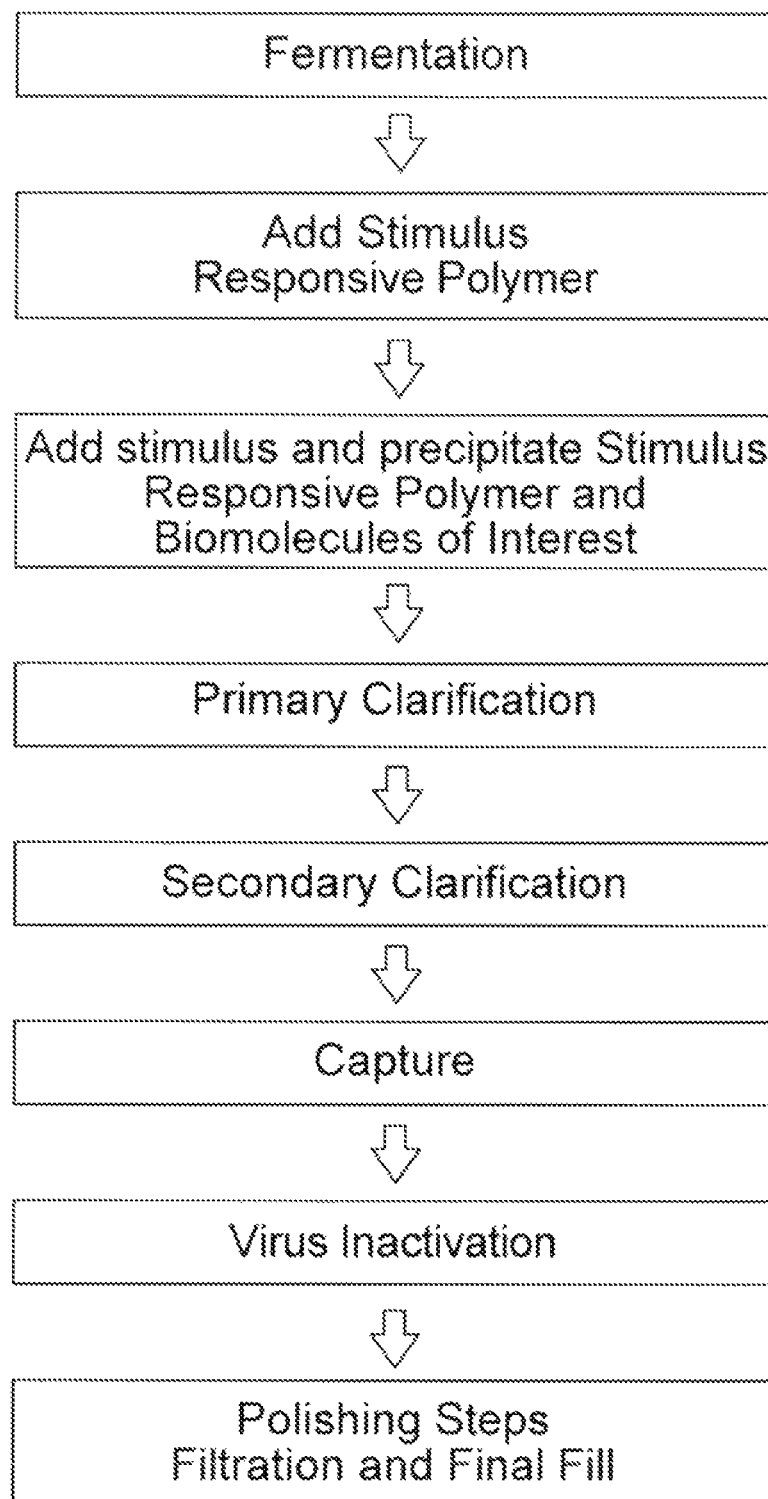
FIG. 13 depicts a purification scheme including a stimulus responsive polymer used to improve the clarification of the cell culture. The stimulus responsive polymer removes one or more impurities, however, the polymer does not bind the desired target molecule.
Figure 14:
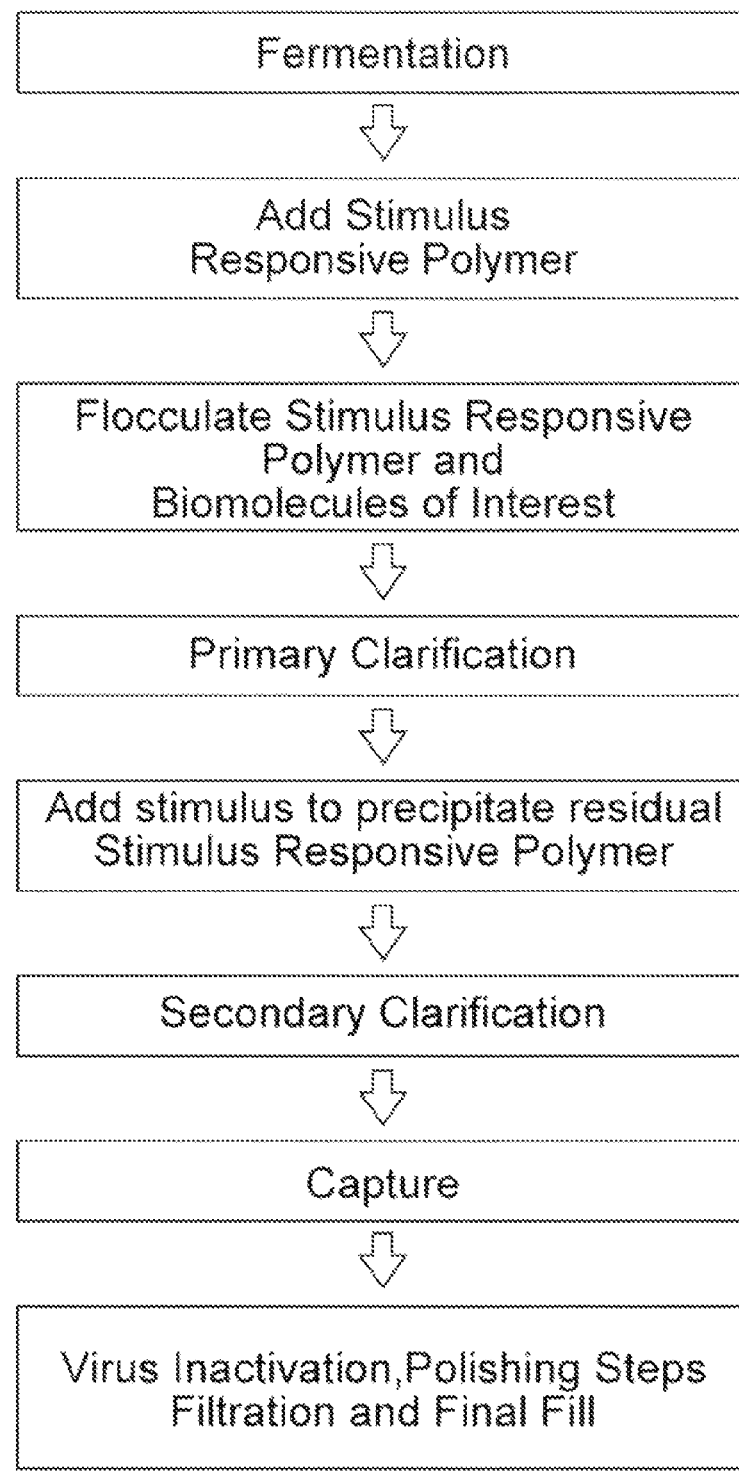
FIG. 14 depicts a purification scheme including a stimulus responsive polymer used to improve the clarification of the cell culture. The stimulus responsive polymer removes one or more impurities via flocculation, however, the polymer does not bind the desired target molecule and the residual polymer is removed by adding a stimulus after clarification.
Figure 15:
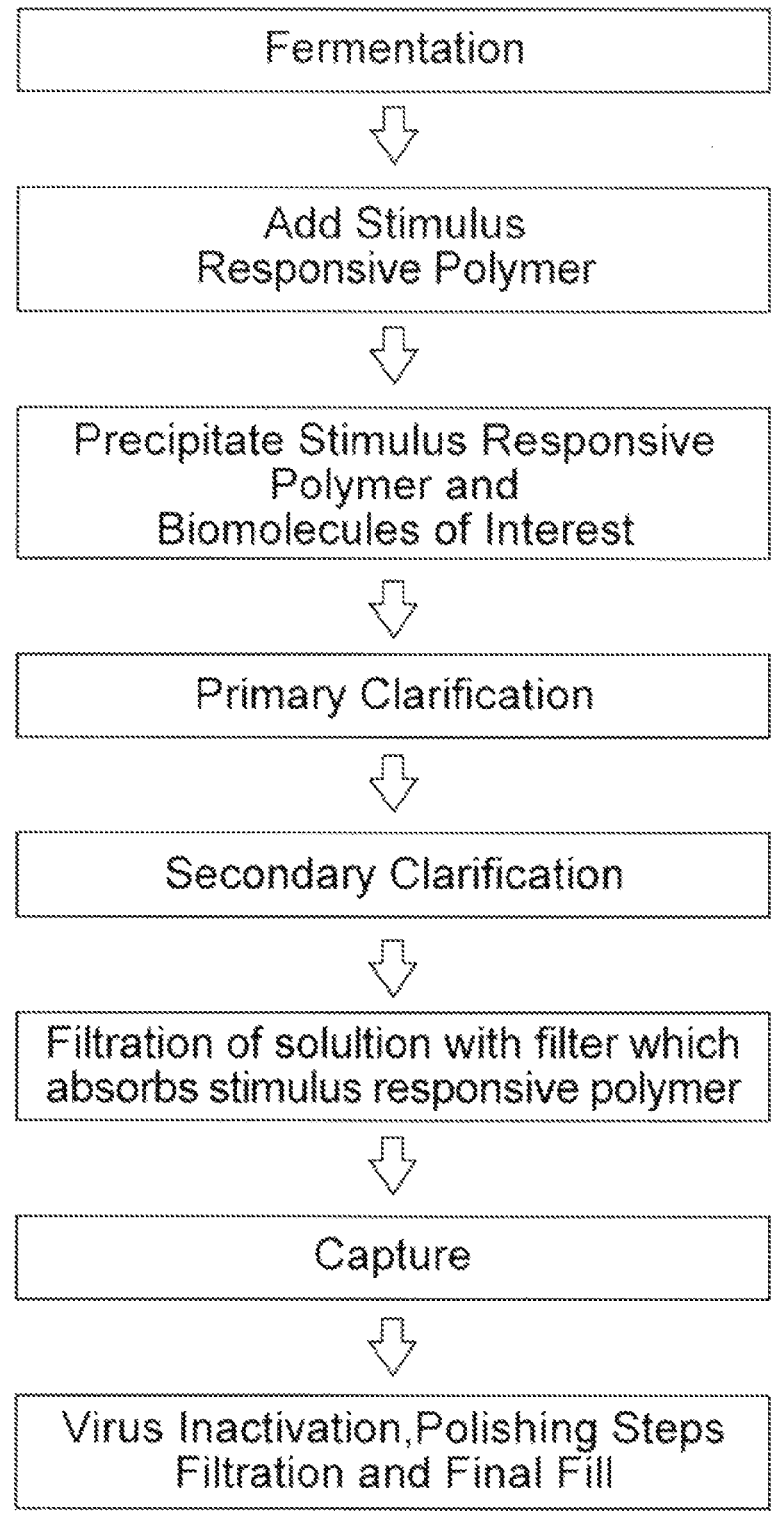
FIG. 15 depicts a purification scheme including a stimulus responsive polymer used to improve the clarification of the cell culture. The stimulus responsive polymer removes one or more impurities, however, the polymer does not bind the target molecule and the residual polymer is removed by an additional adsorptive filtration step following clarification.

Table 6 and FIG. 11 summarize the results of a representative experiment to demonstrate that a stimulus responsive polymer (e.g., described in Example 36) can operate as a non-stimulus responsive flocculant (similar to Chitosan data in Example 37), requiring polymer dose optimization without a stimulus. However, with a multivalent ion stimulus, such as phosphate or citrate, the stimulus responsive polymer does not require dose optimization as the centrate turbidity is not effected by increasing polymer dose.

TABLE 6

| Polymer Flocculant Dose (w/v)% | Polymer Flocculant | Stimulus (phosphate/ citrate/none) | Supernatant Turbidiy (NTU) |
|---|---|---|---|
| 0 | 33% Benzyl modified Polyallylamine | phosphate | 237 |
| 0.05 | 33% Benzyl modified Polyallylamine | phosphate | 42 |
| 0.06 | 33% Benzyl modified Polyallylamine | phosphate | 19 |
| 0.07 | 33% Benzyl modified Polyallylamine | phosphate | 14 |
| 0.08 | 33% Benzyl modified Polyallylamine | phosphate | 16 |
| 0.09 | 33% Benzyl modified Polyallylamine | phosphate | 21 |
| 0.1 | 33% Benzyl modified Polyallylamine | phosphate | 20 |
| 0.14 | 33% Benzyl modified Polyallylamine | phosphate | 17 |
| 0.18 | 33% Benzyl modified Polyallylamine | phosphate | 17 |
| 0.22 | 33% Benzyl modified Polyallylamine | phosphate | 12 |
| 0.4 | 33% Benzyl modified Polyallylamine | phosphate | 14 |
| 0.05 | 33% Benzyl modified Polyallylamine | citrate | 50 |
| 0.06 | 33% Benzyl modified Polyallylamine | citrate | 29 |
| 0.07 | 33% Benzyl modified Polyallylamine | citrate | 27 |
| 0.08 | 33% Benzyl modified Polyallylamine | citrate | 23 |
| 0.09 | 33% Benzyl modified Polyallylamine | citrate | 30 |
| 0.1 | 33% Benzyl modified Polyallylamine | citrate | 21 |
| 0.14 | 33% Benzyl modified Polyallylamine | citrate | 19 |
| 0.18 | 33% Benzyl modified Polyallylamine | citrate | 24 |
| 0.22 | 33% Benzyl modified Polyallylamine | citrate | 23 |
| 0.4 | 33% Benzyl modified Polyallylamine | citrate | 20 |
| 0.05 | 33% Benzyl modified Polyallylamine | none | 64 |
| 0.06 | 33% Benzyl modified Polyallylamine | none | 33 |
| 0.07 | 33% Benzyl modified Polyallylamine | none | 23 |
| 0.08 | 33% Benzyl modified Polyallylamine | none | 46 |
| 0.09 | 33% Benzyl modified Polyallylamine | none | 51 |
| 0.1 | 33% Benzyl modified Polyallylamine | none | 55 |
| 0.14 | 33% Benzyl modified Polyallylamine | none | 199 |
| 0.18 | 33% Benzyl modified Polyallylamine | none | 492 |
| 0.22 | 33% Benzyl modified Polyallylamine | none | 454 |
| 0.4 | 33% Benzyl modified Polyallylamine | none | 455 |

Example 39

Determination of Flocculation Performance and Supernatant Quality with Increasing Doses of an Unmodified Stimulus Responsive Polymer in CHO Cell Culture In another experiment, the flocculation ability and supernatant quality with an unmodified stimulus responsive polymer in a CHO cell culture was determined, as described herein.

CHO cell culture was prepared using a method, as described in Example 1. A 2% w/w solution of unmodified polyallylamine based stimuli responsive polymer was prepared by dissolving Polyallyamine (PAA, NITTOBO, 150 kD; 40% wt./wt.) in 1 molar acetic acid. 10 mL of the CHO cell culture is dispensed into 15 mL conical tubes. Individual polymer doses of 0.0, 0.05, 0.06, 0.07, 0.08, 0.09, 0.1, 0.14, 0.18, 0.22, and 0.4% w/w was added to each conical tube containing CHO cell culture. The pH was adjusted to 7.2 and a stimulus of 150 mM sodium phosphate was applied. All the conical tubes were centrifuged at 3000 RPM for 2 minutes and the supernatant was decanted and the turbidity was determined. The results from the experiments described in this example are shown in Table 7.

TABLE 7

| Polymer Flocculant Dose (w/v)% | Polymer Flocculant | Stimulus (y/n) | Supernatant Turbidiy (NTU) |
|---|---|---|---|
| 0.05 | umodified 150 kD Polyallyamine | n | 171 |
| 0.06 | umodified 150 kD Polyallyamine | n | 426 |
| 0.07 | umodified 150 kD Polyallyamine | n | 673 |
| 0.08 | umodified 150 kD Polyallyamine | n | 959 |
| 0.09 | umodified 150 kD Polyallyamine | n | 947 |
| 0.1 | umodified 150 kD Polyallyamine | n | >1000 |
| 0.14 | umodified 150 kD Polyallyamine | n | >1000 |
| 0.18 | umodified 150 kD Polyallyamine | n | >1000 |
| 0.22 | umodified 150 kD Polyallyamine | n | >1000 |
| 0.4 | umodified 150 kD Polyallyamine | n | >1000 |

Example 40

Determination of Flocculation Performance, Settling Time, and Supernatant Quality a Stimuli Responsive Polymer in CHO Cell Culture CHO cell culture was prepared using a method as described in Example 1. A 10% w/w solution of a hydrophobically modified polyallylamine based stimuli responsive (33%-Bn-PAA) polymer was prepared similar to Example #36. 50 mL of CHO cell culture was placed in a 100 mL glass graduated cylinder in duplicates. In one of the cylinders, the stimulus responsive polymer was added to a dose of 0.5%, the pH was adjusted to 7 with drop wise addition of 2 molar tris base, the sodium phosphate concentration was adjusted to 50 mM by addition of a 2 molar sodium phosphate solution, and the solution was stirred for 2 minutes. The sodium phosphate and adjustment was performed in order to precipitate the stimulus responsive polymer and a complex of cells, cell debris, impurities, residual polymer; to flocculate the solids; and to increase particle size. After the sodium phosphate addition and pH adjustment, large aggregated particles were observed in the stimulus responsive polymer treated feed. The other graduated cylinder was stirred for 2 minutes and nothing was added. Both of the cylinders were allowed to sit undisturbed for 1 hour. At the end of an hour, the supernatant was aspirated and the turbidity was recorded.

It was observed that the solid phase in the cylinder with the smart polymer settles faster as well as a defined settling front (sharp solid to liquid phase transition) relative to the solid phase in the untreated cylinder, which gave an undefined settling front.

The results of one such experiment are summarized in Table 8. The measurements with respect to the settling fronts were a rough estimate for the untreated cylinder because the settling front was largely dispersed and undefined.

TABLE 8

| Time (minutes) | Polymer | Settling Front (% Solids) | Final Supernatant Turbidity (NTU) |
|---|---|---|---|
| 10 | 33% Benzyl modified Polyallylamine | 100 | |
| 20 | 33% Benzyl modified Polyallylamine | 100 | |
| 30 | 33% Benzyl modified Polyallylamine | 62 | |
| 40 | 33% Benzyl modified Polyallylamine | 50 | |
| 50 | 33% Benzyl modified Polyallylamine | 47 | |
| 60 | 33% Benzyl modified Polyallylamine | 42 | 18 |
| 10 | None | 100 | |
| 20 | None | 100 | |
| 30 | None | 95 | |
| 40 | None | 93 | |
| 50 | None | 88 | |
| 60 | None | 84 | 589 |

Example 41

Comparison of Clarification Performance Using Polyamines of Different Molecular Weights A series of polymers with different molecular weights were obtained, modified, and used to flocculate, precipitate, and purify a cell culture. Polymers with primary amine repeat units of molecular weights of 15 kD, 85 kD, 150 kD, 350 kD, 600-950 kD and 2000-4000 kD were obtained and/or modified by the following methods.

The 15 kD polyallylamine polymer was obtained from NITTOBO and was benzylated (covalently attached benzyl groups and purified) using a method similar to example 36. The 85 kD benzylated polyvinylamine polymer was prepared by Example 23. The 150 kD benzylated polyallylamine was prepared according to Example 36. The 350 kD benzylated polyvinylamine polymer was prepared by Example 35. The 950 kD polyvinylamine polymer backbone is prepared by hydrolyzing Polymin VZ (BASF) with 2 equivalents of base at 80° C. for 8 hours. The unmodified 2000-4000 kD PVA was prepared according to example 31. The benzylated 2000-4000 kD polymer was prepared according to Example 32. The polymers were used to flocculate, precipitate, and purify a CHO DG44 cell culture of approximately $12 \times 10^6$ cells/mL and a harvest cell viability of <50%. The flocculation was performed at polymer doses of 0.2% and 0.4% w/w. A solution stimulus of 50 mM sodium phosphate and pH adjustment to 7 with 2 molar tris base was applied.

Observations about the flock size were recorded and are denoted as + being small flocks and +++++ being very large aggregates. The vials denoted +++++ were more of a complete zone separation than a suspension of aggregates. It is also noted that the larger aggregates/particles settle faster with a sharper solid liquid interface. Results are shown in Table 9, which demonstrates the results for flocculation using polyamines of different molecular weights.

TABLE 9

| Molecular Weight (kD) | Polymer Dose (w/w) | Aggregate/Particle Size |
|---|---|---|
| 15 | 0.2 | + |
| 85 | 0.2 | + |
| 150 | 0.2 | ++ |
| 350 | 0.2 | +++ |
| 600-900 | 0.2 | +++ |
| 2000-4000 | 0.2 | ++++ |
| 15 | 0.4 | + |
| 85 | 0.4 | + |
| 150 | 0.4 | +++ |
| 350 | 0.4 | ++++ |
| 600-900 | 0.4 | ++++ |
| 2000-4000 | 0.4 | +++++ |

Example 42

Comparison of Clarification Performance Using Polyamines of Different Hydrophobic Modifications CHO cell culture was prepared using a method, as described in Example 1. Samples of polymers described in Examples 31, 32, 33 and 35 were added to the cell culture as described in Example 38 with the following exceptions: The polymer dose was between 0.1 wt % and 0.6 wt % as described in Table 10. The initial cell culture turbidity was ~900 NTU and the centrate without polymer treatment had a turbidity of 212 NTU. The pH was adjusted to 7.2 and a stimulus of 50 mM sodium phosphate was applied. All the conical tubes were centrifuged at 3000 RPM for 2 minutes and the supernatant was decanted and the centrate turbidity was determined. The results from the experiments described in this example are shown in Table 10, which demonstrates the performance of different hydrophobic modifications at different polymer doses.

Table 10 demonstrates that by changing the nature of the hydrophobic group and/or polymer molecular weight, the response to stimulus and resulting centrate turbidity can be varied.

TABLE 10

| Polymer | Polymer Dose (w/w) | Centrate Turbidity (NTU) |
|---|---|---|
| Untreated (No Polymer) | 0 | 212 |
| Example 31 | 0.2 | 12 |
| Example 31 | 0.6 | 76 |
| Example 32 | 0.2 | 92 |
| Example 32 | 0.6 | 26 |

TABLE 10-continued

| Polymer | Polymer Dose (w/w) | Centrate Turbidity (NTU) |
| --- | --- | --- |
| Example 33 | 0.2 | 17 |
| Example 33 | 0.6 | 61 |
| Example 35 | 0.1 | 19 |
| Example 35 | 0.2 | 12 |
| Example 35 | 0.4 | 36 |
| Example 35 | 0.6 | 32 |

Example 43

Effect of Reduced Turbidity Obtained with Stimulus Responsive Polymers on Downstream Filtration In order to assess the affect of the stimulus responsive polymer on subsequent centrifugation and depth filtration steps, the following procedure was followed. DG44 chinese Hamster Ovary (CHO) cell line expressing PTG1 antibody were grown in a 10 L bioreactor (NEW BRUNSWICK SCIENTIFIC) to a density of about 15×106 cells/mL and harvested at <50% viability. A 10% w/w solution of a hydrophobically modified polyallylamine based stimuli responsive (33%-BnPAA) polymer is prepared similar to Example 36.

One fraction of the DG44 CHO cell culture is treated with 0.2% of the stimulus responsive polymer 33%-BnPAA, while another fraction of the DG44 CHO cell culture is not treated. To the stimulus responsive polymer treated cell culture, the sodium phosphate concentration is brought to 50 mM by drop wise addition of 2 molar sodium phosphate and the pH is adjusted to 7.2 by drop wise addition of 2 molar tris base. The sodium phosphate and pH adjustment is performed in order to precipitate the stimuli responsive polymer and a complex of cells, cell debris, impurities, residual polymer, and to flocculate the solids, and increase particle size. After the sodium phosphate addition and pH adjustment, large flocked particles are observed in the stimuus responsive polymer treated feed. Both fractions were centrifuged for 5 minutes at 3000 RPM and the supernatants were decanted and the turbidity was determined. The centrate turbidity for the 33%-BnPAA polymer treated feed was determined to be 10 NTU while the centrate turbidity for the untreated feed was determined to be 60 NTU.

Depth filter throughput for each feed was determined by the following method. A X0HC Millistak+® Pod Disposable Depth Filter (MILLIPORE) with a surface area of 23 cm$^2$ used for each feed. The depth filters were equipped with a peristaltic pump and an in-line pressure sensor. The filters were flushed with deionized water according to instructions and the feed was pumped through at 100 LMH and the filtrates were pooled. The pooled turbidity for the 33%-BnPAA polymer treated feed filtrate was 6 NTU and the pooled turbidity for the untreated feed filtrate was 9 NTU. The filter throughput for the 33%-BnPAA polymer treated feed was 1304 L/m2 at 10 psi, at which time the experiment was stopped because of feed limitations. The filter throughput for the untreated feed was 206 L/m2 at 20 psi, at which time the experiment was stopped because of pressure limitations.

Example 44

Purification of a Model Protein Stream with a Stimulus Responsive Polymer Followed by Capture with a Affinity Resin In order to better assess the affect of the stimulus responsive polymer on subsequent purification steps, a model feed was prepared and the following procedure was followed. CHO cell culture is prepared using a method similar to Example 1. Initial Feed HCP level ~210,000 ppm. A 10% w/w solution of a hydrophobically modified polyallylamine based stimuli responsive (33%-BnPAA) polymer is prepared similar to Example 36. One fraction of the CHO cell culture is treated with 0.1% of the stimuli responsive polymer 33%-BnPAA, while another fraction of the CHO cell culture is treated with 0.4% of the stimuli responsive polymer 33%-BnPAA, and a third fraction of the CHO cell culture is not treated. To the stimuli responsive polymer treated cell cultures the sodium phosphate concentration is brought 50 mM by drop wise addition of 2 molar sodium phosphate and the pH is adjusted to 7.2 by drop wise addition of 2 molar tris base. The sodium phosphate and pH adjustment is performed in order to precipitate the stimuli responsive polymer and a complex of cells, cell debris, impurities, residual polymer, and to flocculate the solids, and increase particle size. After the sodium phosphate, addition and pH adjustment large flocked particles are observed in the stimuli responsive polymer treated feeds. Each fraction of the cell culture is centrifuged in a lab scale bucket centrifuge for 5-minutes at 3000 RPM. The turbidty of each centrate is recorded and reported in Table 11. The centrates are filtered through a 0.2 μm Durapore® filter.

The filtrate pools were purified through a three step chromatography based purification consisting of protein A affinity chromatography (ProSep Ultra Plus®), bind-and-elute cation exchange chromatography (ProRes S®), and membrane adsorber anion exchange chromatography in flow-though mode (ChromaSorb®). The purification was performed on a chromatography workstation according to the method in Table 12. The pools for each step were analyzed for host cell protein (CHOP) by ELISA, leached Protein A (L ProA) by ELISA, residual DNA by PicoGreen® assay, turbidity, aggregated protein (AGG) percent by size exclusion HPLC, and protein concentration by UV absorption.

TABLE 11

| Feed Treatment | Centrate (NTU) | Mab Recovery (%) | CHOP Removal (%) | DNA (ug/mL) |
| --- | --- | --- | --- | --- |
| Centrifuge Only | 127 | 100 | 0 | 49 |
| 0.1% Bn25PAA | 7.3 | 90 | 50 | <LOQ |
| 0.4% Bn25PAA | 9.2 | 78 | 50 | <LOQ |

| | Protein A Pools | | | | |
| --- | --- | --- | --- | --- | --- |
| Feed Treatment | Virus Inactivation, low pH hold Pool (NTU) | Step Yield (%) | [CHOP] (ppm) | AGG % | L ProA (ppm) | DNA (ug/mL) |
| Centrifuge Only | 45 | 99 | 2135 | 3 | >25 | 0.84 |
| 0.1% Bn25PAA | 2.4 | 99 | 507 | 2.9 | 12 | <LOQ |
| 0.4% Bn25PAA | 2 | 100 | 267 | 3 | >25 | <LOQ |
| Centrifuge Only | 87 | 684 | 2.3 | <LOQ | <LOQ |
| 0.1% Bn25PAA | 91 | 282 | 2.4 | <LOQ | <LOQ |
| 0.4% Bn25PAA | 86 | 133 | 2.4 | <LOQ | <LOQ |

TABLE 11-continued

ChromaSorb Pools

| Feed Treatment | Step Yield (%) | [CHOP] (ppm) | L ProA | DNA (ug/mL) |
|---|---|---|---|---|
| Centrifuge Only | 93 | 1.0 or <LOQ | <LOQ | <LOQ |
| 0.1% Bn25PAA | 96 | 0.7 or <LOQ | <LOQ | <LOQ |
| 0.4% Bn25PAA | 95 | 0.7 or <LOQ | <LOQ | <LOQ |

TABLE 12

Protein A
Column Dimensions 0.66 × 14 cm
Method

| Step | Buffer | Duration (Column Volumes) | Residence Time |
|---|---|---|---|
| EQ | Phospahte buffered saline | 5 | 3 |
| Load | 0.9 mg/mL Clarified feedstock | 214 mL | 4 |
| Wash | Phospahte buffered saline | 9 | 3 |
| Elution | 50 mM Acetic acid, pH 3.0 | 6 | 3 |
| Acid Strip | 150 mM Phosphoric acid | 3 | 3 |
| EQ | Phospahte buffered saline | 5 | 3 |

Cation Exchange
Column Dimensions 0.66 × 14 cm
Method

| Step | Buffer | Duration (Column Volumes) | Residence Time |
|---|---|---|---|
| EQ | 50 mM Acetic acid, 25 mM NaCl, pH 5.0 | 3 | 3 |
| Load | Protein A elution pool adjusted to pH 5 with 50 mM Acetic acid, 25 mM NaCl, pH 5.0 | load density = 40 mg/mL | 4 |
| Wash | 50 mM Acetic acid, 25 mM NaCl, pH 5.0 | 3 | 3 |
| Elution | 50 mM Acetic acid, 125 mM NaCl, pH 5.0 | 6 | 3 |
| NaCl Strip | 50 mM Acetic acid, 500 mM NaCl, pH 5.0 | 3 | 3 |
| NaOH Cleaning | 0.5M NaOH | 3 | 3 |
| EQ | 50 mM Acetic acid, 25 mM NaCl, pH 5.0 | 15 | 3 |

Anion Exchange
ChromaSorb 0.08 mL
Method

| Step | Buffer | Duration (Column Volumes) | Flow Rate (mL/minute) |
|---|---|---|---|
| EQ | 50 mM Tris pH 7.4 | 300 | 1 |
| Load | Cation exchange pool adjusted with 50 mM tris pH 7.4 | Load Density = 2.5 kg/L | 1 |

Example 45

Purification of a Model Protein Stream with a Stimulus Responsive Polymer Followed by Capture with a Cation Exchange Resin In order to better assess the affect of the stimulus responsive polymer on subsequent purification steps, the following procedure was followed. DG44 Chinese Hamster Ovary (CHO) cell line expressing PTG1 antibody were grown in a 10 L bioreactor (New Brunswick Scientific) to a density of about 15×106 cells/mL and harvested at <50% viability with an HCP level of ~142000 ppm.

A 10% w/w solution of a hydrophobically modified polyallylamine based stimuli responsive (33%-BnPAA) polymer was prepared similar to Example #36. One fraction of the CHO cell culture was treated with 0.1% of the stimuli responsive polymer 33%-BnPAA, while another fraction of the CHO cell culture was treated with 0.4% of the stimuli responsive polymer 33%-BnPAA, and a third fraction of the CHO cell culture was not treated. To the stimuli responsive polymer treated cell cultures, sodium phosphate concentration was brought to 50 mM by drop wise addition of 2 molar sodium phosphate and the pH was adjusted to 7.2 by drop wise addition of 2 molar tris base. The sodium phosphate and pH adjustment was performed in order to precipitate the stimuli responsive polymer and a complex of cells, cell debris, impurities, residual polymer, and to flocculate the solids, and increase particle size. After the sodium phosphate addition and pH adjustment large aggregated particles are observed in the stimuli responsive polymer treated feeds. Each fraction of the cell culture is centrifuged in a lab scale bucket centrifuge for 5 minutes at 3000 RPM. The turbidty of each centrate is recorded and reported in Table 13. The centrates were filtered through a 0.2 μm Durapore® filter.

The filtrate pools were purified through a two step chromatography based purification consisting of bind-and-elute cation exchange chromatography (ProRes S®), and membrane adsorber anion exchange chromatography in flow-though mode (ChromaSorb®). The purification was performed on a chromatography workstation according to the method in Table 12. The pools for each step were analyzed for host cell protein (CHOP) by ELISA, leached Protein A (L ProA) by ELISA, residual DNA by PicoGreen® assay, turbidity, aggregated protein (AGG) percent by size exclusion HPLC, and protein concentration by UV absorption.

TABLE 13

| Feed Treatment | Centrate (NTU) | Mab Recovery (%) | CHOP Removal (%) | DNA (ug/mL) |
|---|---|---|---|---|
| untreated | >1000 | 100 | 0 | 11.9 |
| 0.1% Polymer | 2 | 92 | 56 | <LOQ |
| 0.4% Polymer | 12 | 90 | 65 | <LOQ |
| CEX Pools | | | | |
| Feed Treatment | Step Yield (%) | [CHOP] (ppm) | Agg (%) | DNA (ug/mL) |
| 0.1% Polymer | 80 | 897 | <0.1 | <LOQ |
| 0.4% Polymer | 84 | 500 | <0.1 | <LOQ |
| ChromaSorb Pools | | | | |
| Feed Treatment | Step Yield (%) | [CHOP] (ppm) | | DNA (ug/mL) |
| 0.1% Polymer | 96 | 270 | | <LOQ |
| 0.4% Polymer | 97 | 225 | | <LOQ |

Example 46

Polyethylene Membrane Surface Modified with Phosphoric Acid 2-Hydroxyethylmethacrylate (PAHEMA)

In another experiment, a membrane was modified to incorporate a multivalent ion stimulus, where the membrane can be used for removal of residual stimulus responsive polymer.

A 16% aqueous mixture of PAHEMA was prepared according to the following recipe: 16 g of PAHEMA (Aldrich #695890, 75% PAHEMA and 25% BisHEMPA), 0.2 g of Irgacure 2959, 93.8 g of water. A polyethylene membrane (0.65 um, UPDP MILLIPORE) was prewetted with methanol and exchanged into water and treated with the PAHEMA formulation. The sample was exposed to UV light, washed with methanol and water, and dried. The weight added to the membrane by this surface modification was 4.4%. The infrared spectrum of the membrane displayed a strong methacrylate carbonyl absorption. Staining the membrane with methylene blue (a positively charged dye) gave a deep blue color with a cyan optical density of 1.43.

Example 47

Hydrophilic Polyethylene Membrane Surface Modified with Phosphoric Acid 2-hydroxyethylmethacrylate (PAHEMA)

A 16% aqueous mixture of PAHEMA was prepared according to the following recipe: 16 g of PAHEMA (Aldrich #695890, 75% PAHEMA and 25% BisHEMPA), 0.2 g of Irgacure 2959, 93.8 g of water. A hydrophiloic membrane (0.65 um, MPLC MILLIPORE) was directly contacted with the PAHEMA solution. UV exposure and washing as above gave a membrane with a 7.6% add on. The infrared spectrum of the membrane displayed a strong methacrylate carbonyl absorption. Staining the membrane with methylene blue (a positively charged dye) gave a deep blue color with a cyan optical density of 1.45.

Example 48

Hydrophilic Polymethacrylate Resin Modified with Phosphoric Acid 2-hydroxyethylmethacrylate (PAHEMA)

In another experiment, a resin was modified to include a stimulus, where the modified resin could then be used for removing the residual polymer.

A solution is prepared with the following composition: 60 ml allyl glycidyl ether(AGE), 110 g 4M NaOH, 12 g sodium sulfate. To this solution 60 ml of ToyoPearl65C media is added and the mixture is placed in a rotating hybridizer at 50 C for 16 hours. The media are separated and washed by standard procedures. The PAHEMA grafting solution is prepared as follows: 1.0 g PAHEMA, 0.06 g ammonium persulfate, 9.0 g water. To this solution is added 5 ml of the AGE modified ToyoPearl media. The mixture is placed in a hybridizer at 80 C for 16 hours. Separating and washing by standard procedures gives the PAHEMA modified resin. This product stains dark blue when treated with a 0.01% aqueous solution of methylene blue which is a positively charged dye.

Example 49

Stimulus Responsive Polymer Binding with an Hydrophilic Polyethylene Membrane Surface Modified with Phosphoric Acid 2-hydroxyethylmethacrylate (PAHEMA)

The PAHEMA modified MPLC membrane (Example 47) was used to capture polyallylamine (PAA) polymer from 3 solutions containing 100, 10, and 1 ppm PAA respectively using the following experimental procedure. A membrane disk 20 mm processed diameter in 15 cc cell holder. PAA solutions processed at 1.5 cc/sec. The membrane was washed in and out of cell holder with 100 ml, PBS buffer. Processed membrane stained with Ponceau S.

Ponceau S is a negatively charged dye that absorbs strongly to positively charged surfaces. When PAA is absorbed by the PAHEMA modified membrane, the surface is converted from a negative to positive charge. This conversion is easily observed by staining the processed solution with Ponceau S. A good measure of degree of staining with Ponceau S is the magenta optical density as measured with a Macbeth Densitometer. The magenta optical density values for various processed membranes (i.e. loaded with PAA) on both the upstream and downstream sides of the membrane are shown in Table 14.

As can be seen for the 1 ppm case, all of the PAA is captured on the upstream side of the membrane. For the 15 mL of processed solution, this corresponds to 4.8 micrograms of PAA/cm2 of membrane surface.

TABLE 14

| PAA Loading (PAA processed) | Upstream (Topside) Magenta Optical Density | Downstream (Bottomside) Magenta Optical Density |
|---|---|---|
| Unprocessed | 0 | 0 |
| 100 ppm | 0.77 | 0.77 |
| 10 ppm | 0.75 | 0.70 |
| 1 ppm | 0.60 | 0 |

Accordingly, based on the results from this Example, it may be concluded that the modified membranes and resins described herein may be used for reducing the level of residual polymer or completely removing the residual polymer.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A soluble stimulus responsive polymer comprising a polyvinylamine backbone comprising one or more hydrophobic groups attached to the backbone, wherein the polymer is capable of binding and precipitating a biomolecule of interest in a sample upon addition of a stimulus.

2. The soluble stimulus responsive polymer of claim 1, wherein the backbone comprises at least two monomeric units.

3. The soluble stimulus responsive polymer of claim 2, wherein the backbone comprises at least three monomeric units.

4. The soluble stimulus responsive polymer of claim 2, wherein each monomeric unit in the backbone comprises a charge.

5. The soluble stimulus responsive polymer of claim 2, wherein at least 50% of the monomeric units comprise a charge.

6. The soluble stimulus responsive polymer of claim 1, wherein the biomolecule of interest is a therapeutic polypeptide.

7. The soluble stimulus responsive polymer of claim 1, wherein the biomolecule of interest is an impurity present in a sample.

8. The soluble stimulus responsive polymer of claim 7, wherein the impurity is selected from the group consisting of host cell protein, endotoxin, DNA, RNA, viruses, lipids, whole cells and cellular debris.

9. The soluble stimulus responsive polymer of claim 1, wherein the stimulus is a multivalent ion.

10. The soluble stimulus responsive polymer of claim 9, wherein the multivalent ion is phosphate or citrate.

11. The soluble stimulus responsive polymer of claim 7, wherein the therapeutic polypeptide is an antibody.

12. The soluble stimulus responsive polymer of claim 11, wherein the antibody is a monoclonal antibody.

13. A method of separating a target molecule from one or more impurities in a sample, wherein the method comprises the steps of:
    (a) providing a sample comprising a target molecule and one or more impurities;
    (b) contacting the sample with a soluble stimulus responsive polymer comprising a polyelectrolyte backbone comprising one or more hydrophobic groups attached to the backbone thereby to form a complex of polymer and the one or more impurities; and
    (c) adding a stimulus to the sample, thereby to precipitate the complex out of solution,
    thereby to separate the target molecule from one or more impurities.

14. The method of claim 13, wherein the method further comprises one or more filtration steps.

15. The method of claim 13, wherein the method further comprises one or more chromatography step.

16. The method of claim 13, wherein the stimulus is a multivalent ion.

17. The method of claim 16, wherein the multivalent ion is phosphate or citrate.

18. The method of claim 13, wherein the polyelectrolyte backbone comprises at least two monomeric units, at least 50% of the units comprising a charge.

19. The method of claim 13, wherein the polyelectrolyte backbone comprises at least three monomeric units, at least 50% of the units comprising a charge.

20. A soluble stimulus responsive polymer comprising the following structure:

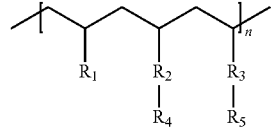

Wherein the polymer comprises a carbon containing polyelectrolyte backbone; $R_1$, $R_2$ and $R_3$ are charged groups which form a part of the backbone; $R_4$ is a hydrophobic group attached to a charged group in the backbone; $R_5$ is a group possessing a charge opposite of the charge found in $R_1$, $R_2$ or $R_3$; and n is the number of monomeric units in the polymer, wherein n is equal to or greater than 2.

21. A method of separating an antibody from one or more impurities in a sample while minimizing residual amounts of polymer, the method comprising the steps of:
    (a) providing a sample comprising an antibody and one or more impurities;
    (b) contacting the sample with a soluble stimulus responsive polymer comprising a polyelectrolyte backbone comprising one or more hydrophobic groups attached to the backbone under a first set of conditions suitable for the polymer to bind one or more impurities, thereby to form a first complex of polymer and one or more impurities, wherein the first set of conditions comprise adjusting pH or salt concentration of the sample during or after the addition of the polymer;

(c) precipitating the first complex from the sample under a second set of conditions;

(d) contacting the sample with a stimulus comprising a multivalent ion, thereby to form a second complex of residual polymer and multivalent ion; and (e) precipitating the second complex;

thereby to separate the antibody from one or more impurities in the sample while reducing the amount of residual polymer in the sample.

22. The method of claim 21, wherein the antibody is a monoclonal antibody.

23. The method of claim 21, wherein the one or more impurities is selected from the group consisting of host cell protein, DNA, RNA, viruses, antibody aggregates and cell culture additives.

24. The method of claim 21, wherein the sample comprises a feedstock.

25. The method of claim 21, wherein the sample comprises cell culture media into which an antibody is secreted.

26. The method of claim 21, further comprising one or more chromatography steps.

27. The method of claim 21, further comprising one or more filtration steps.

28. The polymer of claim 1, wherein the hydrophobic group is a phenyl group.

29. A soluble stimulus responsive polymer for separating a target molecule from one or more impurities comprising the following formula:

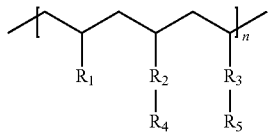

wherein the polymer comprises a carbon containing polyelectrolyte backbone; $R_1$, $R_2$ and $R_3$ are amine groups which form a part of the backbone; $R_4$ is a phenyl group which is attached to 5% to 75% of the $R_1$, $R_2$ or $R_3$ groups; $R_5$ is a cation exchange group modifying 5% to 50% of the $R_1$, $R_2$ or $R_3$ groups; and n is the number of monomeric units in the polymer, wherein n is equal to or greater than 2.

30. A method of separating an antibody from one or more impurities in a sample using a stimulus responsive polymer, while minimizing residual amounts of polymer, the method comprising the steps of:

(a) providing a sample comprising an antibody and one or more impurities;

(b) contacting the sample with a soluble stimulus responsive polymer comprising a polyelectrolyte backbone comprising one or more hydrophobic groups attached to the backbone under a first set of conditions suitable for the polymer to bind one or more impurities, thereby to form a first complex of polymer and one or more impurities, wherein the first set of conditions comprise adjusting pH or salt concentration of the sample during or after the addition of the polymer;

(c) flocculating the first complex from the sample under a first set of conditions;

(d) removing the flocculated solids;

(e) contacting the sample with a multivalent ion, thereby to form a second complex of residual polymer and multivalent ion; and (f) precipitating the second complex thereby to separate the antibody from one or more impurities in the sample while reducing the amount of residual polymer in the sample.

31. A method of separating a target molecule from one or more impurities in a sample, wherein the method comprises the steps of:

(a) providing a sample comprising a target molecule and one or more impurities;

(b) contacting the sample with a soluble multivalent ion responsive polymer comprising a polyelectrolyte backbone comprising one or more hydrophobic groups attached to the backbone, wherein a multivalent ion is added during or after addition of the polymer, thereby to form a complex of polymer and the one or more impurities;

(c) precipitating the complex out of solution, thereby to separate the target molecule from one or more impurities.

32. The method of claim 31, wherein the multivalent ion stimulus is phosphate or citrate.

33. The method of claim 31, wherein the stimulus responsive polymer is a copolymer.

34. The method of claim 31, further comprising the step of removing a residual amount of polymer after step (c), wherein the step comprises the use of a membrane or resin modified with a multivalent ion.

35. The method of claim 34, wherein the multivalent ion is phosphate.

36. The method of claim 13, wherein the polymer is selected from polyallylamine modified with a hydrophobic group and polyvinylamine modified with a hydrophobic group.

37. The method of claim 36, wherein the hydrophobic group is a benzyl group.

38. The method of claim 30, wherein the polymer is selected from polyallylamine modified with a hydrophobic group and polyvinylamine modified with a hydrophobic group.

39. The method of claim 38, wherein the hydrophobic group is a benzyl group.

40. The method of claim 31, wherein the polymer is selected from polyallylamine modified with a hydrophobic group and polyvinylamine modified with a hydrophobic group.

41. The method of claim 40, wherein the hydrophobic group is a benzyl group.

* * * * *